(12) United States Patent
Negoro et al.

(10) Patent No.: US 7,018,960 B2
(45) Date of Patent: Mar. 28, 2006

(54) LUBRICANT COMPOSITION, METHOD FOR USING AND PREPARING THEREOF AND MOLECULAR COMPLEX COMPOUND USED FOR THE SAME

(75) Inventors: Masayuki Negoro, Kanagawa (JP); Ken Kawata, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 290 days.

(21) Appl. No.: 10/163,605

(22) Filed: Jun. 7, 2002

(65) Prior Publication Data

US 2003/0096715 A1    May 22, 2003

(30) Foreign Application Priority Data

Jun. 11, 2001   (JP) .............................. 2001-175760

(51) Int. Cl.
    C10M 105/06      (2006.01)
(52) U.S. Cl. ...................... 508/258; 508/221; 508/229
(58) Field of Classification Search ................ 508/258, 508/229, 221
    See application file for complete search history.

(56) References Cited

U.S. PATENT DOCUMENTS

| | | | |
|---|---|---|---|
| 3,189,542 A | | 6/1965 | Morway et al. |
| 3,250,708 A | | 5/1966 | Dazzi et al. |
| 5,032,301 A | | 7/1991 | Pawloski et al. |
| 6,653,263 B1 | * | 11/2003 | Kupper et al. .............. 508/582 |

FOREIGN PATENT DOCUMENTS

| | | |
|---|---|---|
| CA | 2384386 A1 | 3/2001 |
| DE | 199 42 534 A1 * | 3/2001 |
| DE | 199 42 536 A1 * | 3/2001 |
| EP | 0 320 450 A1 | 9/1989 |
| EP | 1 164 182 A1 | 12/2001 |
| GB | 977587 | 12/1964 |
| WO | WO 00/53701 * | 9/2000 |
| WO | WO 01/18160 A2 | 3/2001 |

OTHER PUBLICATIONS

Daniela Goldmann et al, "New disc-shaped triarylamino-1, 3,5-triazines with heteroaromatic central cores," *Liquid Crystals*, Taylor and Francis Ltd., London, GB, vol. 21, No. 5, Nov. 1, 1996 pp. 619-623 (XP000639764).
EPO Partial Search Report dated Aug. 29, 2002, in EP Application No. 02 01 2439.

* cited by examiner

*Primary Examiner*—Elizabeth D. Wood
(74) *Attorney, Agent, or Firm*—Buchanan Ingersoll PC

(57) ABSTRACT

A lubricant composition containing a molecular complex compound formed by inter-molecular interaction of one or more keto-enol tautomeric compounds, wherein said molecular complex compound contains as a constituent a keto-enol tautomeric compound (but excluding specified triarylmelamine compounds) represented by the formula (I) (where, $Q^{11}$ represents an oxygen atom, sulfur atom or $N(R^{13})$; $R^{11}$ to $R^{13}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{11}$ and $R^{12}$, or $R^{11}$ and $R^{13}$ may bind with each other-to thereby form a cyclic structure) is disclosed

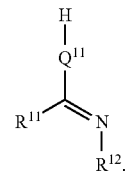

formula (I)

13 Claims, 1 Drawing Sheet

LUBRICANT COMPOSITION, METHOD FOR USING AND PREPARING THEREOF AND MOLECULAR COMPLEX COMPOUND USED FOR THE SAME

FIELD OF THE INVENTION

The present invention belongs to a technical field of lubricant composition to be supplied to mechanical friction sliding members and a method for preparing thereof, and more specifically belongs to a technical field of lubricant excellent in low friction properties and wear resistance under extreme pressure, and also in sustainability of such properties, and a method for preparing thereof. And the present invention also relates to a novel molecular complex compound useful as extreme pressure agents, friction coefficient modifiers and anti-wear additives.

RELATED ART

Performances required for lubricant relate to that it should be able to lower friction coefficient at mechanical friction sliding members over a wide temperature range and pressure range, and that such effects are sustained as long as possible. It is also expected for the lubricant to not only improve lubricating properties between mechanical friction sliding members, but also to thereby good provide wear resistance to such friction sliding members in themselves. Effects, which is brought about by lubricant such as engine oil, of reducing friction coefficient of the friction sliding members and increasing service life thereof directly result in improved fuel cost for mechanical driving, or in other words, energy saving. Elongation of the service life of engine oil not only ensures reduction in waste oil but also reduction in $CO_2$ emission, so that it will be desirable in terms of environmental compatibility which has increasingly been attracting recent public attention. As for bearings or gears, which operate under particularly severe frictional conditions among various sliding members for use in industrial machines, use of conventional lubricant such as lubricating oil or grease may result in film breakage or sticking of the lubricant under particularly severe lubricating conditions, which makes it difficult to obtain a desired low friction coefficient due to abrasion scars. This sometimes lowers the reliability of apparatus, and tends to increase severity of the friction conditions especially for the case that the apparatus is to be downsized, which has been one reason for preventing the apparatus from being downsized. So that there has been a strong demand for a lubricant which can bring about the effects even under severe conditions, can contribute to downsizing of the apparatus, and is excellent in energy saving property.

In addition, it is demanded for lubricants to be applied on the surface of a high-density magnetic recording medium, or to sliding or rotating members of micro-machines that the foregoing properties can be sustained at an extremely small amount. That is, a strongly desired lubricant is such that being capable of covering friction surface in a necessarily smallest amount to thereby reduce friction coefficient of the sliding surfaces, and such that not only being capable of improving the wear resistance but also sustaining such effect as long as possible. To fulfill the requirements, the lubricants are inevitably demanded to have a property that they can readily form a uniform and smooth thin film.

Lubricants which have previously been used are generally such that comprising a lubricant base oil as a major component, and a lubricant aids such as an organic compound blended thereto. Diorganodithiocarbamic acid is a typical lubricant aids, and it is known that a metal salt thereof has a variety of functions of an antioxidant, wear resisting agent and corrosion suppressive additive for the lubricants. For example, a zinc salt disclosed in U.S. Pat. No. 4,278,587, an antimony salt disclosed in U.S. Pat. No. 4,290,202, a molybdenum salt disclosed in U.S. Pat. No. 460,438, and metal salts containing nickel, copper, cobalt, iron, cadmium, manganese or so disclosed in Published PCT application No. WO95/19411 have remarkable effects of keeping low friction property and low abrasion property at sliding members even under severe conditions. In particular, organic molybdenum compound recently attracts an attention as a lubricant auxiliary. The organic molybdenum compound is excellent in various properties such as wear resistance, durability under extreme pressure (load resistance) and low friction property even during operation of sliding members of a mechanical apparatus under severe frictional conditions such as high temperature, high or low speed, high load, downsizing and weight reduction, so that the compound attracts a good deal of attention as a material capable of effectively exhibiting lubricating effects under a marginal lubricating condition which is higher in pressure than the fluid lubricating condition under ordinary pressure.

It has however been known that the organic molybdenum compound is more effective when it is used in combination with zinc dithiophosphate than in an independent use. Masayoshi Muraki et al reported in *Tribologist* 38, 10 (1993) a mechanism, according to which a thin film of zinc dithiophosphate once formed on the sliding surface assists adhesion, reaction and decomposition of molybdenum thiocarbamate or molybdenum dithiophosphate to thereby form a mixed coated film comprising molybdenum sulfide and molybdenum oxide. Katsuya Arai et al reported in *Tribologist* 44, 46 (1999) that they analyzed a depth profile of element composition of the friction sliding surface by XPS (X-ray photoelectronic spectroscopy), and confirmed that molybdenum, sulfur and oxygen, all of which derived from dithiocarbamate, gradually decreased but iron increased as the depth from the surface increases, which is ascribable to formation of a composite film of metal iron supplied from the sliding surface and molybdenum reacted therewith, and such composite film contributes to lowered friction coefficient and increased wear resistance. Still another study was reported by Takashi Kikuchi et al in JSAE Paper 9537538 (1995), according to which also sulfur compounds such as sulfurized oil and fat, olefin sulfate and phenate sulfate, besides foregoing zinc dithiophosphate, show synergistic effect of reducing friction in cooperation with molybdenum dithiocarbamate.

Although molybdenum dithiocarbamate is a desirable material capable of exhibiting an excellent lubricating effect even under severe frictional conditions, it is apparently inappropriate in view of environmental compatibility since the lubricating oil contains a considerable amount of heavy metals such as molybdenum and zinc, sulfide which can readily be oxidized to thereby produce sulfur oxide adversely affecting the lubricating oil or sliding member per se, and even affecting the environment, and phosphoric acid which undesirably eutrophicates rivers and seas. Another disadvantage relates to that molybdenum oxide/sulfide film formed on the sliding surface is gradually peeled off under friction to thereby produce a new film, so that shortage in the amount of either of organic molybdenum compound or organic zinc compound, which are source materials, will sharply ruin the effect. A countermeasure of increasing the amount of such organic molybdenum compound and organic zinc compound is however undesirable since it may increase the amount of byproducts generated in the system by such peeling-off of the film, which adversely affect the sliding machinery per se, so that it is less expectable in a current situation of a system using the foregoing organic molybdenum compound to improve fuel cost through elongation of the service life of the lubricant. As has been described in the above, there has been no proposal of a lubricant which is free from any of environmentally hazardous substance or environmental pollutant such as heavy metal elements, phosphate compounds and sulfides, capable of exhibiting excellent lubricating properties, and capable of retaining such properties for a long period.

SUMMARY OF THE INVENTION

It is therefore an object of the present invention to provide a lubricant composition capable of exhibiting excellent properties not only in a state of mixture with conventional lubricant base oil, but also in a state not mixed with such lubricant base oil, and a method for preparing thereof. It is another object of the present invention to provide a lubricant composition capable of retaining low friction property and high wear on the sliding surface resistance for a long period, and a method for preparing thereof. It is another object of the present invention to provide a lubricant composition capable of readily forming a uniform thin film, and being applicable to the surface of magnetic recording media or micro-machines, and a method for preparing thereof. It is still another object of the present invention to provide a lubricant composition excluding environmentally-less-compatible heavy metals, phosphate group and sulfides to thereby concomitantly achieve both of longer service life and environmental compatibility, and a method for preparing thereof.

And it is another object of the present invention to provide a novel molecular complex compound which has excellent properties and are advantageously used for lubricant composition.

In one embodiment, this invention relates to a lubricant composition containing a molecular complex compound formed by inter-molecular interaction of one or more keto-enol tautomeric compounds, wherein said molecular complex compound contains as a constituent a keto-enol tautomeric compound represented by the formula (I) (but excluding any compound represented by the formula (TAM) below):

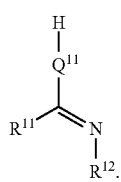

formula (I)

(where, $Q^{11}$ represents an oxygen atom, sulfur atom or $N(R^{13})$; $R^{11}$ to $R^{13}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{11}$ and $R^{12}$, or $R^{11}$ and $R^{13}$ may bind with each other to thereby form a cyclic structure); and

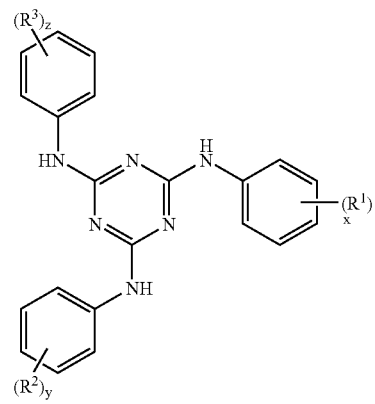

formula (TAM)

(where $R^1$, $R^2$ and $R^3$ independently represents a substituent; x, y and z independently represent an integer of 1 to 5).

In another embodiment, this invention relates to a molecular complex compound formed by inter-molecular interaction of one or more keto-enol tautomeric compounds, containing as a constituent a keto-enol tautomeric compound represented by the formula (IX) (but excluding any compound represented by the formula (TAM) below):

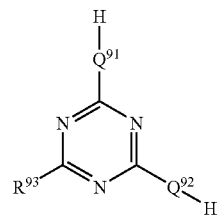

formula (IX)

(where, $Q^{91}$ and $Q^{92}$ independently represents a single bond, $N(R^{94})(R^{94}$ represents a hydrogen or $C_{1-30}$ alkyl group), oxygen atom, sulfur atom, carbonyl, sulfonyl, or any combination thereof; $R^{91}$ and $R^{92}$ independently represents a hydrogen atom, substituted or non-substituted alkyl group, alkenyl group, alkynyl group, aryl group or hetelocyclic group; $R^{93}$ represents a halogen atom, hydroxyl, amino, mercapto, cyano, sulfide, carboxyl or a salt thereof, sulfo or a salt thereof, hydroxyamino, ureido, or urethane); and

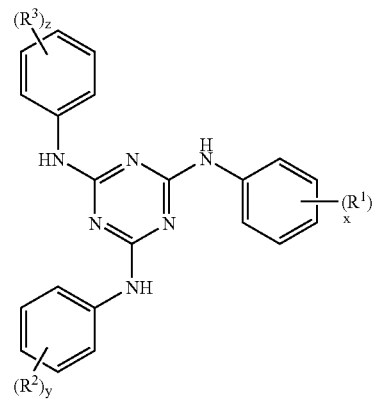

formula (TAM)

(where $R^1$, $R^2$ and $R^3$ independently represents a substituent; x, y and z independently represent an integer of 1 to 5).

In another embodiment, this invention relates to a method for reducing friction coefficient between sliding surfaces which comprises a step of supplying to said sliding surfaces one or more keto-enol tautomeric compounds represented by the foregoing formula (I) (but excluding any compound represented by the foregoing formula (TAM)) so as to form a molecular complex compound which comprises said one or more keto-enol tautomeric compounds as the constituents on said sliding surfaces.

In another embodiment, this invention relates to a method for preparing lubricant composition comprising a step of adding "n" (n is an integer of 1 or above) kinds of keto-enol tautomeric compounds represented by the foregoing formula (I) (but excluding any compound represented by the foregoing formula (TAM)) so as to form a molecular complex compound composed of said "n" kinds of keto-enol tautomeric compounds.

In another embodiments, this invention relates to use of a molecular complex compound formed by inter-molecular interaction of one or more keto-enol tautomeric compounds represented by the foregoing formula (I) (but excluding any compound represented by the foregoing formula (TAM)) for reducing friction coefficient between sliding surfaces.

DETAILED DESCRIPTION OF THE INVENTION

Figure 1:
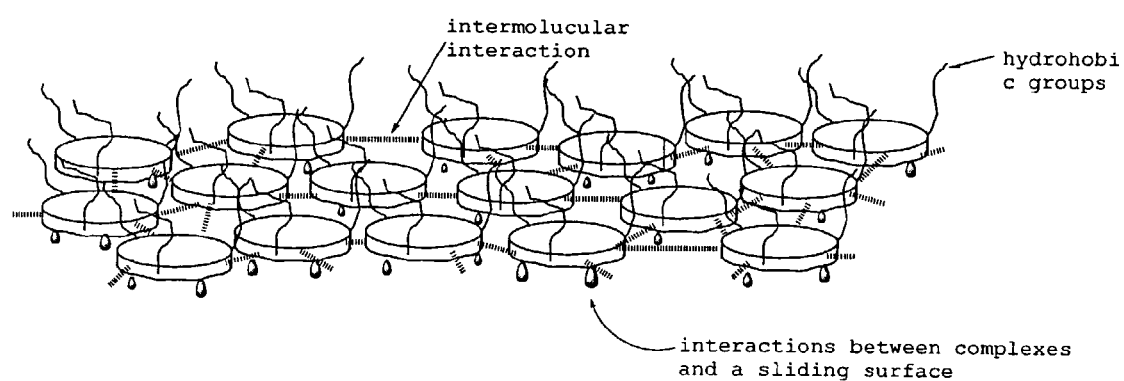
FIG. 1 is a schematic drawing for explaining orientation status of the lubricant composition of the present invention.

The present invention will be detailed below. It should now be noted that, in this specification, any notation for expressing numerical range using a word "to" indicates a range defined by values placed before and after "to", both ends inclusive as minimum and maximum values.

One embodiment of the present invention is a lubricant composition containing a molecular complex compound formed by inter-molecular interaction of one or more keto-enol tautomeric compounds, wherein said molecular complex compound contains as a constituent a keto-enol tautomeric compound represented by the formula (I) (but excluding any compound represented by the formula (TAM) below):

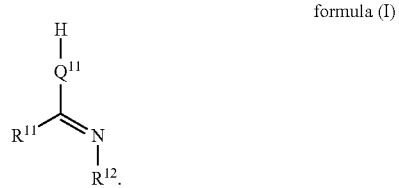

formula (I)

where, $Q^{11}$ represents an oxygen atom, sulfur atom or $N(R^{13})$ $R^{11}$ to $R^{13}$ independently represents a hydrogen atom or a substituent, at least one of which is a substituent containing a $C_4$ or longer alkyl chain or oligoalkyleneoxy chain, a $C_2$ or longer perfluoroalkyl chain, perfluoroalkyl ether chain or organic polysilyl chain. $R^{11}$ and $R^{12}$, or $R^{11}$ and $R^{13}$ may bind with each other to thereby form a cyclic structure.

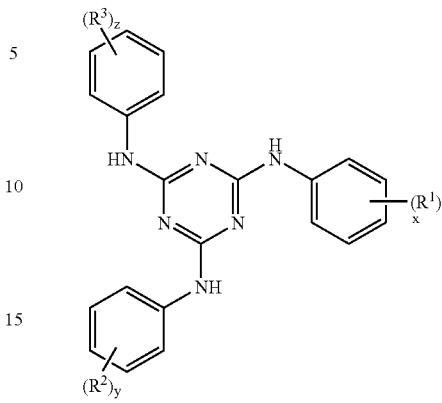

forumula (TAM)

where $R^1$, $R^2$ and $R^3$ independently represents a substituent; and x, y and z independently represents an integer of 1 to 5.

In the foregoing formulae (I) and (TAM), the substituents represented by $R^{11}$ to $R^{13}$, and $R^1$ to $R^3$, respectively, are exemplified by halogen atom, alkyl group (including cycloalkyl group and bicycloalkyl group), alkenyl group (including cycloalkenyl group and bicycloalkenyl group), alkynyl group, aryl group, heterocyclic group, cyano, hydroxyl, nitro, carboxyl, alkoxy group, aryloxy group, silyloxy group, heterocyclic oxy group, acyloxy group, carbamoyloxy group, alkoxycarbonyloxy group, aryloxycarbonyloxy group, amino group (including anilino group), acylamino group, aminocarbonylamino group, alkoxycarbonylamino group, aryloxycarbonylamino group, sulfamoylamino group, alkyl- and arylsulfonylamino group, mercapto group, alkylthio group, arylthio group, heterocyclic thio group, sulfamoyl group, sulfo group, alkyl- and arylsulfinyl group, alkyl- and arylsulfonyl group, acyl group, aryloxycarbonyl group, alkoxycarbonyl group, carbamoyl group, aryl- and heterocyclic azo group, imide group, phosphino group, phosphinyl group, phosphinyloxy group, phosphinylamino group, and silyl group. The substituents $R^{11}$ to $R^{13}$ also include above substituents further substituted with at least one of such substituents.

More specifically, examples of such substituents include halogen atom (e.g., chlorine atom, bromine atom, iodine); alkyl groups [straight-chain, branched, or cyclic, substituted or non-substituted alkyl group, which are typified by alkyl groups (preferably $C_{1-30}$ alkyl groups such as methyl, ethyl, n-propyl, isopropyl, t-butyl, n-octyl, eicosyl, 2-chloroethyl, 2-cyanoethyl, 2-ethylhexyl); cycloalkyl groups (preferably, $C_{3-30}$ substituted or non-substituted cycloalkyl groups such as cyclohexyl, cyclopentyl and 4-n-dodecylcyclohexyl); bicycloalkyl groups (preferably, $C_{5-30}$ substituted or non-substituted bicycloalkyl group, or in other words, a monovalent group obtained by removing one hydrogen atom from $C_{5-30}$ bicycloalkane, such as bicyclo[1,2,2]heptane-2-yl and bicyclo[2,2,2]octane-3-yl); and multicyclo structure having more than two rings, where also alkyl groups contained in the substituents described below (e.g., alkyl group in alkylthio group) express alkyl groups based on the same concept]; alkenyl groups [straight-chain, branched or cyclic, substituted or non-substituted alkenyl groups, which are typified by alkenyl groups (preferably $C_{2-30}$ substituted or non-substituted alkenyl groups such as vinyl, allyl, prenyl, geranyl and oleyl); cycloalkenyl groups (preferably, $C_{3-30}$ substituted or non-substituted cycloalkenyl group, or in other words, a monovalent group obtained by removing one hydrogen atom from $C_{3-30}$ cycloalkene, such as 2-cyclopentene-1-yl and 2-cyclohexene-1-yl); bicycloalkenyl groups (substituted or non-substituted bicycloalkenyl group, preferably $C_{5-30}$ substituted or non-substituted bicycloalkenyl group, or in other words, a monovalent group obtained by removing one hydrogen group from bicycloalkene having one double bond, such as bicyclo[2,2,1]hepto-2-ene-1-yl and bicyclo[2,2,2]octo-2-ene-4-yl); alkynyl groups (preferably $C_{2-30}$ substituted or non-substituted alkynyl groups such as ethynyl, propargyl and trimethylsilylethynyl); aryl groups (preferably $C_{6-30}$ substituted or non-substituted aryl groups such as phenyl, p-tolyl, naphthyl, m-chlorophenyl and o-hexadecanoylaminophenyl); heterocyclic groups (preferably a 5- or 6-membered monovalent group obtained by removing one hydrogen atom from substituted or non-substituted aromatic or non-aromatic heterocyclic compound, and more preferably $C_{3-30}$ 5- or 6-membered aromatic heterocyclic groups, such as 2-furyl, 2-thienyl, 2-pyrimidinyl and 2-benzothiazolyl); cyano; hydroxyl; nitro; carboxyl; alkoxy groups (preferably $C_{1-30}$ substituted or non-substituted alkoxy group such as methoxy, ethoxy, isopropoxy, t-butoxy, n-octyloxy and 2-methoxyethoxy); aryloxy groups (preferably $C_{6-30}$ substituted or non-substituted aryloxy group, such as phenoxy, 2-methylphenoxy, 4-t-butylphenoxy, 3-nitrophenoxy and 2-tetradecanoylaminophenoxy); silyloxy groups (preferably $C_{3-20}$ silyloxy group such as trimethylsilyloxy and t-butyldimethylsilyloxy); heterocyclic oxy groups (preferably $C_{2-30}$ substituted or non-substituted heterocyclic oxy groups such as 1-phenyltetrazol-5-oxy and 2-tetrahydropyranyloxy); acyloxy groups (preferably formyloxy group, $C_{2-30}$ substituted or non-substituted alkylcarbonyloxy groups, $C_{6-30}$ substituted or non-substituted arylcarbonyloxy groups, such as formyloxy, acetyloxy, pivaloyloxy, stearoyloxy, benzoyloxy and p-methoxyphenylcarbonyloxy); carbamoyloxy groups (preferably, $C_{1-30}$ substituted or non-substituted carbamoyloxy groups, such as N,N-dimethylcarbamoyloxy, N,N-diethylcarbamoyloxy, morpholinocarbonyloxy, N,N-di-n-octylaminocarbonyloxy and N-n-octylcarbamoyloxy); alkoxycarbonyloxy groups (preferably $C_{2-30}$ substituted or non-substituted alkoxycarbonyloxy groups, such as methoxycarbonyloxy, ethoxycarbonyloxy, t-butoxycarbonyloxy and n-octylcarbonyloxy); aryloxycarbonyloxy groups (preferably $C_{7-30}$ substituted or non-substituted aryloxycarbonyloxy groups, such as phenoxycarbonyloxy, p-methoxyphenoxycarbonyloxy and p-n-hexadecyloxyphenoxycarbonyloxy); amino groups (preferably amino group, $C_{1-30}$ substituted or non-substituted alkylamino groups and $C_{6-30}$ substituted or non-substituted anilino groups, such as amino, methylamino, dimethylamino, anilino, N-methylanilino and diphenylamino); acylamino groups (preferably formylamino group, $C_{1-30}$ substituted or non-substituted alkylcarbonylamino groups and $C_{6-30}$ substituted or non-substituted arylcarbonylamino groups, such as formylamino, acetylamino, pivaloylamino, lauroylamino, benzoylamino and 3,4,5-tri-n-octyloxyphenylcarbonylamino); aminocarbonylamino groups (preferably $C_{1-30}$ substituted or non-substituted aminocarbonylamino groups, such as carbamoylamino, N,N-dimethylaminocarbonylamino, N,N-diethylaminocarbonylamino and morpholinocarbonylamino); alkoxycarbonylamino groups (preferably $C_{2-30}$ substituted or non-substituted alkoxycarbonylamino groups, such as methoxycarbonylamino, ethoxycarbonylamino, t-butoxycarbonylamino, n-octadecyloxycarbonylamino and N-methylmethoxycarbonylamino); aryloxycarbonylamino groups (preferably, $C_{7-30}$ substituted or non-substituted aryloxycarbonylamino groups, such as phenoxycarbonylamino, p-chlorophenoxycarbonylamino and m-n-octyloxyphenoxycarbonylamino); sulfamoylamino groups (preferably $C_{0-30}$ substituted or non-substituted sulfamoylamino groups, such as sulfamoylamino, N,N-dimethylaminosulfonylamino and N-n-octylaminosulfonylamino); alkyl- and arylsulfonylamino groups (preferably $C_{1-30}$ substituted or non-substituted alkylsulfonylamino groups and $C_{6-30}$ substituted or non-substituted arylsulfonylamino groups, such as methylsulfonylamino, butylsulfonylamino, phenylsulfonylamino, 2,3,5-trichlorophenylsulfonylamino and p-methylphenylsulfonylamino); mercapto; alkylthio groups (preferably $C_{1-30}$ substituted or non-substituted alkylthio groups, such as methylthio, ethylthio and n-hexadecylthio); arylthio groups (preferably $C_{6-30}$ substituted or non-substituted arylthio groups, such as phenylthio, p-chlorophenylthio and m-methoxyphenylthio); heterocyclic thio groups (preferably $C_{2-30}$ substituted or non-substituted heterocyclic thio groups, such as 2-benzothiazolylthio and 1-phenyltetrazol-5-yl-thio); sulfamoyl groups (preferably $C_{0-30}$ substituted or non-substituted sulfamoyl groups, such as N-ethylsulfamoyl, N-(3-dodecyloxypropyl)sulfamoyl, N,N-dimethylsulfamoyl, N-acetylsulfamoyl, N-benzoylsulfamoyl and N-(N'-phenylcarbamoyl)sulfamoyl); sulfo; alkyl- and arylsulfinyl groups (preferably $C_{1-30}$ substituted or non-substituted alkylsulfinyl groups and $C_{6-30}$ substituted or non-substituted arylsulfinyl groups, such as methylsulfinyl, ethylsulfinyl, phenylsulfinyl and p-methylphenylsulfinyl); alkyl- and arylsulfonyl groups (preferably $C_{1-30}$ substituted or non-substituted alkylsulfonyl groups and $C_{6-30}$ substituted or non-substituted arylsulfonyl groups, such as methylsulfonyl, ethylsulfonyl, phenylsulfonyl and p-methylphenylsulfonyl); acyl groups (preferably formyl group, $C_{2-30}$ substituted or non-substituted alkylcarbonyl groups and $C_{7-30}$ substituted or non-substituted arylcarbonyl groups, such as acetyl, pivaloyl, 2-chloroacetyl, stearoyl, benzoyl, p-n-octyloxyphenylcarbonyl); aryloxycarbonyl groups (preferably $C_{7-30}$ substituted or non-substituted aryloxycarbonyl groups, such as phenoxycarbonyl, o-chlorophenoxycarbonyl, m-nitrophenoxycarbonyl and p-t-butylphenoxycarbonyl); alkoxycarbonyl groups (preferably $C_{2-30}$ substituted or non-substituted alkoxycarbonyl group, such as methoxycarbonyl, ethoxycarbonyl, t-butoxycarbonyl and n-octadecyloxycarbonyl); carbamoyl groups (preferably $C_{1-30}$ substituted or non-substituted carbamoyl groups, such as carbamoyl, N-methylcarbamoyl, N,N-dimethylcarbamoyl, N,N-di-n-octylcarbamoyl and N-(methylsulfonyl)carbamoyl); aryl- and heterocyclic azo groups (preferably $C_{6-30}$ substituted or non-substituted arylazo groups and $C_{3-30}$ substituted or non-substituted heterocyclic azo groups, such as phenylazo, p-chlorophenylazo and 5-ethylthio-1,3,4-thiadiazol-2-yl-azo); imide groups (preferably N-succinimide and N-phthalimide); phosphino groups (preferably $C_{2-30}$ substituted or non-substituted phosphino groups, such as dimethylphosphino, diphenylphosphino and methylphenoxyphosphino); phosphinyl groups (preferably $C_{2-30}$ substituted or non-substituted phosphinyl groups, such as phosphinyl, dioctyloxyphosphinyl and diethoxyphosphinyl); phosphinyloxy groups (preferably $C_{2-30}$ substituted or non-substituted phosphinyloxy groups, such as diphenoxyphosphinyloxy and dioctyloxyphosphinyloxy); phosphinylamino groups (preferably $C_{2-30}$ substituted or non-substituted phosphinylamino groups, such as dimethoxyphosphinylamino and dimethylaminophosphinylamino); silyl groups (preferably $C_{3-30}$ substituted or non-substituted silyl groups, such as trimethylsilyl, t-butyldimethylsilyl and phenyldimethylsilyl).

Of these substituents, those having a hydrogen atom may have an additional substituent which substitutes such hydrogen atom. Examples of such additional substituent include alkylcarbonylaminosulfonyl group, arylcarbonylaminosulfonyl group, alkylsulfonylaminocarbonyl group and arylsulfonylaminocarbonyl group, which are more specifically methylsulfonylaminocarbonyl, p-methylphenylsulfonylaminocarbonyl, acetylaminosulfonyl and benzoylaminosulfonyl groups.

It is to be noted that at least one of the substituents $R^{11}$ to $R^{13}$ is a substituent containing a $C_4$ or longer alkyl chain, oligoalkyleneoxy chain, a $C_2$ or longer perfluoroalkyl chain, perfluoroalkylether chain or organic polysilyl chain. The substituents $R^{11}$ to $R^{13}$ themselves may be a $C_4$ or longer alkyl chain or the like, or it is also allowable that the substituents described in the above are further substituted with such $C_4$ or longer alkyl chain or the like.

Such $C_4$ or longer alkyl chain may be a straight chain or branched chain. Preferable examples of the substituents containing the $C_4$ or longer straight alkyl chain include n-octyl, n-octyloxy, n-octylthio, n-octylamino, n-nonyl, n-nonyloxy, n-decyl, n-decyloxy, n-undecyl, n-undecyloxy, n-dodecyl, n-dodecyloxy, n-dodecylthio, n-dodecylamino, n-pentadecyl, n-pentadecyloxy, n-hexadecyl, n-hexadecyloxy, n-hexadecylthio and n-hexadecylamino. On the other hand, preferable examples of the substituents containing the $C_4$ or longer branched alkyl chain include 2-ethylhexyl, 2-ethylhexyloxy, 2-ethylhexylthio, 2-ethylhexylamino, 2-hexyldecyl, 2-hexyldecylthio, 2-hexyldecylamino, 3,7,11,15-tetramethylhexadecyl, 3,7,11,15-tetramethylhexadecyloxy, 3,7,11,15-tetramethylhexadecylthio and 3,7,11,15-tetramethylhexadecylamino.

The alkyl portion of the oligoalkyleneoxy chain may be a straight chain or branched chain. The substituents containing the oligoalkyleneoxy chain include diethyleneoxy group, triethyleneoxy group, tetraethyleneoxy group, dipropyleneoxy group and hexyloxyethyleneoxyethyleneoxy group.

The alkyl portion of the $C_2$ or longer perfluoroalkyl chain may be a straight chain or branched chain. Preferable examples of the substituent containing the branched perfluoroalkyl chain include pentadecylfluoroheptyl group, pentadecylfluoroheptylcarbonyloxy group, heptadecylfluorooctyl group and pentadecylfluorooctylsulfonyl group. The alkyl portion of the perfluoroalkylether chain may be a straight chain or branched chain. Examples of the substituent containing such perfluoroalkylether chain include isopropyleneoxide, methylene oxide, ethylene oxide and its mixed chains, and substituents obtained by substituting the alkyl portion of the propylene oxide with fluorine atoms.

The organic polysilyl chain is such that having a silicon-atom-containing group as a side chain of a long-chained substituent (e.g., poly(p-trimethylsilylstyrene) and poly(1-trimethylsilyl-1-propine)), or such that having silicon atoms within a main chain of a long-chained substituent, where the latter is more preferable. Such preferable long-chained substituent having silicon atoms within the main chain thereof can be exemplified by those having a repetitive unit represented by the formula (s) below and having any of straight-chained, branched, cyclic or polycyclic structure.

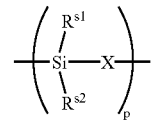

formula (s)

where, $R^{s1}$ and $R^{s2}$ independently represents a substituent. $R^{11}$ and $R^{s2}$ may bind with each other to thereby form a cyclic structure. More specifically, $R^{s1}$ and $R^{s2}$ can be typified by the substituents represented by $R^{22}$ to $R^{13}$ in the foregoing formula (I). Alkyl group is most suitable. X represents an atomic group which comprises an oxygen atom, nitrogen atom, alkylene group, phenylene group, silicon atom, metal atom or any combinations thereof. X is preferably an oxygen atom or an atomic group composed of an oxygen atom and alkylene group, and more preferably, an oxygen atom. A notation "p" is an integer of 1 to 200, and preferably 3 to 30. Specific examples of the organic polysilyl chain include polysiloxane, polysilazane, polysilmethylene, polysilphenylene, polysilane, and polymetallosiloxane.

In the formula (I), $R^{11}$ and $R^{12}$, or $R^{11}$ and $R^{13}$ may bind with each other to thereby form a cyclic structure. The cyclic structures possibly formed by linking of $R^{11}$ and $R^{12}$ include heterocycles such as pyridine ring, pyrimidine ring, pyrazine ring, pyrazole ring, oxazole ring and thiazole ring; benzo condensed rings thereof; and heterocyclic aromatic condensed rings such as purine ring, naphthylizine ring and pteridine ring. The cyclic structures possibly formed by liking of $R^{11}$ and $R^{13}$ include pyrrolidine ring, thiazoline ring and piperidine ring.

The compound represented by the formula (I) includes a compound represented by the formula (II) (but excluding any compound represented by the foregoing formula (TAM)):

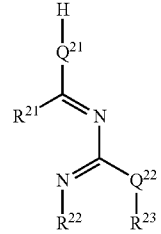

formula (II)

where, $Q^{21}$ and $Q^{22}$ independently represents an oxygen atom, sulfur atom or $N(R^{24})$; $R^{21}$ to $R^{24}$ independently represents a hydrogen atom or substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{21}$ and $R^{22}$, $R^{22}$ and $R^{23}$, or $R^{21}$ and $R^{24}$ may bind with each other to thereby form a cyclic structure.

In the formula (II), substituents respectively represented by $R^{21}$ to $R^{24}$ may be the same as those respectively represented by $R^{11}$ to $R^{13}$ in the foregoing formula (I), and also the preferable examples thereof may be the same. The substituent containing a $C_4$ or longer alkyl chain, oligoalkyleneoxy chain, $C_2$ or longer perfluoroalkyl chain, perfluoroalkylether chain or organic polysilyl chain may be the same with that explained in relation to the formula (I), and also the preferable examples thereof may be the same.

In the formula (II), cyclic structures possibly formed by linking of $R^{21}$ and $R^{22}$ include heterocycles such as imidazole ring, triazole ring, oxadiazole ring, pyrimidine ring and triazine ring; benzo condensed ring (e.g., quinazoline ring) thereof; and heterocyclic aromatic condensed ring such as purine ring, naphthylizine ring and pteridine ring. The cyclic structures possibly formed by liking of $R^{22}$ and $R^{23}$, or $R^{21}$ and $R^{24}$ include pyrrolidine ring, thiazoline ring and piperidine ring, pyrazole ring, oxazole ring and thiazole ring.

The compound represented by the formula (I) (but excluding any compound represented by the foregoing formula (TAM)) preferably has a cyclic structure since such structure allows formation of planar complex compound capable of effectively covering the sliding surface, and more preferably has a cyclic structure containing a nitrogen atom as represented by the formula (I). Preferable examples of the compounds having such cyclic structure include keto-enol tautomeric compounds represented by the formulae (III) to (XI) (but excluding any compound represented by the foregoing formula (TAM)). In particular those represented by any of the formulae (III) to (IX) included within a range of those represented by the formula (II) are preferable.

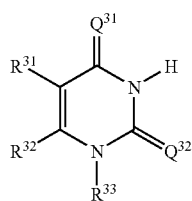

forumula (III)

In the formula (III), $R^{31}$ to $R^{33}$ independently represent a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $Q^{31}$ and $Q^{32}$ independently represents n oxygen atom or a sulfur atom; $R^{31}$ and $R^{32}$, or $R^{32}$ and $R^{33}$ may bind with each other to thereby form a cyclic structure.

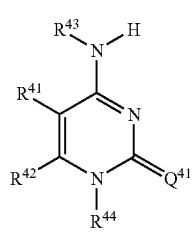

formula (IV)

In the formula (IV), $R^{41}$ to $R^{44}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $Q^{41}$ and represents an oxygen atom or a sulfur atom; $R^{41}$ and $R^{42}$, $R^{41}$ and $R^{43}$, or $R^{42}$ and $R^{44}$ may bind with each other to thereby form a cyclic structure.

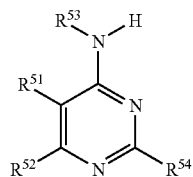

formula (V)

In the formula (V), $R^{51}$ to $R^{54}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{51}$ and $R^{52}$, or $R^{51}$ and $R^{53}$ may bind with each other to thereby form a cyclic structure.

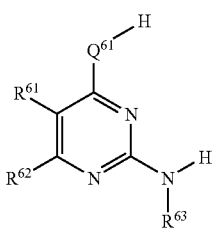

formula (VI)

In the formula (VI), $R^{61}$ to $R^{63}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $Q^{61}$ represents an oxygen atom or sulfur atom; $R^{61}$ and $R^{62}$ may bind with each other to thereby form a cyclic structure.

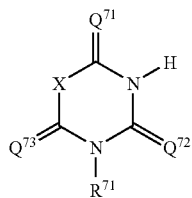

formula (VII)

In the formula (VII), $Q^{71}$ to $Q^{73}$ independently represents an oxygen atom or a sulfur atom; X represents —C(=$R^{71}$)— or —C($R^{72}$)($R^{73}$)—; $R^{71}$ represents a substituent; $R^{72}$ and $R^{73}$ independently represents a hydrogen atom or a substituent; at least one of $R^{71}$ to $R^{73}$ represents a substituent containing a $C_4$ or longer alkyl chain or oligoalkyleneoxy chain, a $C_2$ or longer perfluoroalkyl chain, perfluoroalkyl ether chain or organic polysilyl chain; $R^{72}$ and $R^{73}$ may bind with each other to thereby form a cyclic structure.

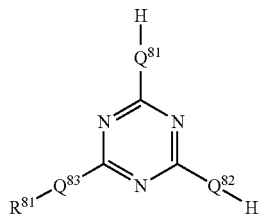

formula (VIII)

In the formula (VIII), $Q^{81}$ to $Q^{83}$ independently represents an oxygen atom, a sulfur atom or $N(R^{82})$; $R^{81}$ and $R^{82}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{81}$ and $R^{82}$ may bind with each other to thereby form a cyclic structure when $Q^{83}$ represents $N(R^{82})$

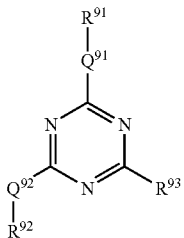

formula (IX)

In the formula (IX), $Q^{91}$ and $Q^{92}$ independently represents a single bond, $N(R^{94})$ ($R^{94}$ represents a hydrogen or alkyl group of $C_{1-30}$), oxygen atom, sulfur atom, carbonyl, sulfonyl, or any combination thereof; $R^{91}$ and $R^{92}$ independently represents a hydrogen atom, substituted or non-substitutive alkyl group, alkenyl group, alkynyl group, aryl group or hetelocyclic group; $R^{93}$ represents a halogen atom, hydroxyl, amino, mercapto, cyano, sulfide, carboxyl and the salt, sulfo and the salt, hydroxyamino, ureido, or urethane.

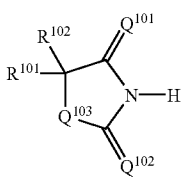

formula (X)

In the formula (X), $Q^{101}$ to $Q^{103}$ independently represents an oxygen atom, sulfur atom or $N(R^{103})$; $R^{101}$ to $R^{103}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain.

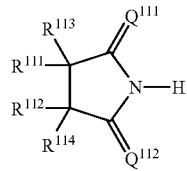

formula (XI)

In the formula (XI), $Q^{111}$ and $Q^{112}$ independently represents an oxygen atom, sulfur atom or $N(R^{115})$; $R^{111}$ to $R^{115}$ independently represents a hydrogen atom or a substituent, at least one of which being a substituent containing a $C_4$ or longer alkyl chain or oligoalkyleneoxy chain, a $C_2$ or longer perfluoroalkyl chain, perfluoroalkyl ether chain or organic polysilyl chain; $R^{111}$ and $R^{113}$, $R^{113}$ and $R^{114}$, $R^{113}$ and $R^{115}$, $R^{112}$ and $R^{114}$, or $R^{114}$ and $R^{115}$ may bind with each other to thereby form a cyclic structure such as spiro ring.

In the foregoing formulae (III) to (XI), substituents represented by $R^{31}$ to $R^{33}$, $R^{41}$ to $R^{44}$, $R^{51}$ to $R^{54}$, $R^{61}$ to $R^{68}$, $R^{71}$ to $R^{73}$, $R^{81}$, $R^{82}$, $R^{101}$ to $R^{103}$ and $R^{111}$ to $R^{115}$ may be the same as those represented by $R^{11}$ to $R^{13}$ in the formula (I), and also the specific and preferable examples thereof may be the same In the formula (VII), $=R^{71}$ is typified as those capable of forming carbon-carbon double bond such as methylene group ($=CH_2$), isopropylidene group ($=CMe_2$), nonylidene group ($=CH(n)C_8H_{17}$) and benzylidene group ($=CHC_6H_5$); those capable of forming carbon-nitrogen double bond such as imino group ($=NH$), phenylimino group($=NC_6H_5$) and octylimino group($=N-(n)C_8H_{17}$); those capable of forming carbon-oxygen double bond such as oxo group ($=O$); and those capable of forming carbon-sulfur double bond such as thioxo group ($=S$).

The compounds represented by the formulae (III) to (VIII) (X) and (XI) have a substituent containing a $C_4$ or longer alkyl chain or oligoalkyleneoxy chain, a $C_2$ or longer perfluoroalkyl chain, perfluoroalkyl ether chain or organic polysilyl chain. These chains may be the same with specific examples explained in relation to the formula (I), and also the preferable examples thereof may be the same.

In the formula (IX), the specific and preferable examples of substituted or non-substituted alkyl, alkenyl, alkynyl, aryl or hetelocyclic groups represented by $R^{91}$ and $R^{92}$ are respectively same as those represented by $R^{11}$ to $R^{13}$ in the formula (I).

In the forgoing formulae, $R^{31}$ and $R^{32}$, $R^{32}$ and $R^{33}$, $R^{41}$ and $R^{42}$, $R^{41}$ and $R^{43}$, $R^{42}$ and $R^{44}$, $R^{51}$ and $R^{52}$, $R^{51}$ and $R^{53}$, $R^{61}$ and $R^{62}$, $R^{72}$ $R^{73}$, $R^{81}$ and $R^{82}$, $R^{111}$ and $R^{113}$, $R^{113}$ and $R^{114}$, $R^{113}$ and $R^{115}$, $R^{112}$ and $R^{114}$ and $R^{115}$ may bind with each other to form a cyclic structure. Examples of the cyclic structures possibly formed by these groups include the rings which respectively composes aryl group and aromatic heterocyclic group exemplified as the groups having cyclic structure represented by $R^{121}$ in the formula (XII) described later.

The keto-enol tautomeric compound represented by the formula (I) preferably shows pKa of 2 to 12 in its enol form.

The molecular complex compound having the compound represented by the formula (I) as constituents preferably has a combination of functional groups such that allowing the constituents thereof to develop the inter-molecular interaction in a geometrically complementary positional relation, and is thus capable of forming a planar complex compound. "A combination of functional groups such that developing the inter-molecular interaction in a geometrically complementary positional relation" herein generally means any combination which satisfies the following conditions (1) to (5). It is to be defined now that two molecules, which are the constituents of the molecular complex compound and are capable of interacting with each other, are a substrate s and a receptor ρ. A higher level of molecular recognition by the receptor molecule ρ depends on a large difference between free energy of bond with the partner substrate s and free energy of bond with other substrates which is ascribable to a relatively small interaction, where such difference is preferably large deviation from the statistical distribution range. To ensure such large difference in free energy of bond, it is necessary to satisfy the conditions (1) to (5) below:

(1) s and ρ must have steric complementarity both in the shape and size thereof, or in other words, s and ρ must have a convexity and a concavity respectively in their proper sites, where the convexity and concavity means complementary binding sites (e.g., hydrogen bond donor (convexity) and hydrogen bond acceptor (concavity)) as described next in (2);

(2) s and ρ must have interactional complementarity, or in other words, s and ρ must have, on their complementary sites capable of binding with each other, complementary binding sites (e.g., electrostatic factors such as +/−, electric charge/dipole, dipole/dipole, hydrogen bond donor/hydrogen bond acceptor), which is preferably arranged orderly, so as to successfully achieve a complementary electron-atomic core (electrostatic force, hydrogen bond, van der Waals force) distribution map;

(3) ρ and s must have a large contact area between them, which is attainable if a plurality of interactive sites described below are available;

(4) ρ and s must have multiple interaction sites which are necessary since interaction based on non-covalent bond is weaker than that based on covalent bond. For an exemplary case of interaction based on hydrogen bond, it is preferable that the both individually have hydrogen bond donor/hydrogen bond acceptor; and (5) ρ and s must show a strong overall binding. Theoretically, a high stability does not always ensures high selectivity, but most cases apply. In fact, difference in free energy of bond tends to increase as the bond becomes stronger. In other words, a high bond efficiency (bound s presents in a larger amount than free s) requires a strong interaction. So that a strong bond between ρ and s is indispensable in order to achieve an efficient recognition, that is, to achieve both of high stability and high selectivity.

The "planar complex compound" herein is defined as a molecular complex having a configurations, while absorbing on or contacting to the friction sliding surface, which allows such molecular complex to cover it in a minimum number of molecules per unit area depending on the morphology of the molecules composing such molecular complex compound. So that for the case the molecules composing the complex compound has a rod-like shape, the "planar complex compound" has a configuration in which the axis of inertia of the skeletal portion composing such molecule is aligned almost in the same plane with the friction sliding surface, or in other words, in parallel to the friction sliding surface in a dense manner. On the other hand, for the case the skeletal portion composing the molecules which forms the complex compound has a plate-like shape, the "planar complex compound" has a configuration in which the molecular plane of such molecule is aligned almost in the same plane with the friction sliding surface, or in other words, in parallel to the friction sliding surface in a dense manner. It is, however, to be noted that a hydrophobic group in the compound represented by the formula (I), which is typified by an alkyl group, alkoxy group, perfluoroalkyl group or polysilyl group, is not assumed as the skeletal portion. A reason why the expression of "capable of forming a planar complex compound" was used is that the molecular complex compound is only expected to form the planar complex compound when supplied onto the sliding surface, and that it is also allowable that such molecular complex compound does not have a planar structure before supplied onto the sliding surface. The lubricant composition of the present invention can exhibit an excellent lubricating effect when the planar complex compound efficiently covers the friction sliding surface. Even without being mixed with a base oil, the lubricant composition of the present invention can exhibit a distinctively excellent lubricating effect and an improving effect of wear-resistant property of the sliding surface, and can retain such effects for a long period. Such effects are demonstrated even under extreme pressure.

In the present invention, the keto-enol tautomeric functional group in the formula (I) forms one functional group composing the "combination of functional groups such that expressing the inter-molecular interaction in a geometrically complementary positional relation". Examples of another functional group capable of composing the "combination of functional groups such that expressing the inter-molecular interaction in a geometrically complementary positional relation" together with the keto-enol tautomeric functional group in the formula (I) include toutomeric functional groups such as carboxilic acid group, thiocarboxilic acid group, carboamide group, thiocarbodiamide group, carboxylic acid imide group, thiocarboxilic acid imide group and ureide group.

Combination of the compound represented by the formula (I) with (thio)carboxylic acid group, (thio)carboamide group, (thio)carboxylic acid imide group or ureide group is such that strongly suggesting a possibility of stabilization by complementary inter-molecular interaction in a conjugated structure based on an electron flow which can be explained by the classic electron theory of organic chemistry as shown in the formulae (XIII) to (XVI) below. It is to be noted that the formulae (XIII) and (XIV) below show a case in which $Q^{11}$ in the formula (I) represents $N(R^{13})$, while omitting illustration of $R^{11}$, $R^{12}$ and $R^{13}$. In the formulae (XV) and (XVI) below show a case in which the formula (II) expresses a 2,4-bisamino-substituted pyrimidine derivative, while omitting illustration of the substituent.

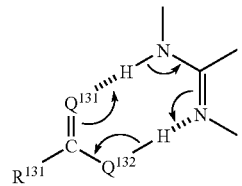

formula (XIII)

-continued

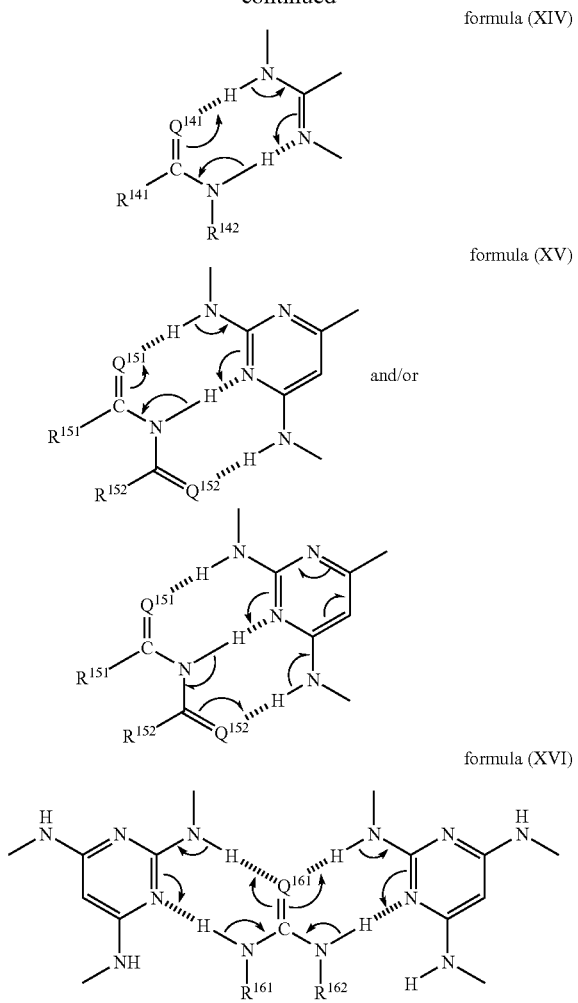

formula (XIV)

formula (XV)

and/or formula (XVI)

In the formulae (XIII) to (XVI) $Q^{131}$, $Q^{132}$, $Q^{141}$, $Q^{151}$, $Q^{152}$ and $Q^{161}$ independently express an oxygen atom or a sulfur atom; and $R^{131}$, $R^{141}$, $R^{142}$, $R^{151}$, $R^{152}$, $R^{162}$ and $R^{162}$ independently express a substituent; where $R^{141}$ and $R^{142}$ $R^{151}$ and $R^{152}$, $R^{161}$ and $R^{162}$ may bind with each other to thereby form a ring. The substituents respectively represented by $R^{131}$, $R^{141}$, $R^{142}$, $R^{151}$, $R^{152}$, $R^{161}$ and $R^{162}$ may be the same with those respective represented by $R^{11}$ to $R^{13}$ in the formula (I), and also the specific and preferable examples thereof may the same. $R^{14}$ and $R^{142}$, $R^{151}$ and $R^{152}$, $R^{161}$ and $R^{162}$ preferably bind with each other to thereby form a ring. Particularly in the formula (XVI), $R^{161}$ and $R^{162}$ preferably bind with each other to thereby form a ring. Examples of such ring include benzoimidazolinone, indazolinone, uracil, thiouracil, benzooxazolinone, succinimide, phthalimide, violuric acid, barbituric acid, pyrazolone, hydantoin, rhodanine, orotic acid, benzothiazolinone, ammelin, coumarine, maleic hydrazide, isatin, 3-indazolinone, parabanic acid, phthalazinone, urazole, alloxan, Meldrum's acid, uramil, caprolactone, caprolactam, thiapendione, tetrahydro-2-pyrimidinone, 2,5-piperazine dione, 2,4-quinazoline dione, 2,4-pteridine diol, folic acid, acetylene urea, guanine, adenine, cytosine, thymine and 2,4-dioxohexahydro-1,3,5-triazine.

The foregoing formulae (XIII) to (XVI) showed specific examples which satisfy the complementary conditions (1) to (5) for formation of the complex compound. Now the steric complementarity described in the condition (1) will be explained referring to the formula (XV). Both of 2,4-diaminotriazine structure (defined as s) and acid imide (defined as ρ) have convexity and concavity. In s, the amino groups form the convexitys and a nitrogen atom in the triazine ring forms the concavity. On the other hand in ρ, the carbonyl groups form the concavities and the central amino group forms the convexity. That is, s has a structure in which convexity, concavity and convexity are aligned in this order, and ρ has a structure in which concavity, convexity and concavity are aligned in this order. This allows s and ρ to readily form hydrogen bonds at three sites at a similar distance, which successfully achieves a strong inter-molecular bonding.

While the interactional complementarity for the condition (2) was described based on a concerted electron flow referring to the formulae (XIII) to (XVI), it can also be discussed based on electrostatic electron donation and acceptance if the start point of the arrow (→) in the formula (XIII) is expressed as d⁻, and the goal of the arrow (→) is expressed as d⁺, as shown in the formula (XVIII) below.

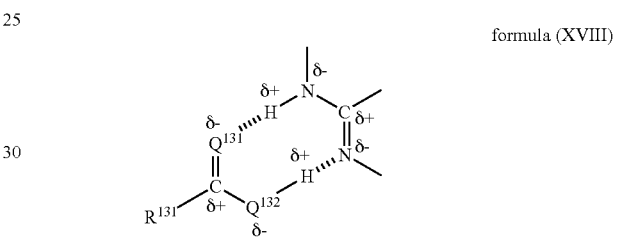

formula (XVIII)

Now a series of electron flow illustrated in the formulae (XIII) to (XVI) will be explained again. The electron flows more advantageously in a two-dimensional (planar) manner than in three-dimensional manner from a viewpoint of energetics. From this point of view, R and R' in the formulae (XIV) to (XVI) preferably bind with each other to form a ring, and further preferably conjugate, and form an aromatic ring. Also R in the formula (XIII) is preferably a group having a cyclic structure, and more preferably such that having an aromatic ring group (including both of aryl group and aromatic heterocyclic group).

As for the formula (XV), 2,4-diaminotriazine structure (A) and acid imide structure (B) form hydrogen bonds at three sites, where the amino group in the structure (A) serves as the convexity, and the nitrogen atom in the triazine ring serves as the concavity.

One preferable embodiment of the molecular complex compound is exemplified by a molecular complex compound which comprises "n" (n is integer of 1 or above) kinds of keto-enol tautomeric compounds $A_1$ to $A_n$ represented by the formula (I) (but excluding any compound represented by the formula (TAM)). Another preferable embodiment of the molecular complex compound relates to such that being based on a combination of a keto-enol tautomeric compound represented by the formula (I) with (thio)carboxilic acid or other keto-enol tautomeric compound, where a combination of a keto-enol tautomeric compound represented by the formula (I) and a (thio) carboxylic acid represented by the formula (XII) below is particularly preferable. The (thio) carboxylic acid represented by the formula (XII) below is a compound capable of forming, together with the compound represented by the formula (I), the molecular complex compound based on the interaction which satisfies the foregoing conditions (1) to (5).

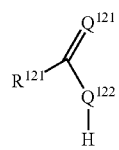

formula (XII)

In the formula (XII), $R^{121}$ represents a substituent; and $Q^{121}$ and $Q^{122}$ independently represents an oxygen atom or a sulfur atom. The substituent represented by $R^{121}$ may be the same as those represented by $R^{11}$ to $R^{13}$ in the formula (I), and also the specific and preferable examples thereof may be the same. The compound represented by the formula (XII) preferably has in the molecular thereof a substituent containing a $C_4$ or longer alkyl chain or oligoalkyleneoxy chain, a $C_2$ or longer perfluoroalkyl chain, perfluoroalkyl ether chain or organic polysilyl chain. Specific examples of such chain may be the same as that contained in the compound represented by the formula (I), and also the preferable range thereof may be the same.

In the formula (XII), the substituent represented by $R^{121}$ is preferably such that having a cyclic structure. The substituent having a cyclic structure preferably has an aryl group or aromatic heterocyclic group. The aryl group is preferably a phenyl, indenyl, a-naphthyl, β-naphthyl, fluorenyl, phenanthrenyl, anthracenyl and pyrenyl. Among these, phenyl and naphthyl are preferable. These aryl groups are preferably substituted with a substituent containing a $C_4$ or longer alkyl chain, oligoalkyleneoxy chain, $C_2$ or longer perfluoroalkyl chain, perfluoroalkylether chain, or organic polysilyl chain, and is further preferably substituted with two or more substituents containing above chains. Specific examples of these substituents containing such chains may be the same with those described in the above. In particular, the aryl group is preferably substituted with a substituent containing a $C_8$ or longer straight-chain or branched alkyl chain such as alkyl group (octyl, decyl, hexadecyl, 2-ethylhexyl, etc.), alkoxy group (dodecyloxy, hexadecyloxy, etc.), sulfide group (hexadecylthio, etc.), substituted amino group (heptadecylamino, etc.), octylcarbamoyl group, octanoyl group or decylsulfamoyl group. The aryl is further preferably substituted with two or more substituents containing a $C_8$ or longer straight-chain or branched alkyl chain. The aryl can be substituted with, halogen atom, hydroxyl, cyano, nitro, carboxyl, sulfo and so forth besides the foregoing substituents.

The aromatic heterocyclic group is preferably a five- to seven-membered heterocyclic group, more preferably a five- or six-membered group, and most preferably a six-membered group. Specific examples of such skeletons can be found in heterocycles listed in "Iwanami Rikagaku Jiten (Iwanami's Physicochemical Dictionary; Iwanami Shoten, Publishers), the 3rd edition, supplement Chapter 11 "Nomenclature for Organic Chemistry", Table 4 "Names of Principal Hetero Monocyclic Compounds" on page 1606, and Table 5 "Names of Principal Condensed Heterocyclic Compounds" on page 1607. The foregoing aromatic heterocyclic groups are, similarly to the foregoing aryl group, preferably substituted with a substituent containing a $C_4$ or longer alkyl chain or oligoalkyleneoxy chain, a $C_2$ or longer perfluoroalkyl chain, perfluoroalkyl ether chain or organic polysilyl chain, where substitution by two or more chains is more preferable. Specific examples of the substituent containing such chain are same as those described in the above. The aromatic heterocyclic group may also be substituted by halogen atom, hydroxyl, cyano, nitro, carboxyl, sulfo or the like, besides the foregoing substituents.

A compound capable of forming a complex compound with the compound represented by the formula (I) may be a low-molecular-weight compound or high-molecular-weight compound. The molecular complex compound may also be composed of a compound represented by the formula (I) and two or more other compounds.

Requirements for forming the complex compound described in the above clearly show preference of planar bond formation and of molecule having a planar, that is, cyclic substituent. Such features are advantageous not only in that forming the complex compound, but also in that promoting interaction on the friction sliding surface, that is, effectively covering such friction sliding surface. The friction sliding surface is generally composed of an inorganic material, and more specifically, metal, metal oxide thin film formed by oxidation thereof, or ceramic, on which polar electrostatic interaction is predominant, which is stronger than van der Waals force known as a general interaction between organic substances. Now organic compounds capable of exhibiting a strong interaction with such surface will be discussed in view of the foregoing conditions (1) to (5) (assuming the sliding surface as s, and an organic compound covering thereof as ρ). In view of the condition (1), a planar structure is advantageous. In view of the condition (2), the molecules must have sites responsible for electrostatic interaction stronger than van der Waals force, in such context polar bond such as hydrogen bond is suitable for a polar sliding surface. In view of the condition (3), a planar structure is advantageous. In view of the condition (4), the complex compound containing triarylmelamine will give a great advantage since the complementary atomic group of triarylmelamine is equivalent as viewed from three directions, and thus possibly forms a complex compound not only by two molecules but also by three or more molecules. So that it is apparent that the complex composition of the present invention is suitable for establishing a strong interaction with the sliding surface also in view of the condition (5). It is supposed that such factors make it possible to attain an extremely high wear-resistance even through the coverage is achieved only by such molecular complex composition.

The molecular complex compound having a non-polar or hydrophobic group will be more advantageous in that preventing the sliding surfaces of the both from contacting with each other, and in that relieving stress. The non-polar or hydrophobic group can be exemplified by long-chain alkyl group, perfluoroalkyl group, oligoalkoxy group, perfluoroalkylether group and organic polysiloxane group. These hydrophobic groups having a non-polar property will orientate so as to be repulsed from the polar sliding surface to thereby achieve energy stabilization. Introducing such hydrophobic group into an appropriate site of the compound represented by the formula (I) which composes the molecular complex compound (or other compound composing some others) typically allows provision of a lubricant capable of being oriented on the sliding surface as shown in FIG. 1. On the sliding surface, the lubricant capable of being oriented as shown in FIG. 1 is supposed to exhibit an extremely small friction coefficient.

Substances which can exhibit strong inter-molecular interaction generally suffer from poor handling property due to their high crystallinity, high melting point, poor solubility and poor dispersion property. Introducing now a hydrophobic group can improve the solubility and dispersion property of the molecular complex compound into a lubricant base oil, and can also improve the handling property through reducing its crystallinity. Such introduction will be most advantageous even for the case the molecular complex compound is used without being mixed with any lubricant base oil, since the molecular complex compound will have an excellent film forming property on the sliding surface, and particularly since it can maintain a low viscosity under low temperatures.

Whether the compound represented by the formula (I) forms the molecular complex compound or not can be determined typically by analyzing the crystal, if it is available, so as to confirm presence of such complex compound. Even for the case the crystal is not available, formation of the complex compound is presumed if the inter-molecular force (free energy of bond), including salvation, ascribable to formation of the complex compound between the compound ρ represented by the formula (I) and the compound s having a functional group which is capable of interacting with ρ is almost equivalent to or smaller than free energy of bond ascribable to independent solvation of ρ and s. The formation of the complex compound can also be estimated by comparing the individual thermal-phase-transfer temperature patterns for ρ and s with those obtained for mixtures of ρ and s mixed in stoichiometric integer ratios, and by finding any specific thermal property which apparently differs from the individual thermal-phase-transfer temperature patterns for ρ and s. The compounds ρ and s merely kept in a mixed status without any interaction therebetween will simply show shifting of a peak of the phase transfer temperature depending on the mixing ratio thereof such as found in freezing point depression. On the other hand, most of the cases in which ρ and s are kept in a complex forming status show another thermal transfer peak in a new temperature range. It is still also possible to confirm formation of the complex compound by comparing the individual FT-IR spectra for the complex compounds ρ and s, and thus confirming any shifting of the vibration absorption peak ascribable to the functional group responsible for such interaction.

The following paragraphs will describe specific examples of the molecular complex compound which contains the compound represented by the formula (I) and is based on a combination satisfying the foregoing conditions (1) to (5). It is to be noted, however, the present invention is by no means limited by such examples.

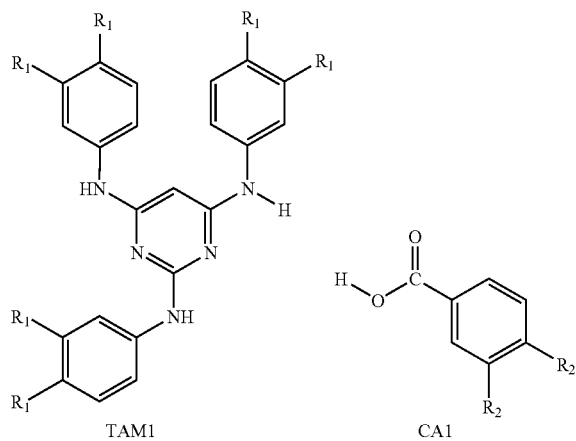

a-1

$R_1 = OC_{12}H_{25}$ $R_2 = OC_{12}H_{25}$

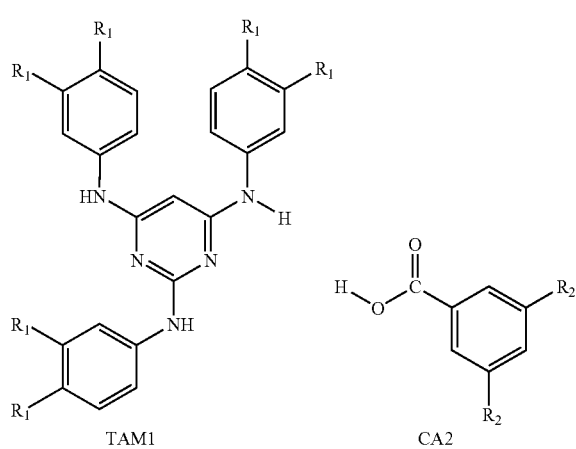

a-2

$R_1 = OC_{12}H_{25}$ $R_2 = OC_{12}H_{25}$

-continued
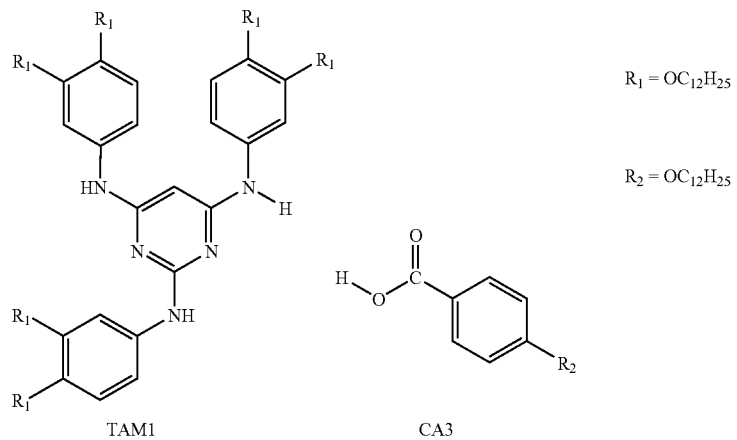
a-3
$R_1 = OC_{12}H_{25}$
$R_2 = OC_{12}H_{25}$
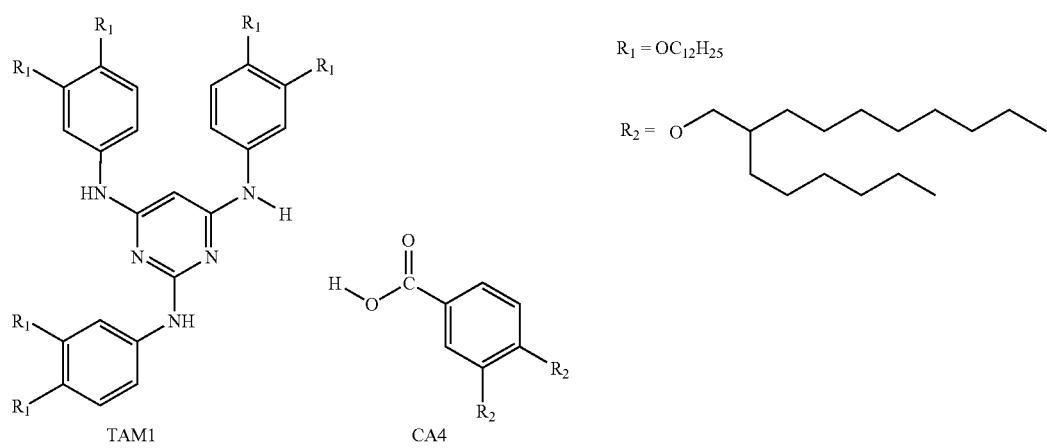
a-4
$R_1 = OC_{12}H_{25}$
$R_2 = $ 
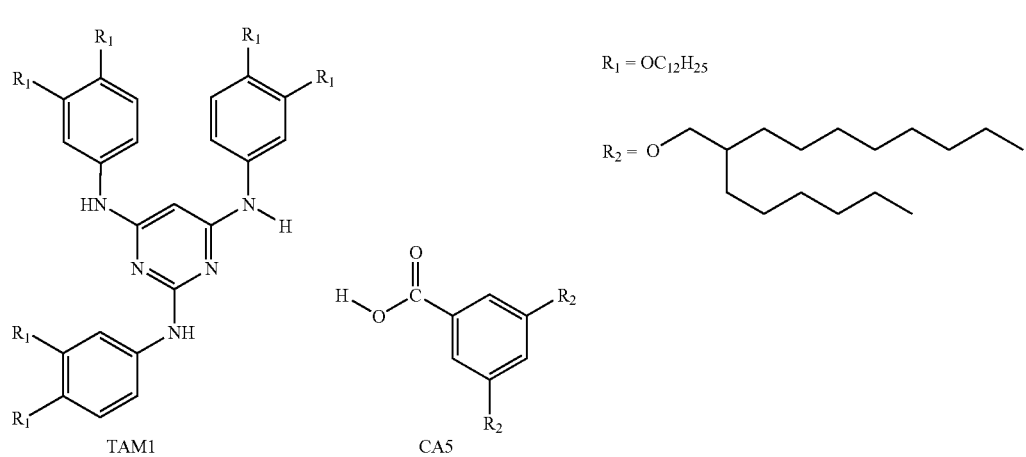
a-5
$R_1 = OC_{12}H_{25}$
$R_2 = $ -continued
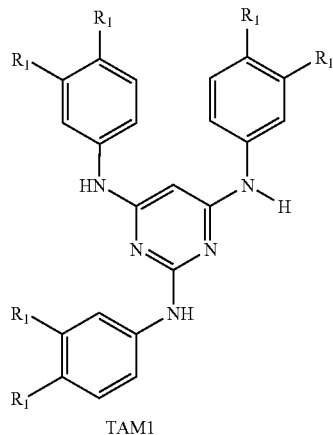
TAM1
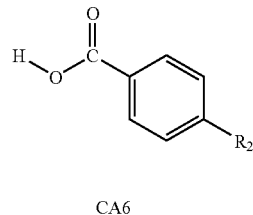
CA6
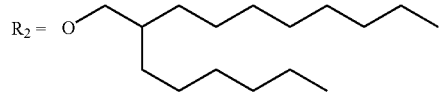
a-6
$R_1 = OC_{12}H_{25}$
$R_2 =$
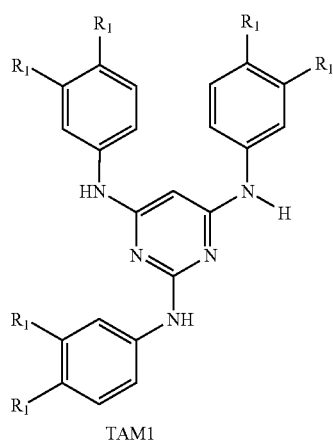
TAM1
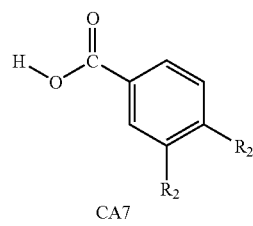
CA7
a-7
$R_1 = OC_{12}H_{25}$
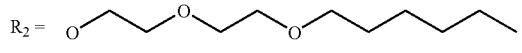
$R_2 =$
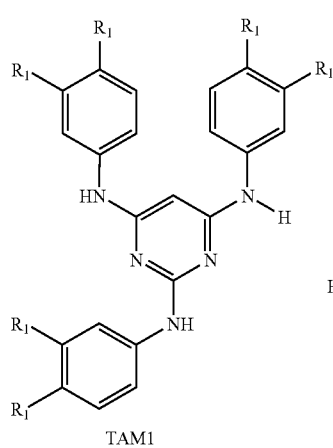
TAM1
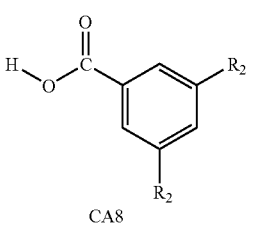
CA8
a-8
$R_1 = OC_{12}H_{25}$
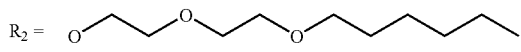
$R_2 =$ -continued
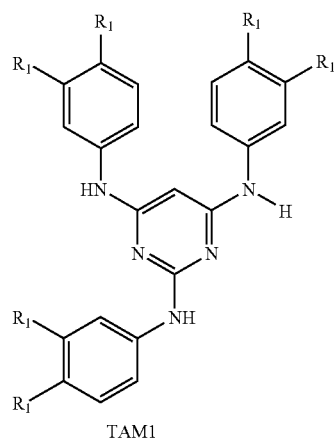
TAM1
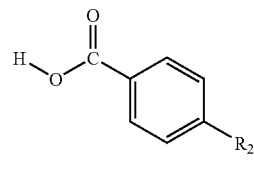
CA9
a-9
$R_1 = OC_{12}H_{25}$
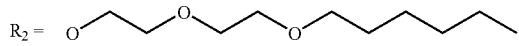
$R_2 =$
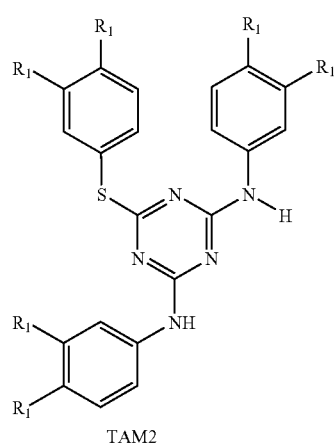
TAM2
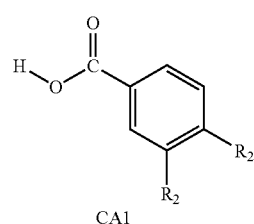
CA1
a-10
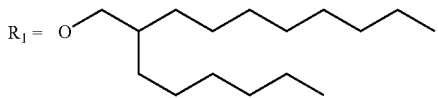
$R_1 =$
$R_2 = OC_{12}H_{25}$
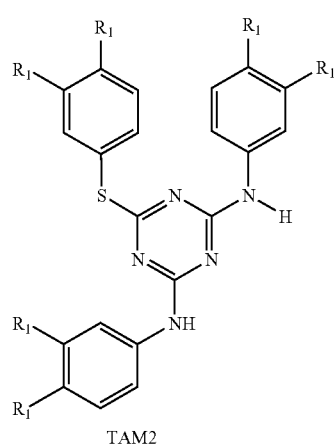
TAM2
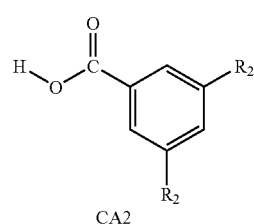
CA2
a-11
$R_1 =$
$R_2 = OC_{12}H_{25}$ -continued
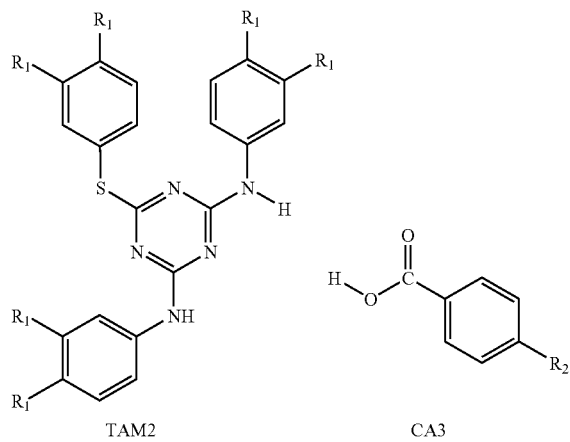
TAM2  CA3
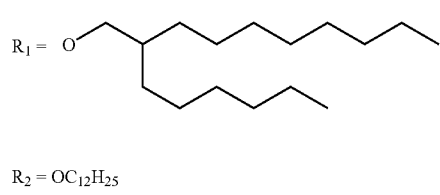
a-12
$R_2 = OC_{12}H_{25}$
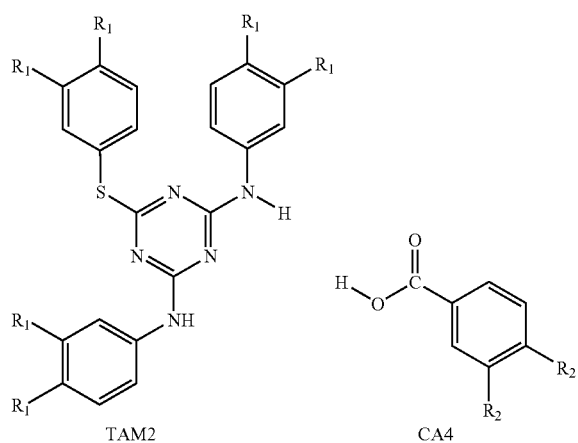
TAM2  CA4
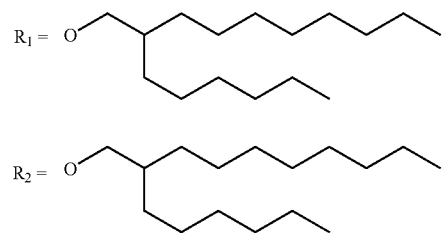
a-13
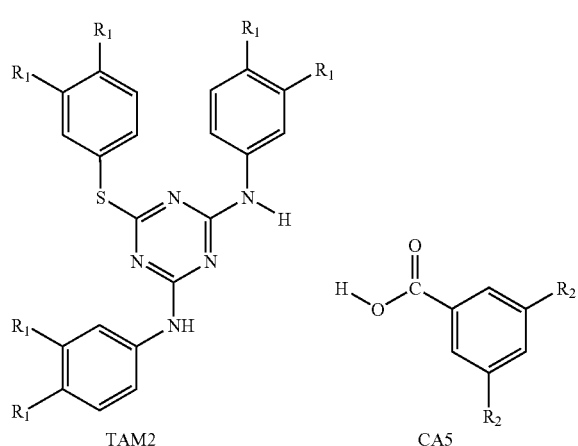
TAM2  CA5
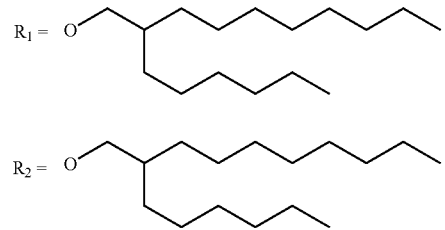
a-14

-continued
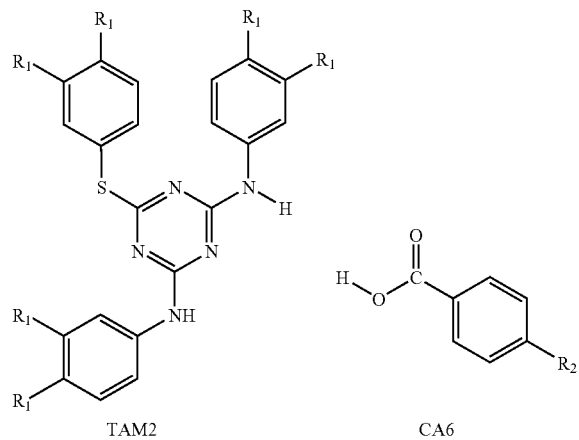
TAM2      CA6
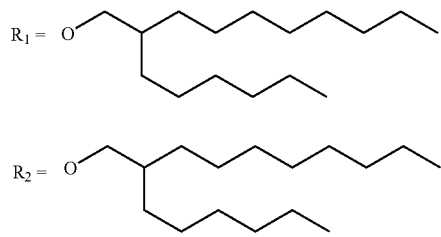
a-15
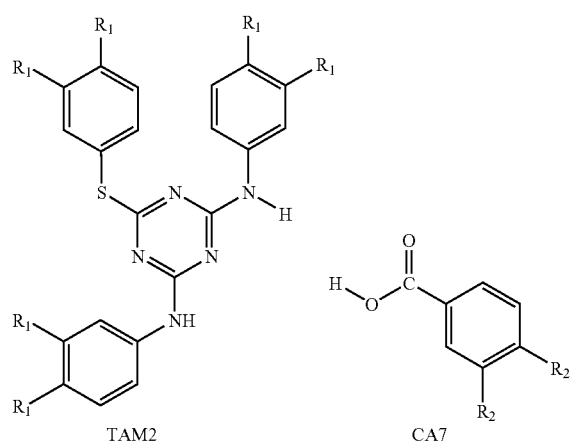
TAM2      CA7
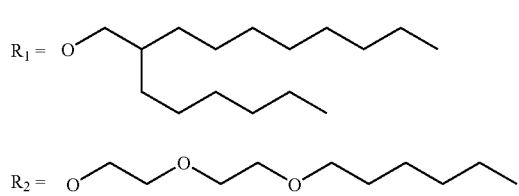
a-16
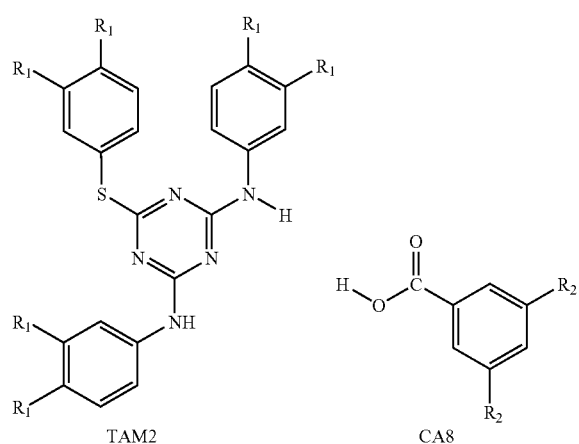
TAM2      CA8
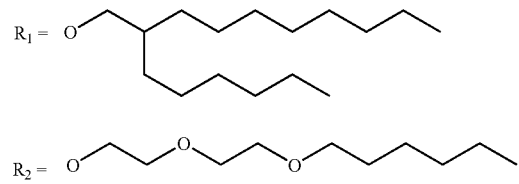
a-17

-continued
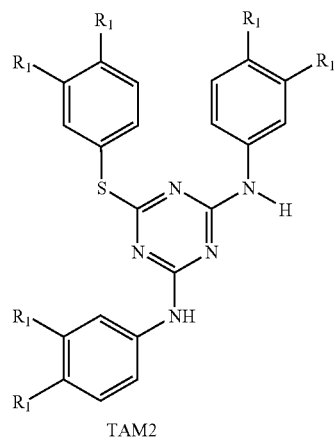
TAM2
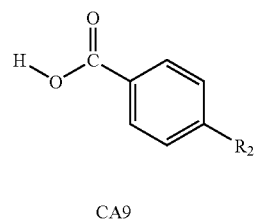
CA9
a-18
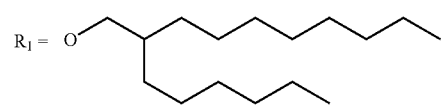
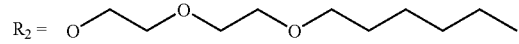
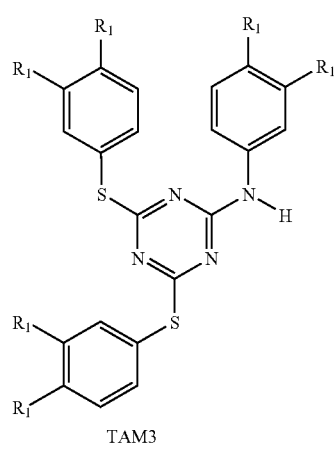
TAM3
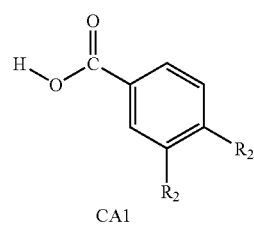
CA1
a-19
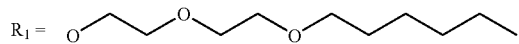
$R_2 = OC_{12}H_{25}$
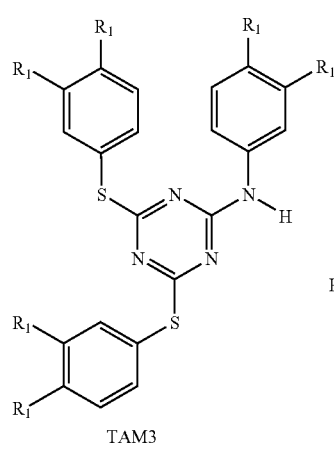
TAM3
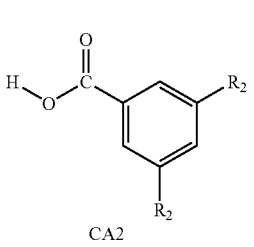
CA2
a-20
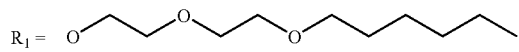
$R_2 = OC_{12}H_{25}$ -continued
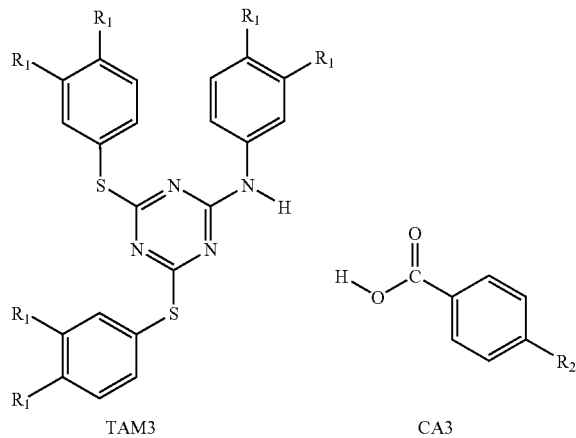
TAM3      CA3
a-21
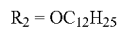
$R_2 = OC_{12}H_{25}$
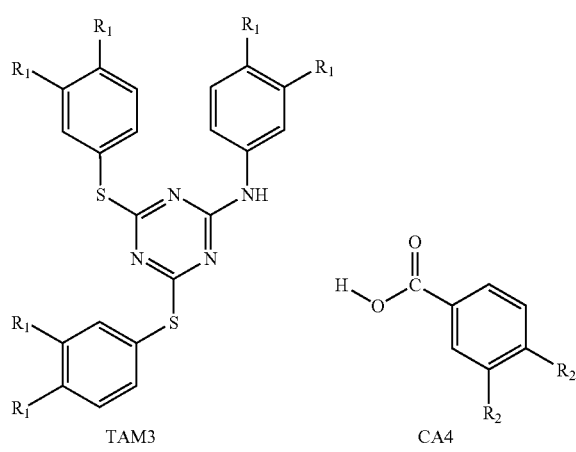
TAM3      CA4
a-22
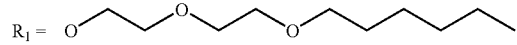
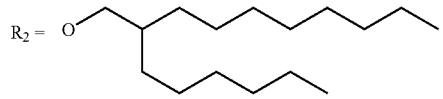
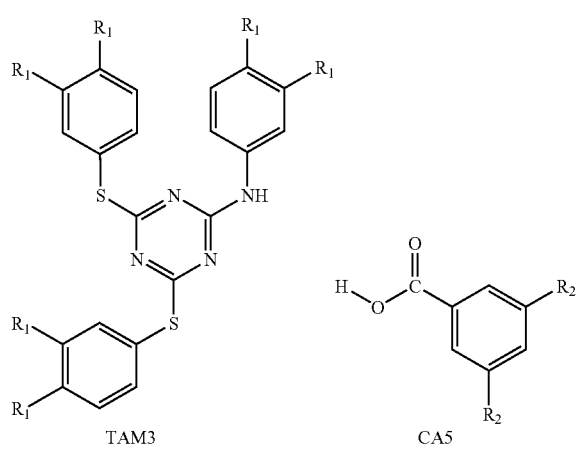
TAM3      CA5
a-23
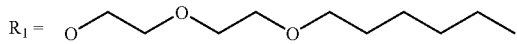
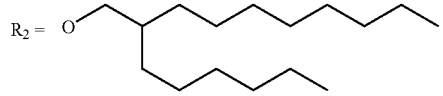

-continued
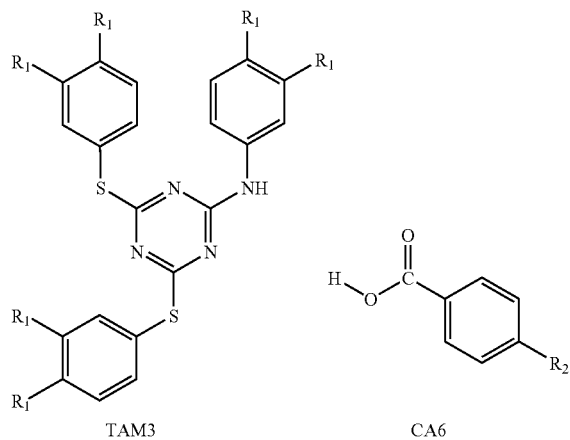 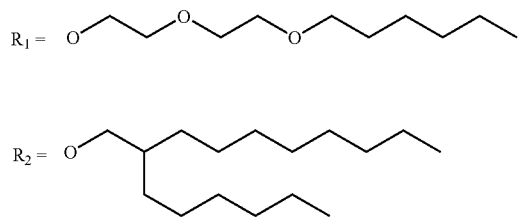
a-24
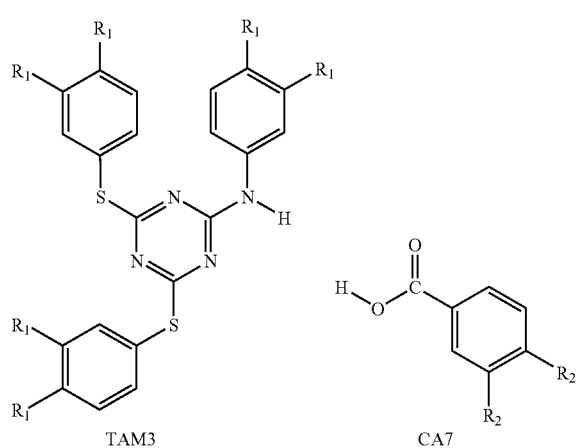 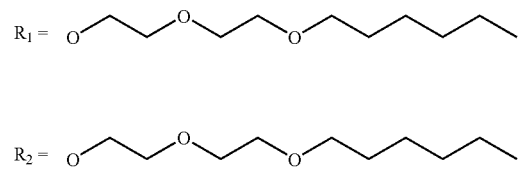
a-25
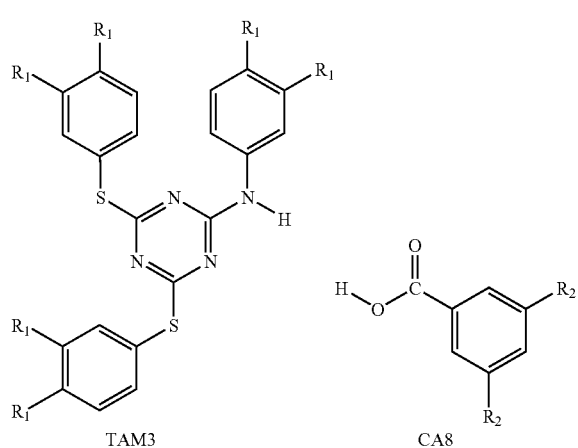 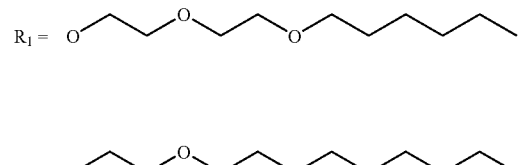
a-26

-continued
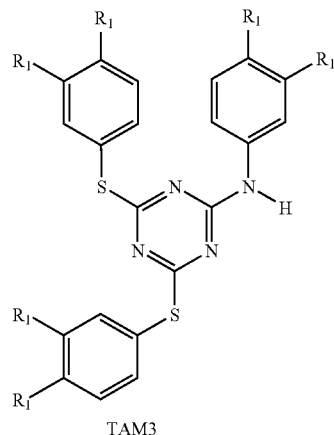 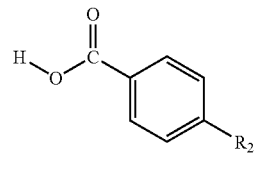
TAM3  CA9
a-27
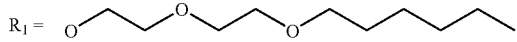
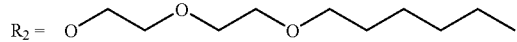
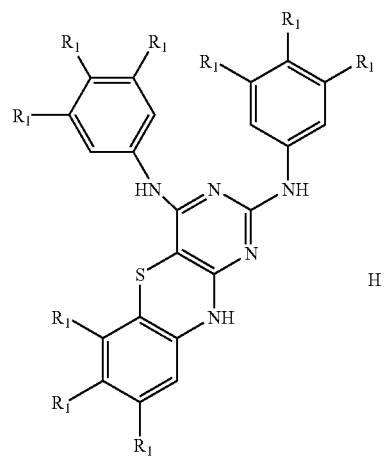 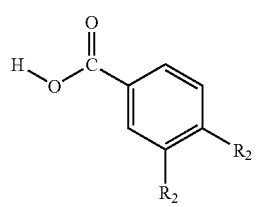
TAM4  CA4
a-28
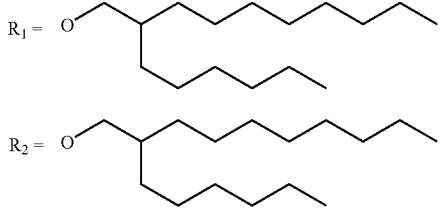
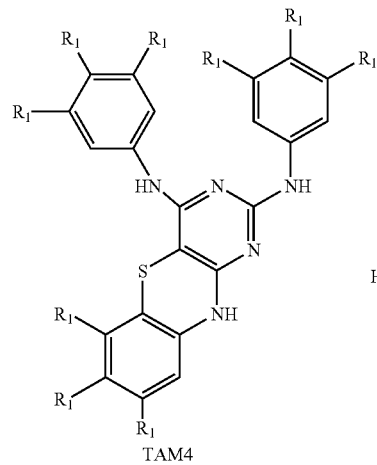 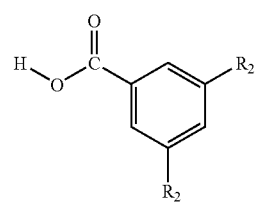
TAM4  CA5
a-29
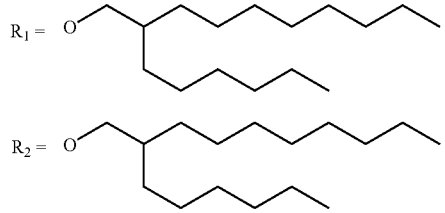

-continued
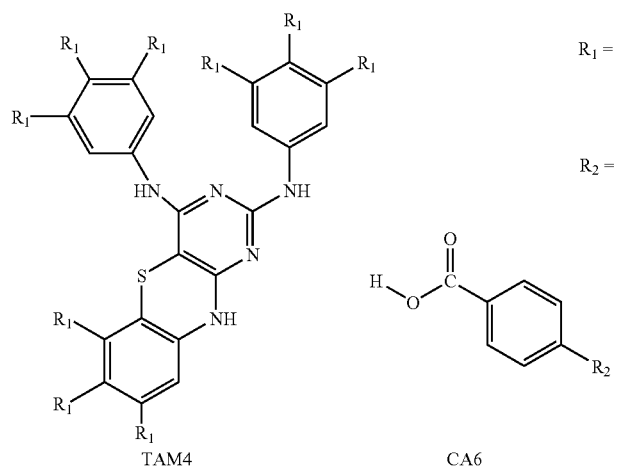
TAM4
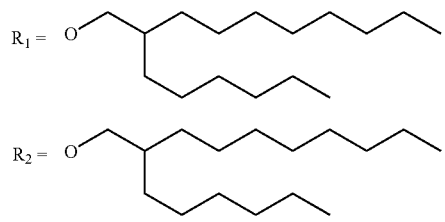
CA6
a-30
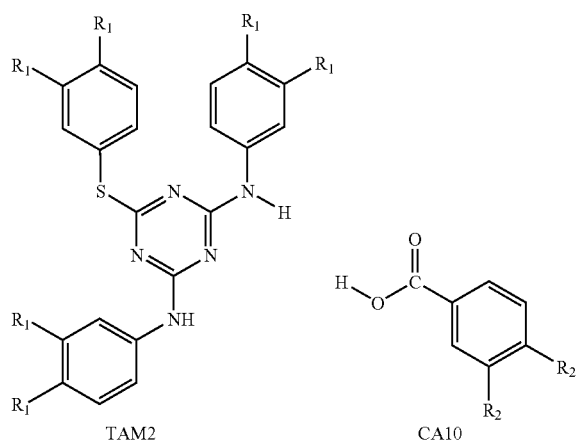
TAM2
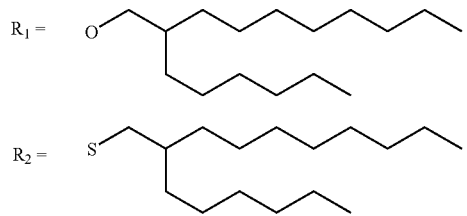
CA10
a-31
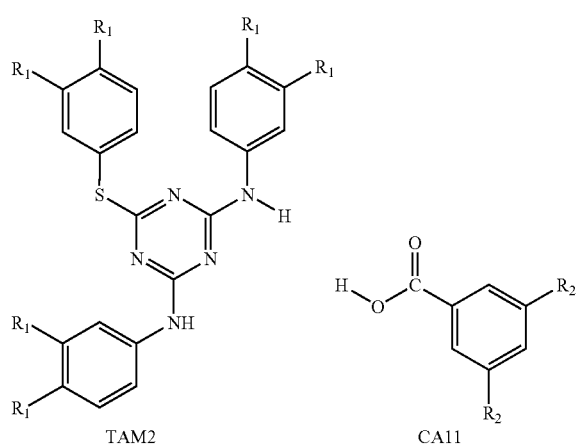
TAM2
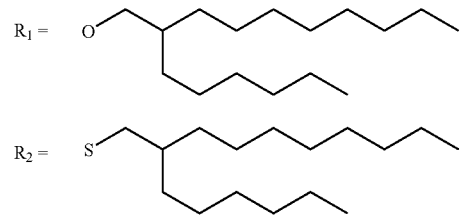
CA11
a-32

-continued
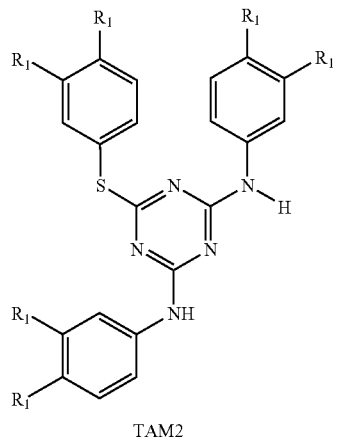
TAM2
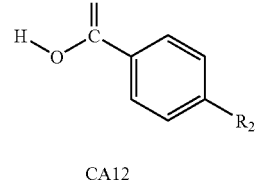
CA12
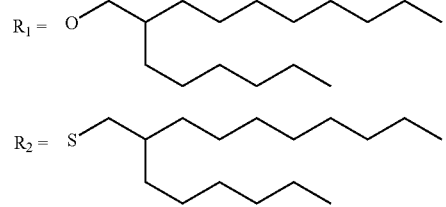
a-33
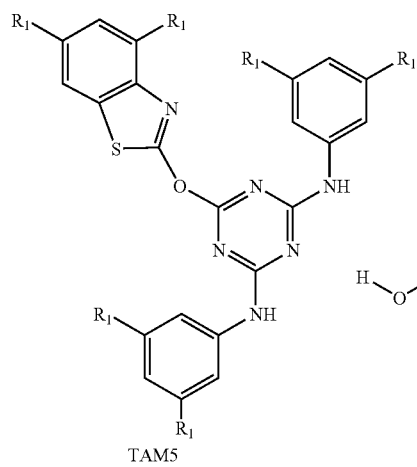
TAM5
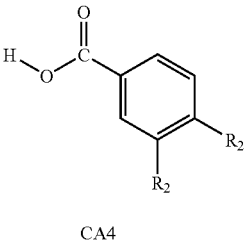
CA4
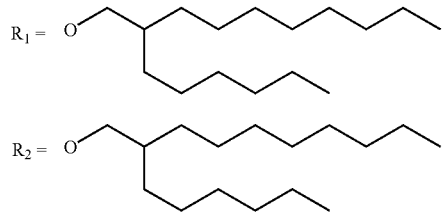
a-34
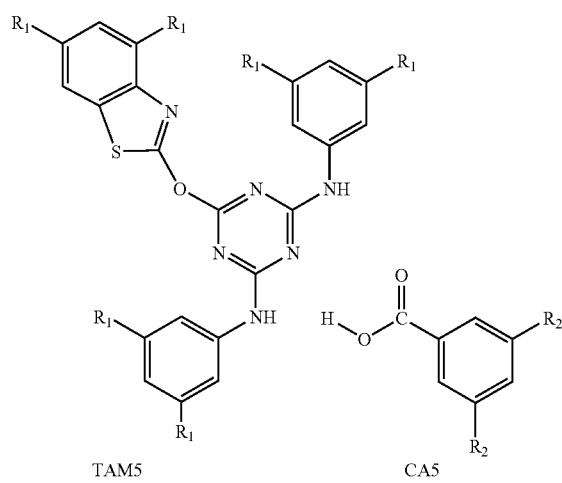
TAM5
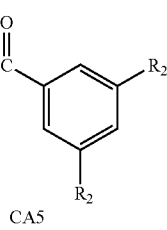
CA5
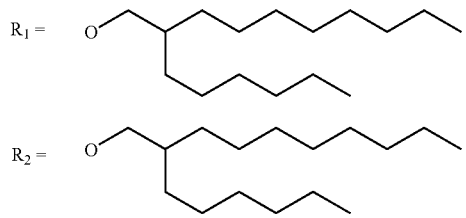
a-35

-continued
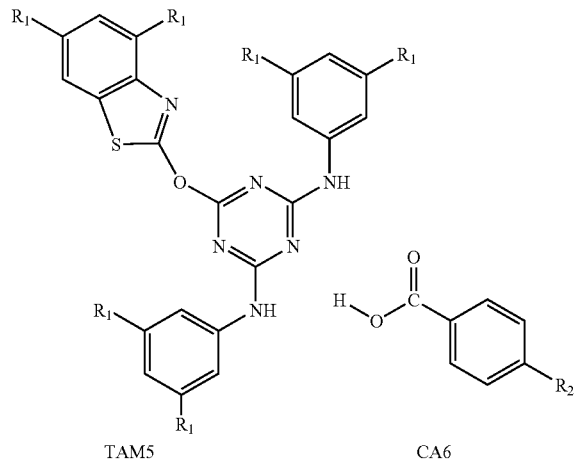
TAM5   CA6
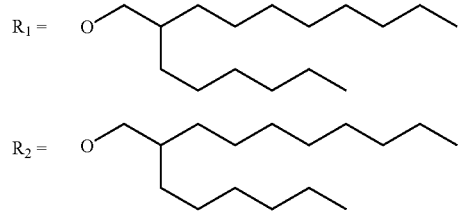
a-36
$R_1 =$ 
$R_2 =$ 
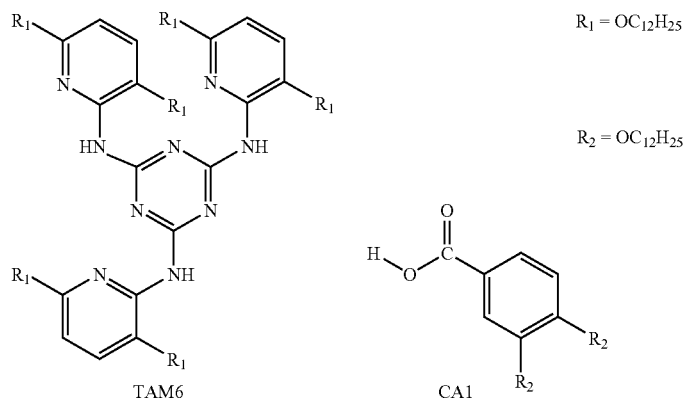
TAM6   CA1
a-37
$R_1 = OC_{12}H_{25}$
$R_2 = OC_{12}H_{25}$
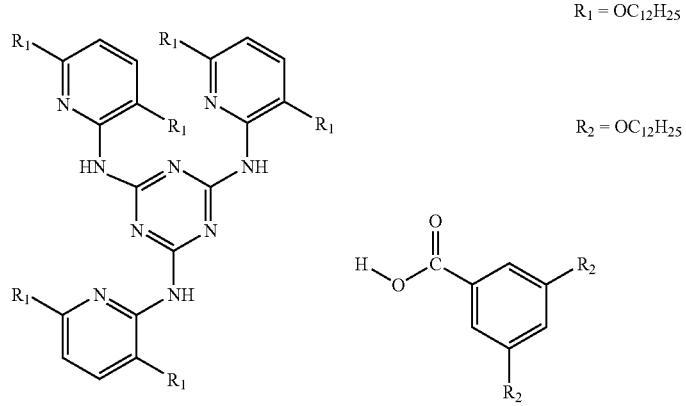
TAM6   CA2
a-38
$R_1 = OC_{12}H_{25}$
$R_2 = OC_{12}H_{25}$ -continued
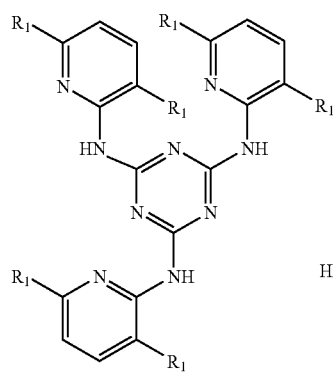
TAM6
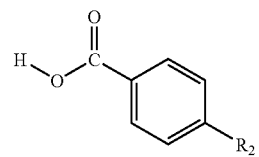
CA3
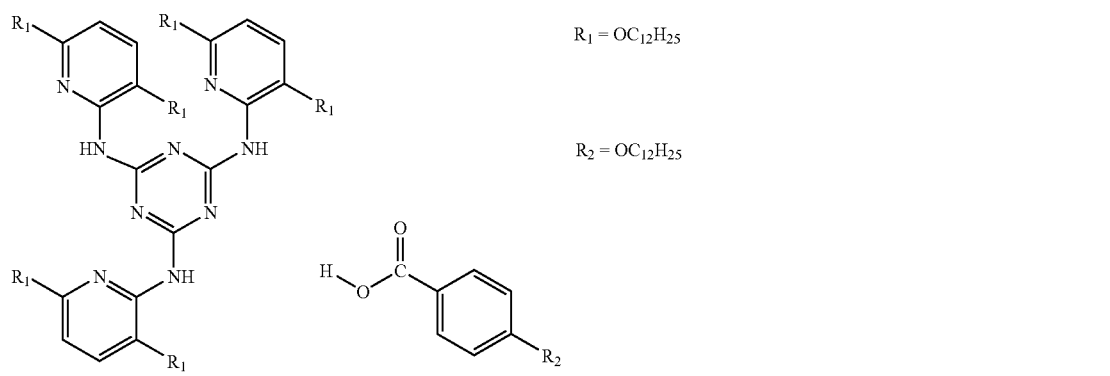
a-39
R$_1$ = OC$_{12}$H$_{25}$
R$_2$ = OC$_{12}$H$_{25}$
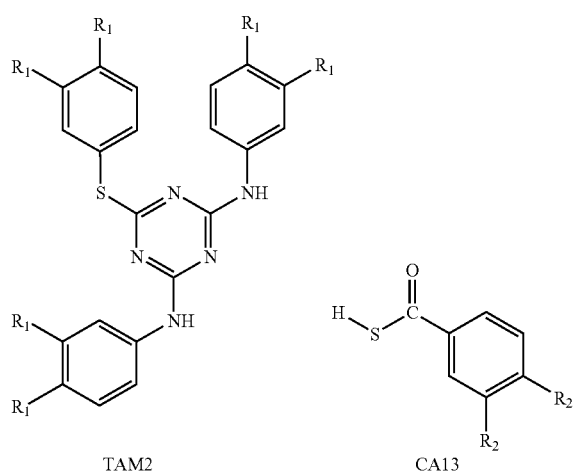
TAM2
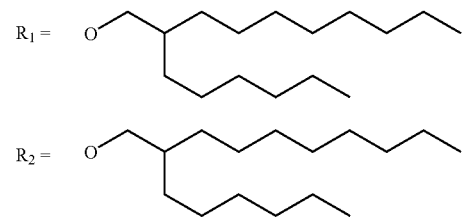
CA13
a-40
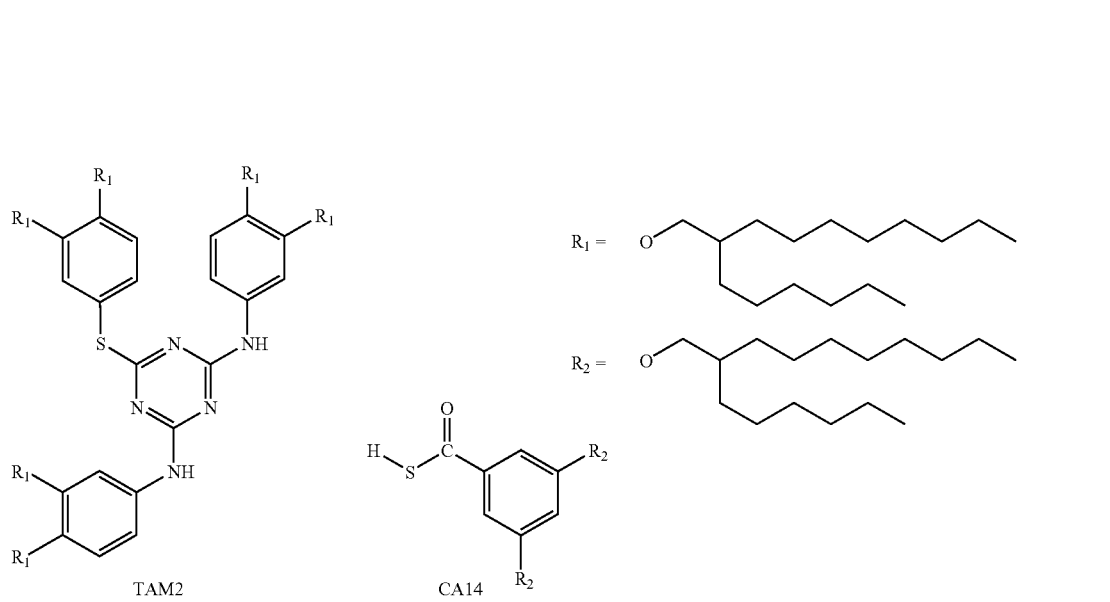
TAM2
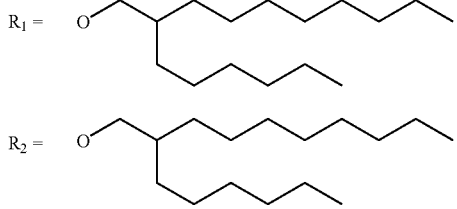
CA14
a-41

-continued
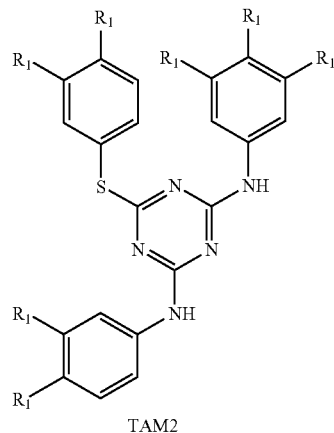
TAM2
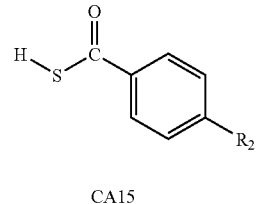
CA15
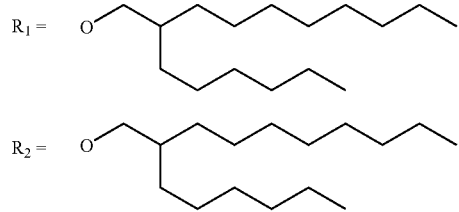
a-42
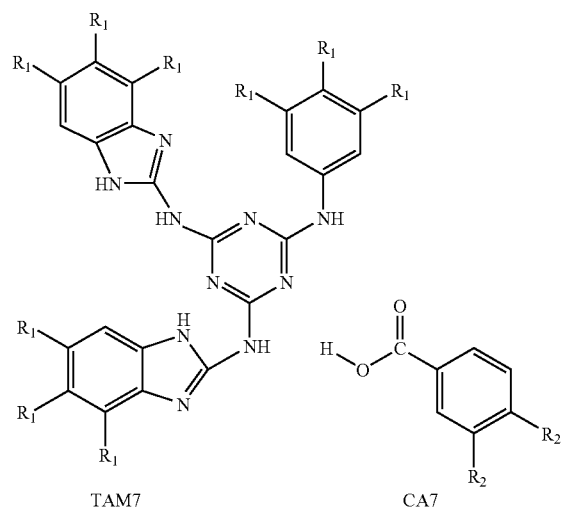
TAM7
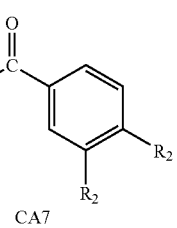
CA7
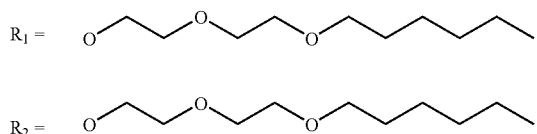
a-43
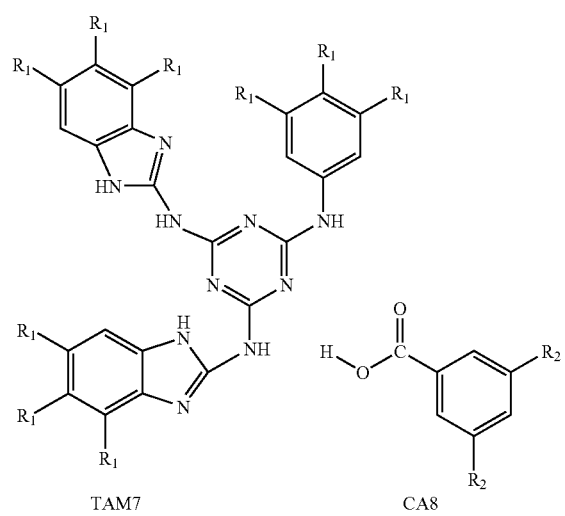
TAM7
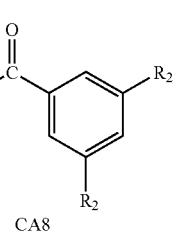
CA8
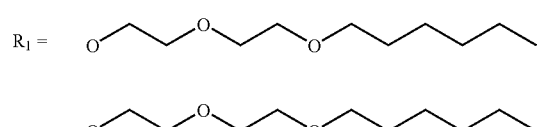
a-44

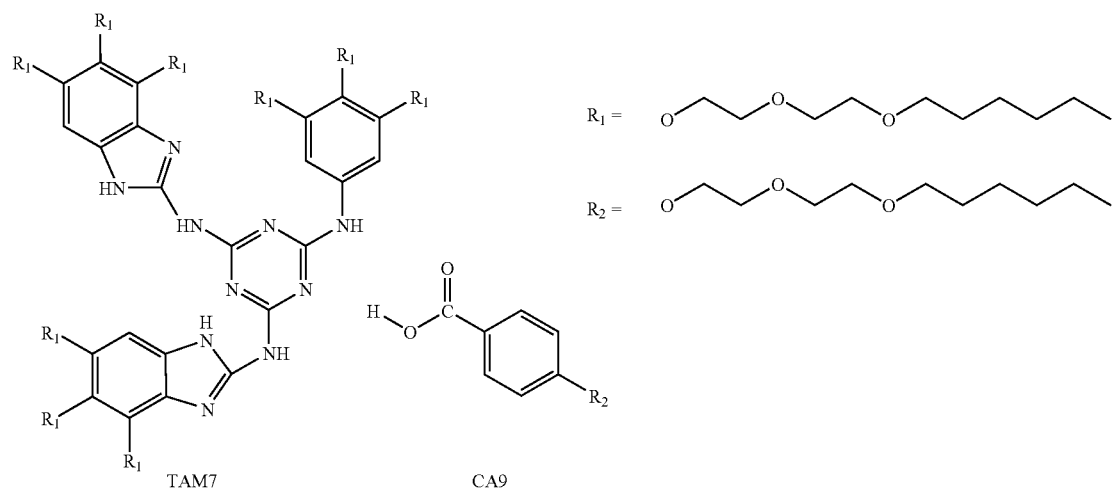
a-45
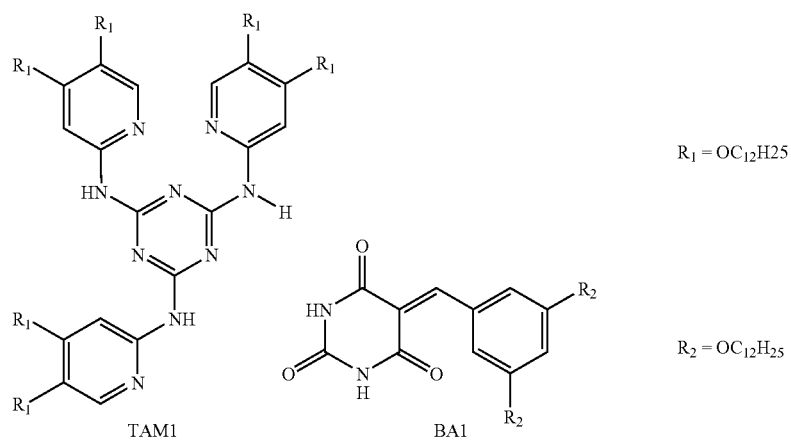
a-46
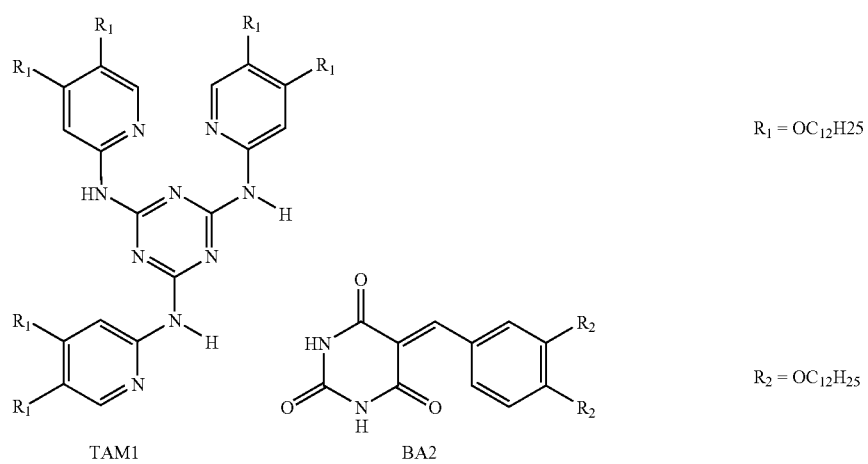
a-47

-continued
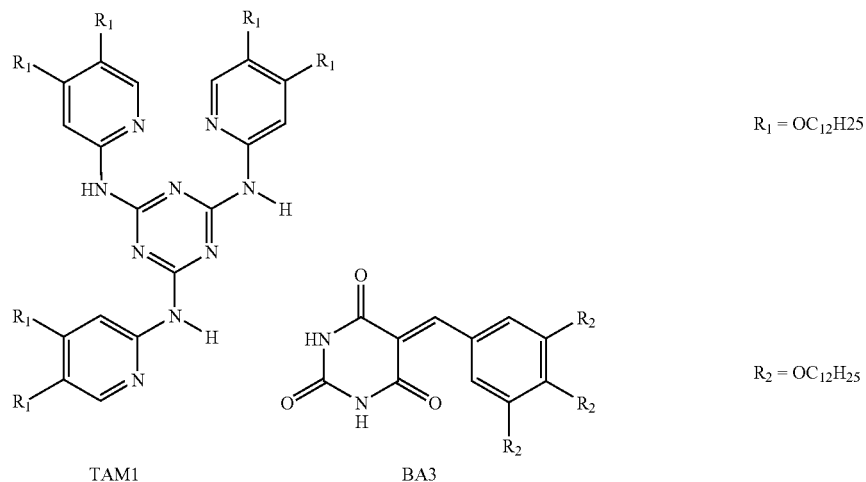
a-48
R₁ = OC₁₂H₂₅
R₂ = OC₁₂H₂₅
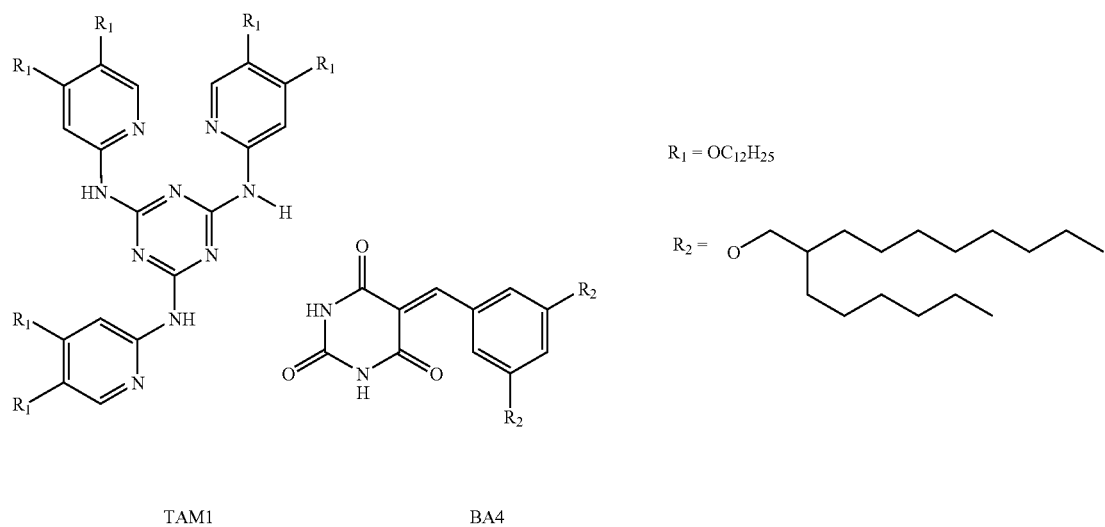
a-49
R₁ = OC₁₂H₂₅
R₂ = O-CH₂-CH(C₆H₁₃)-C₈H₁₇
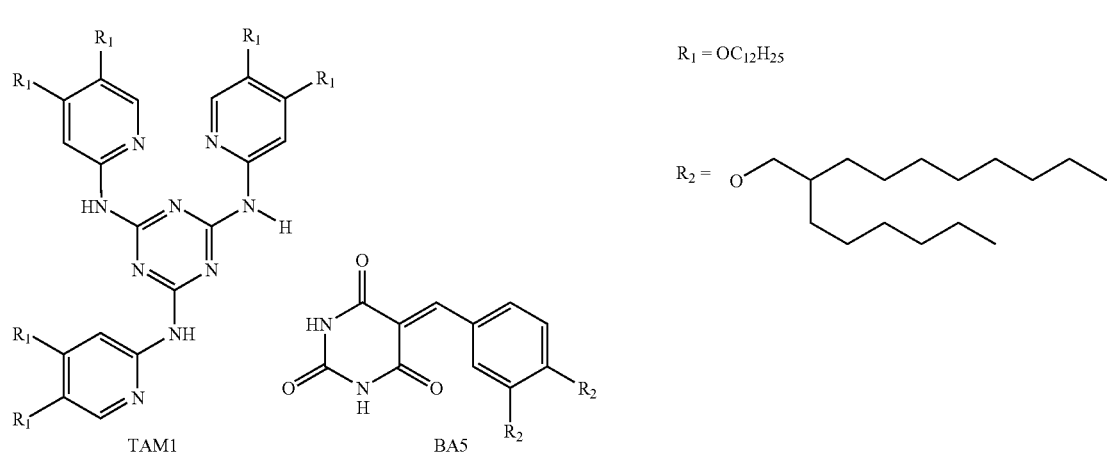
a-50
R₁ = OC₁₂H₂₅
R₂ = O-CH₂-CH(C₆H₁₃)-C₈H₁₇

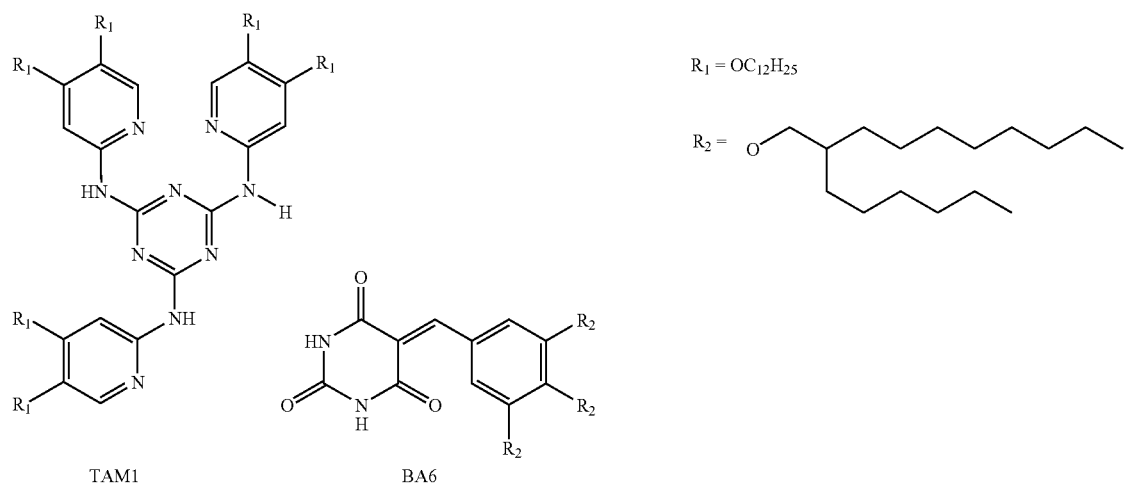
a-51
R₁ = OC₁₂H₂₅
R₂ =
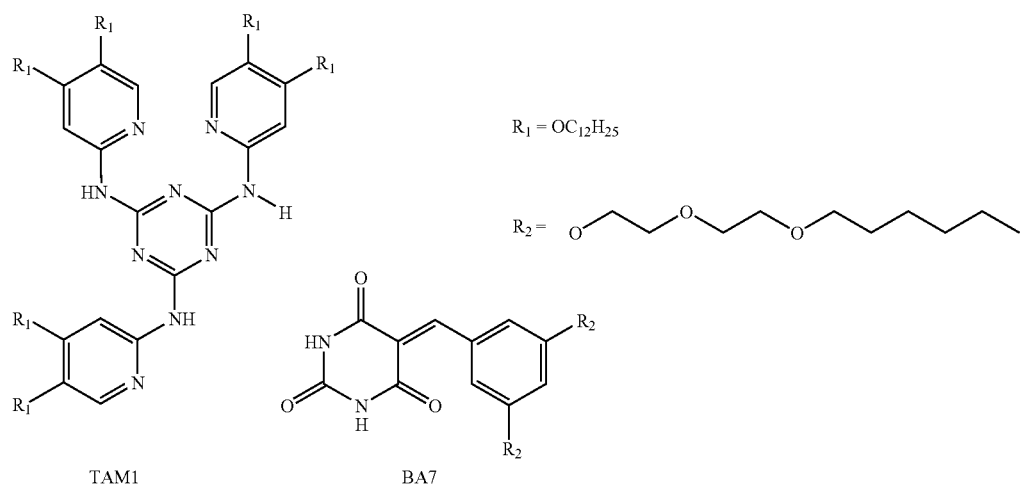
a-52
R₁ = OC₁₂H₂₅
R₂ =
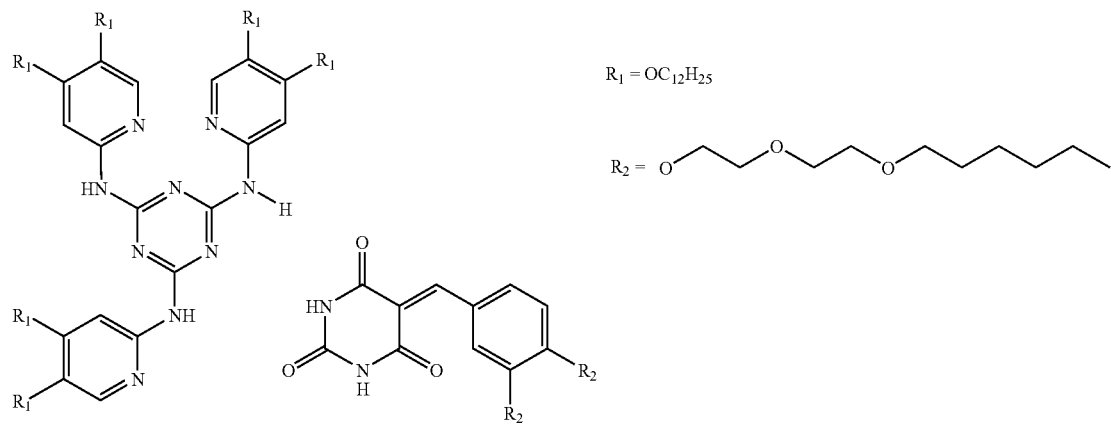
a-53
R₁ = OC₁₂H₂₅
R₂ =

-continued
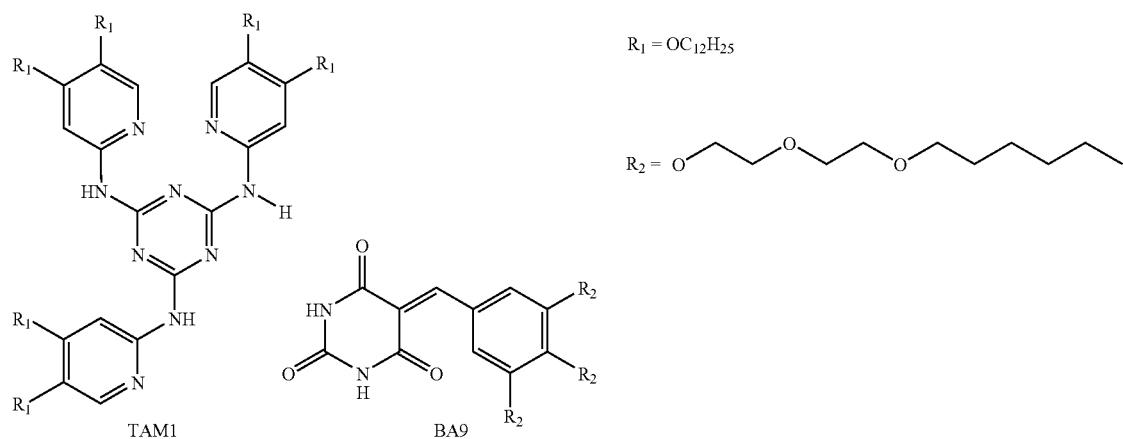
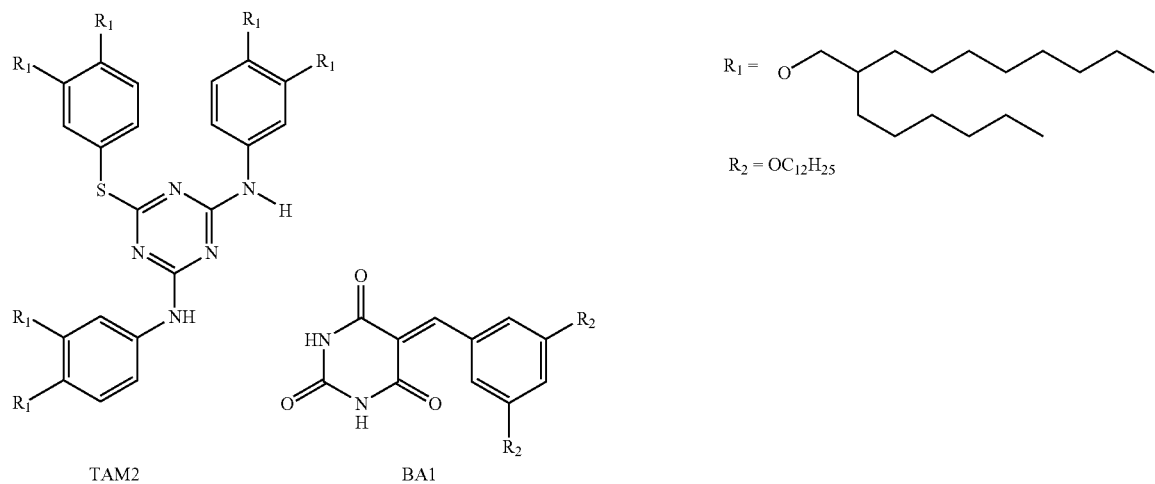
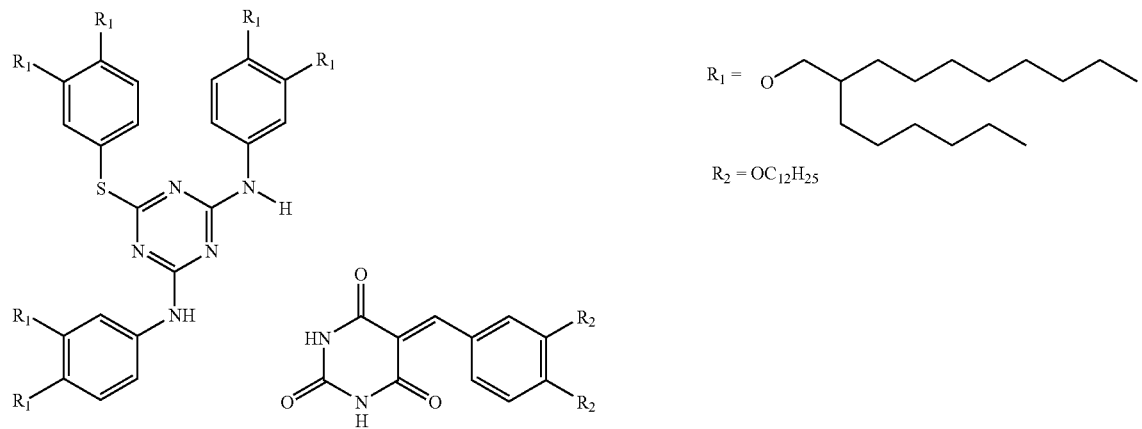

-continued
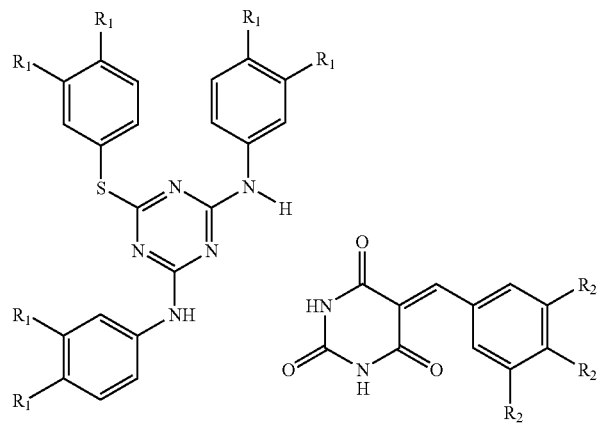
TAM2    BA3
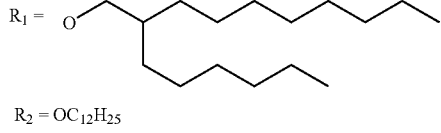
a-57
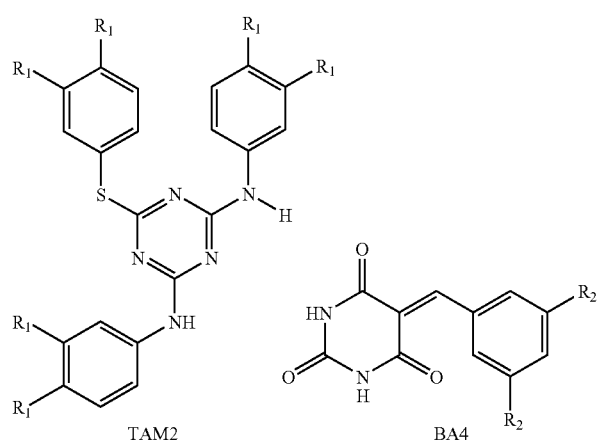
TAM2    BA4
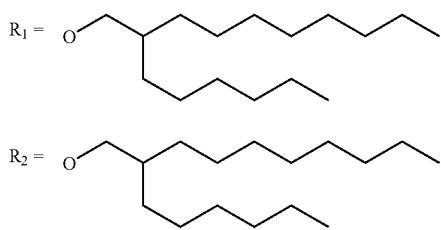
a-58
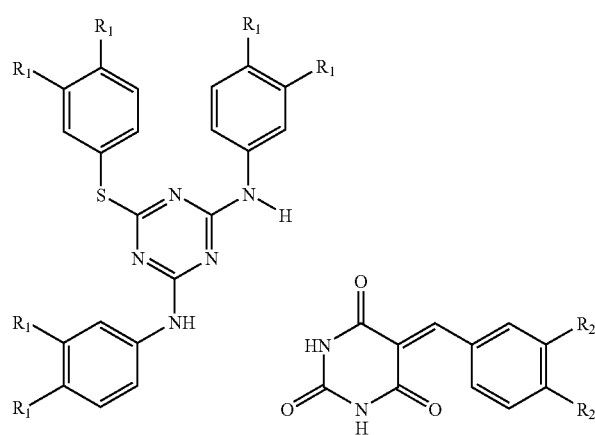
TAM2    BA5
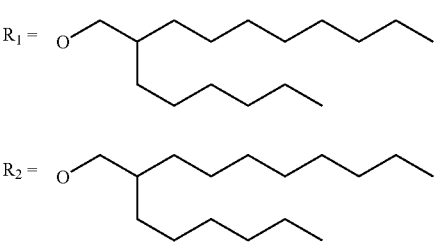
a-59

-continued
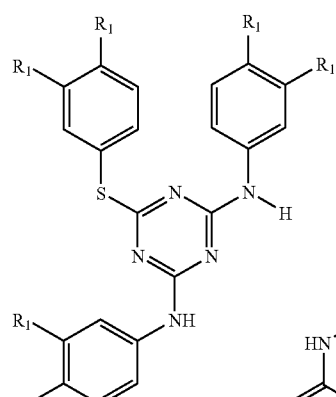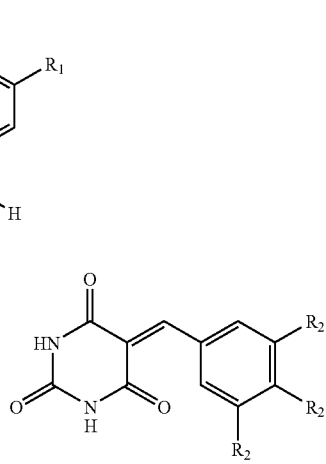
TAM2        BA6
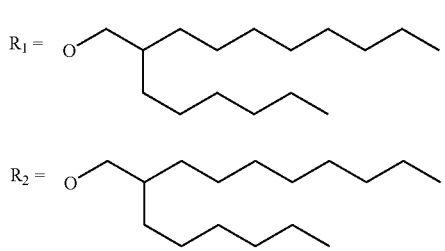
a-60
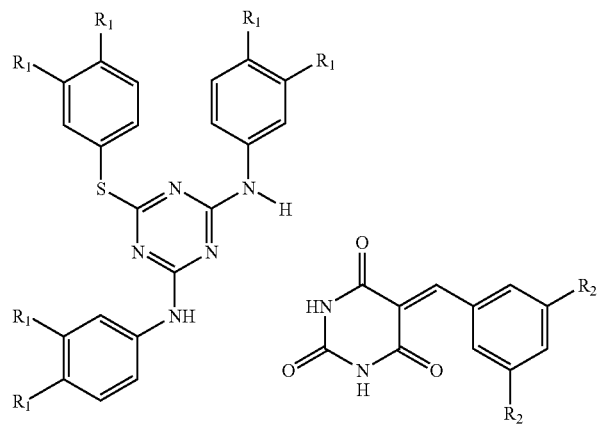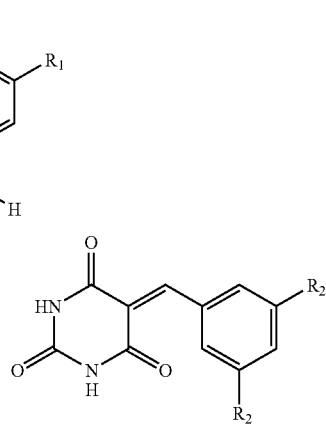
TAM2        BA7
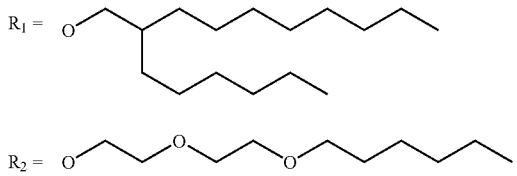
a-61
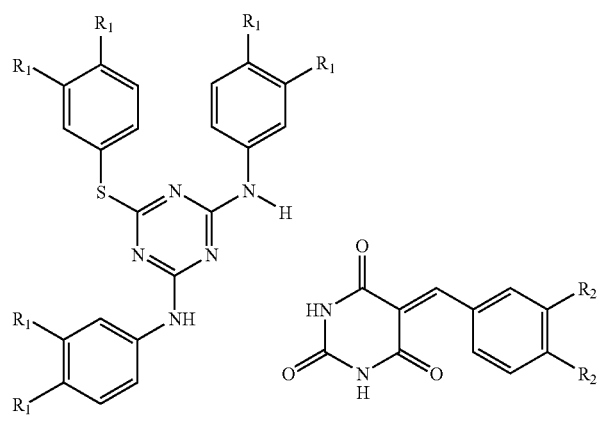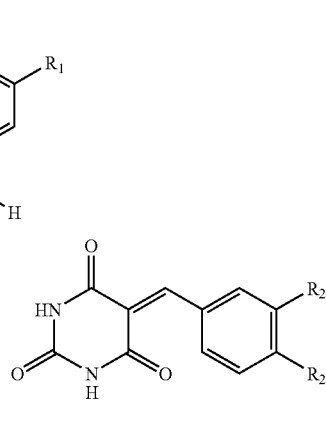
TAM2        BA8
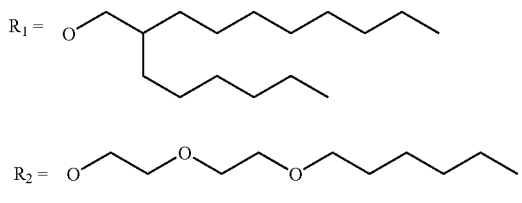
a-62

-continued
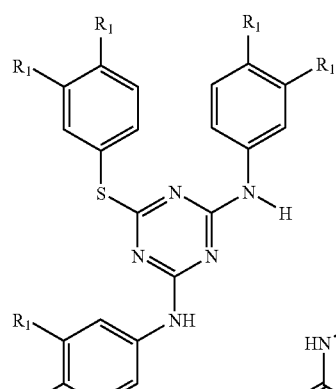
TAM2
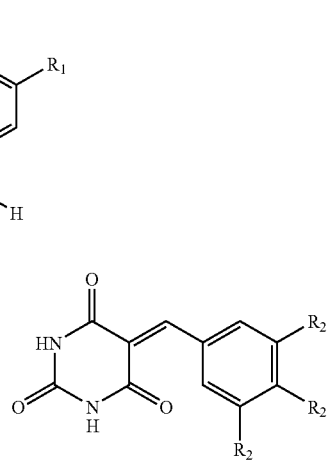
BA9
a-63
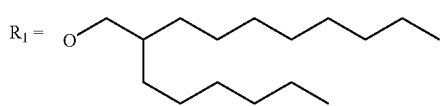
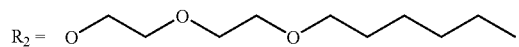
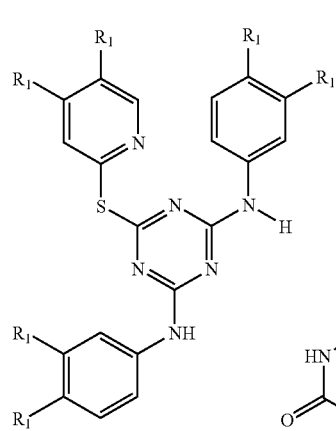
TAM3
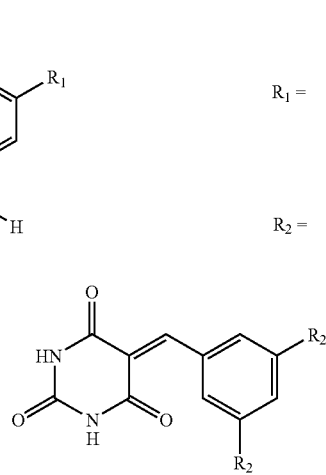
BA1
a-64
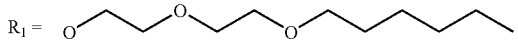
$R_2 = $ 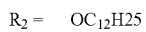 $OC_{12}H_{25}$
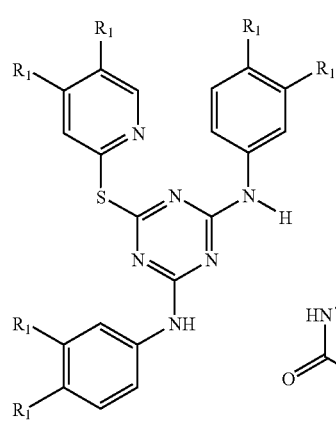
TAM3
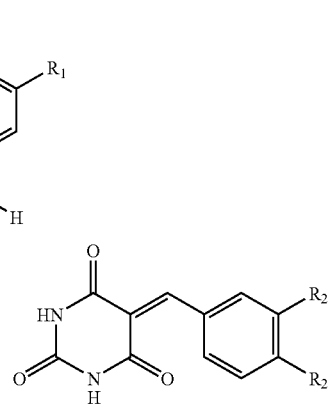
BA2
a-65
$R_1 = $ (same diethylene glycol hexyl ether group as above)
$R_2 = OC_{12}H_{25}$ -continued
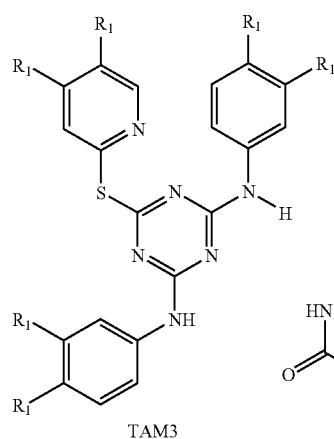 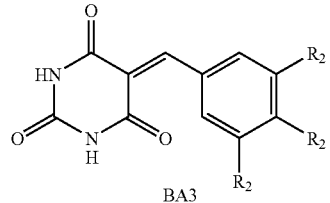
a-66
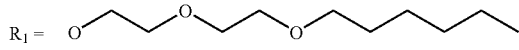
$R_2 = OC_{12}H_{25}$
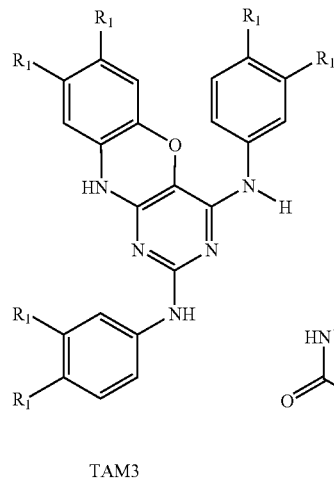 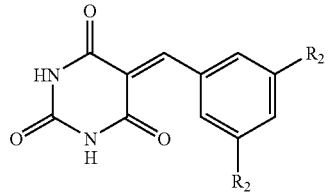
a-67
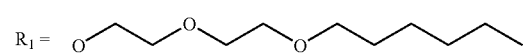
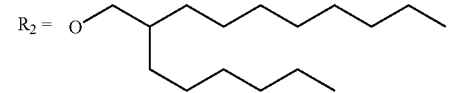
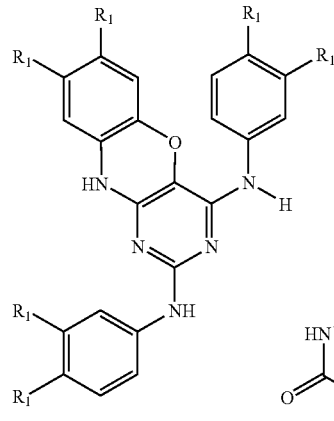 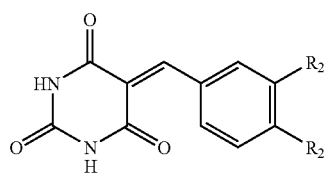
a-68
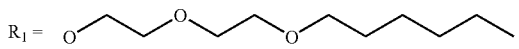
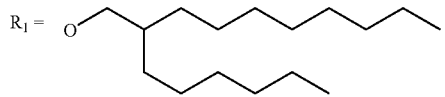

-continued
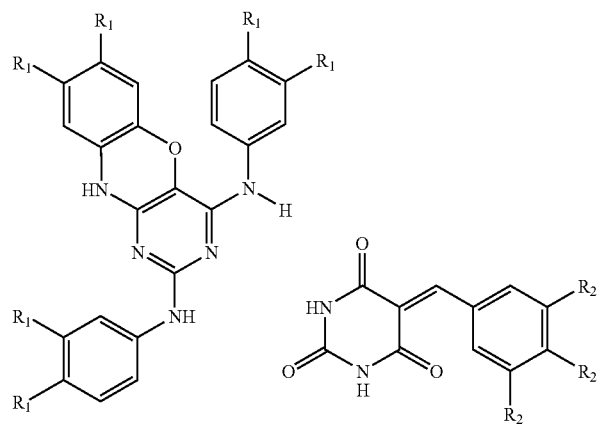
TAM3    BA6
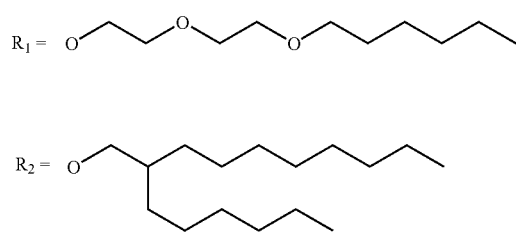
a-69
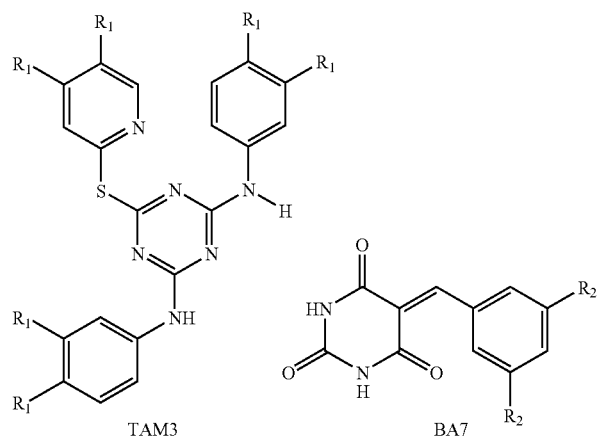
TAM3    BA7
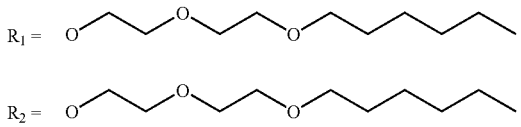
a-70
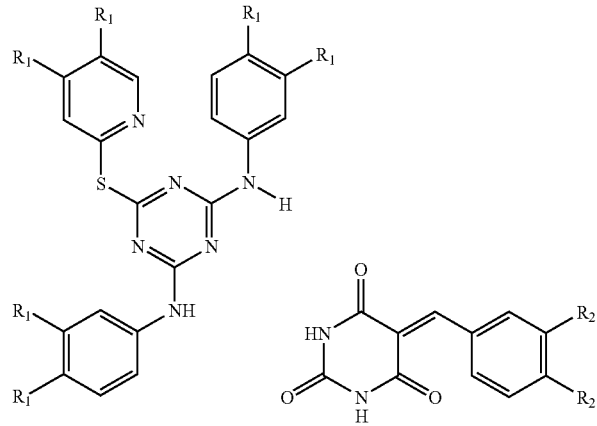
TAM3    BA8
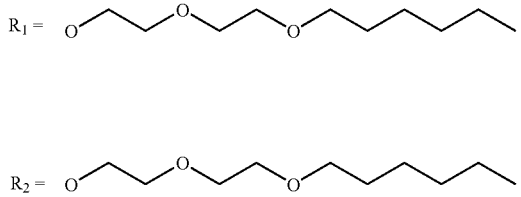
a-71 a-72
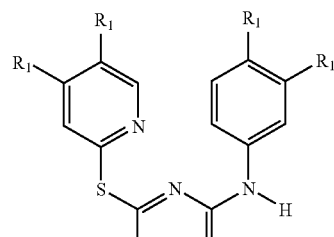
TAM3
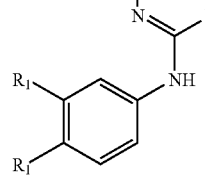
BA9
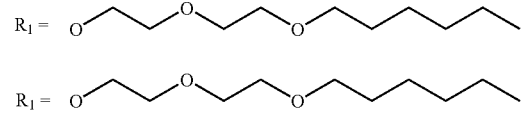
a-73
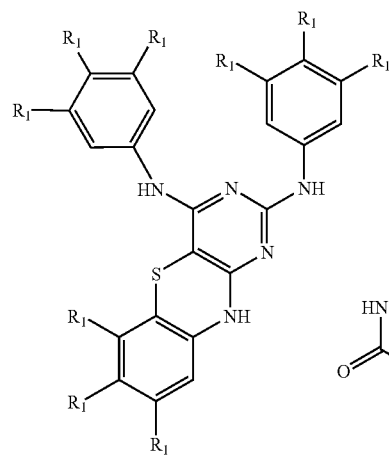
TAM4
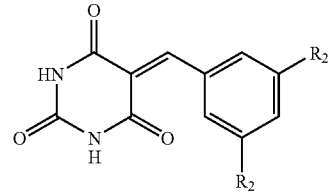
BA4
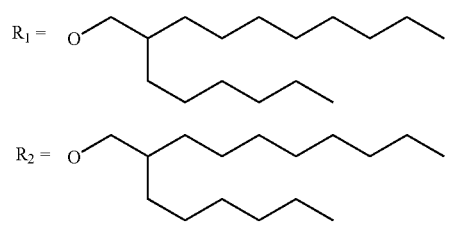
a-74
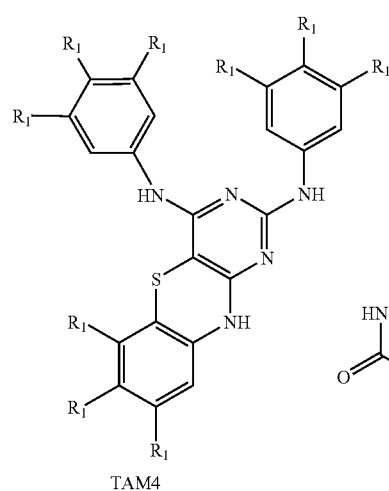
TAM4
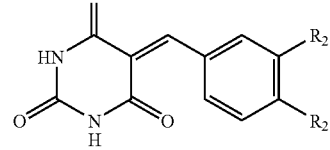
BA5
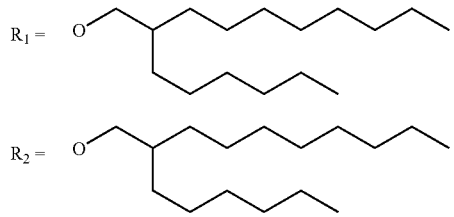

-continued
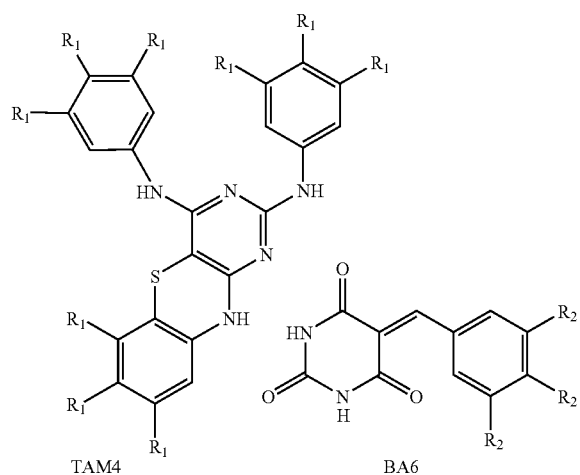
TAM4    BA6
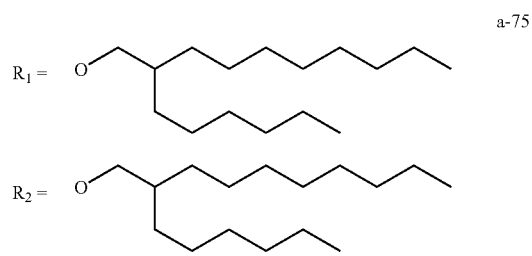
a-75
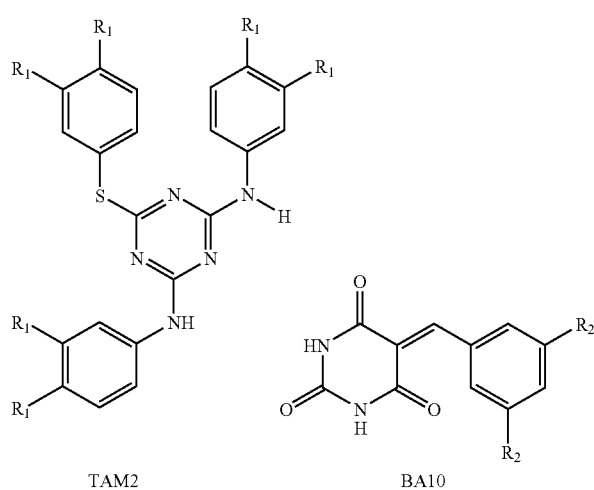
TAM2    BA10
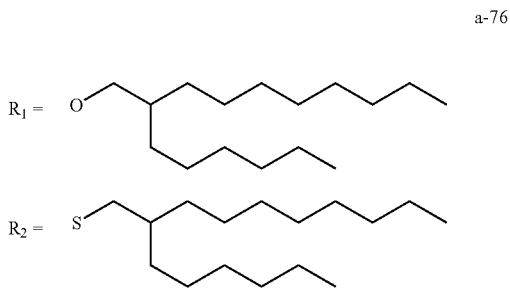
a-76
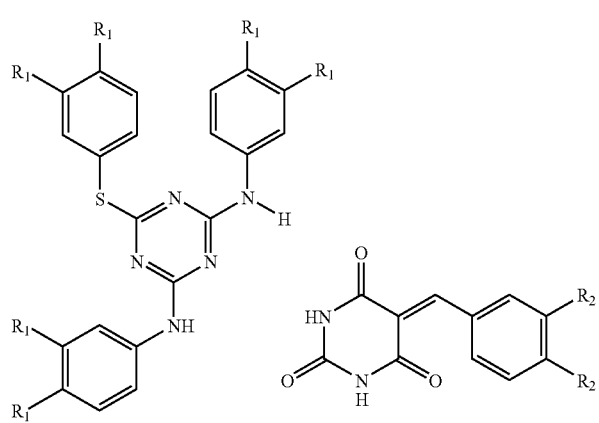
TAM2    BA11
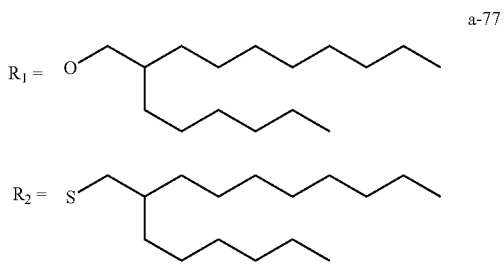
a-77

-continued
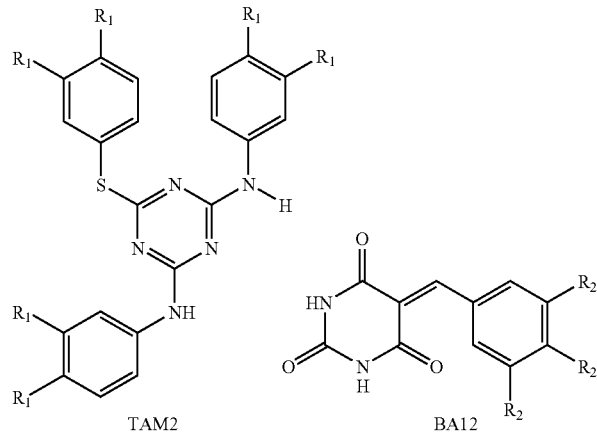
TAM2   BA12
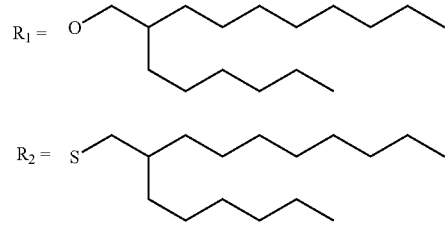
a-78
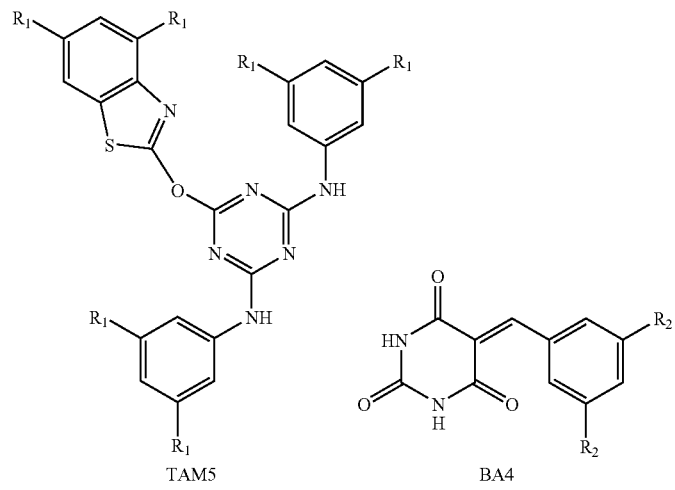
TAM5   BA4
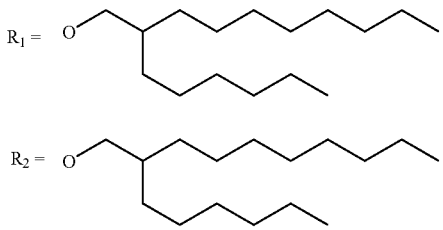
a-79
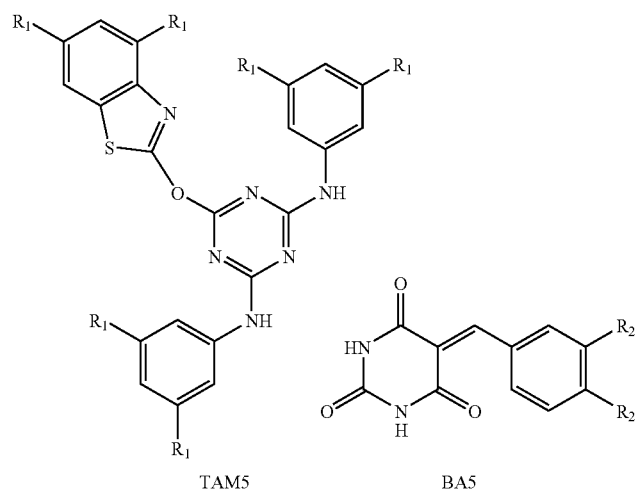
TAM5   BA5
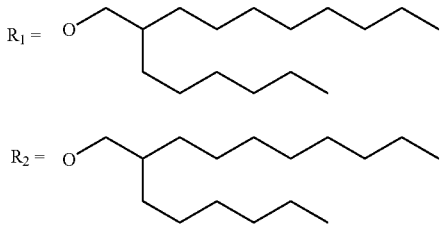
a-80

-continued
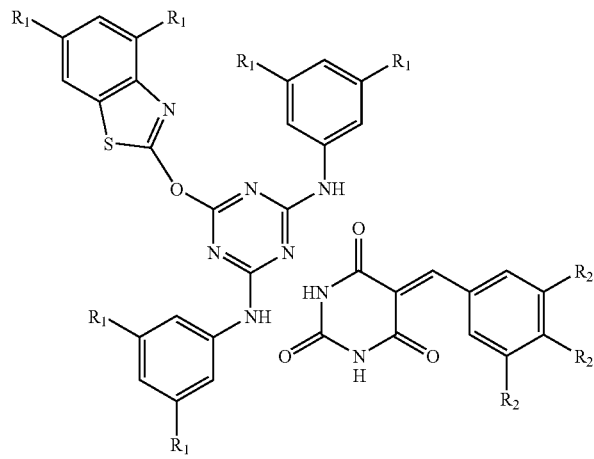
TAM5　　BA6
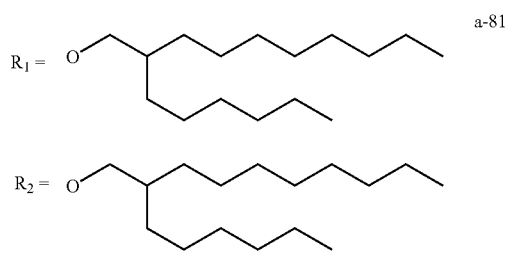
a-81
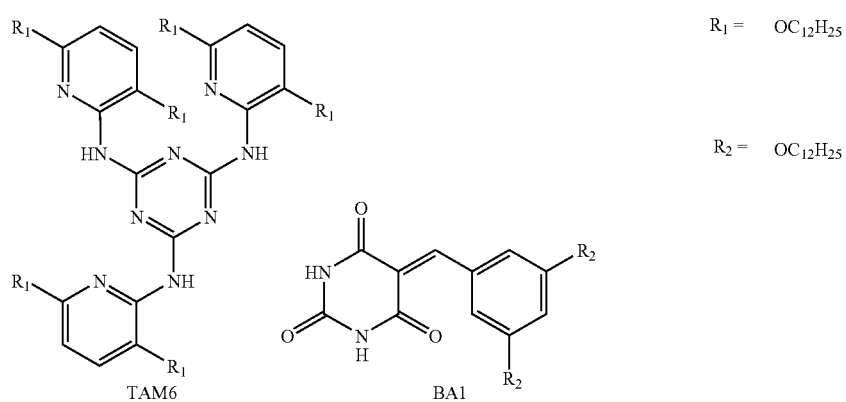
TAM6　　BA1
a-82
$R_1 = OC_{12}H_{25}$
$R_2 = OC_{12}H_{25}$
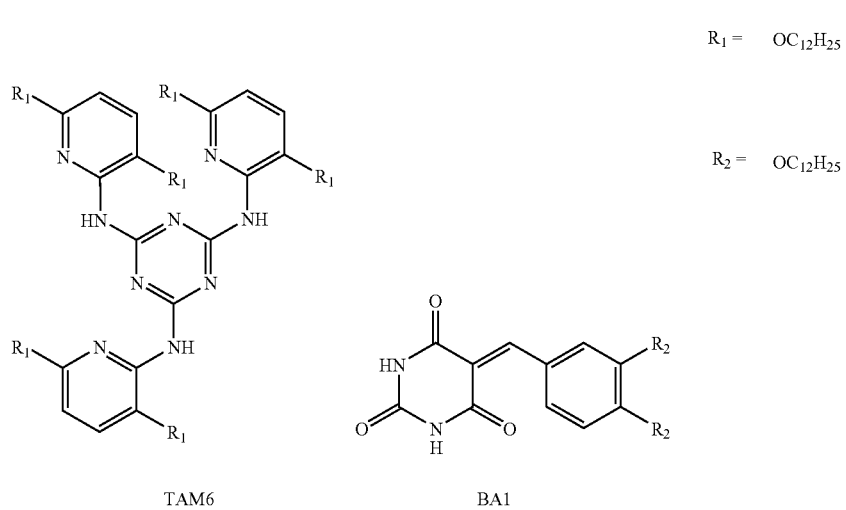
TAM6　　BA1
a-83
$R_1 = OC_{12}H_{25}$
$R_2 = OC_{12}H_{25}$ -continued
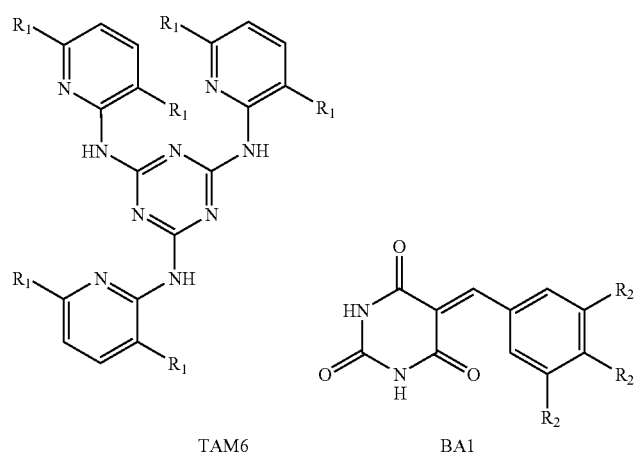
TAM6  BA1
a-84
R₁ = OC₁₂H₂₅
R₂ = OC₁₂H₂₅
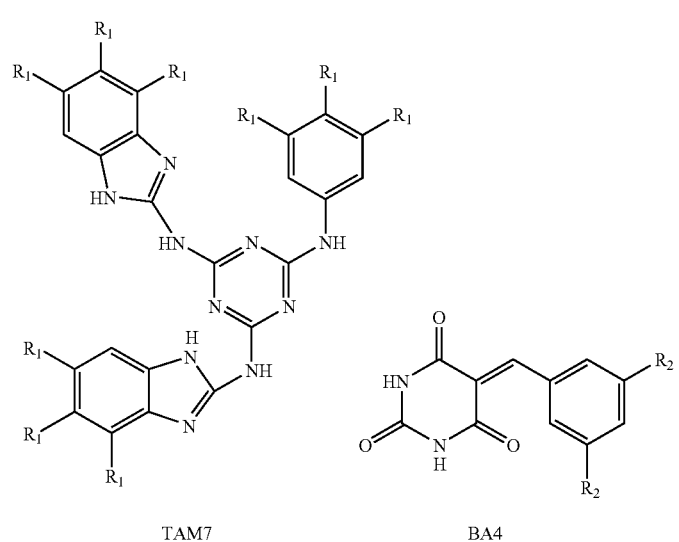
TAM7  BA4
a-85
$R_1 = $ ─O─CH₂─CH(C₆H₁₃)─C₈H₁₇
$R_2 = $ ─O─CH₂─CH(C₆H₁₃)─C₈H₁₇
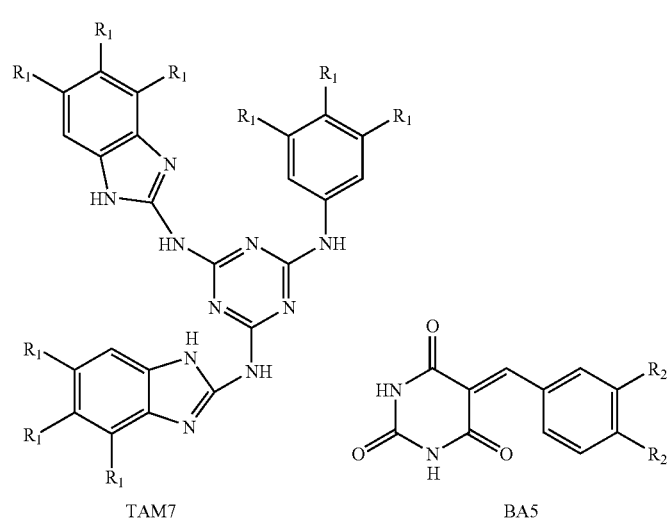
TAM7  BA5
a-86
$R_1 = $ ─O─CH₂─CH(C₆H₁₃)─C₈H₁₇
$R_2 = $ ─O─CH₂─CH(C₆H₁₃)─C₈H₁₇

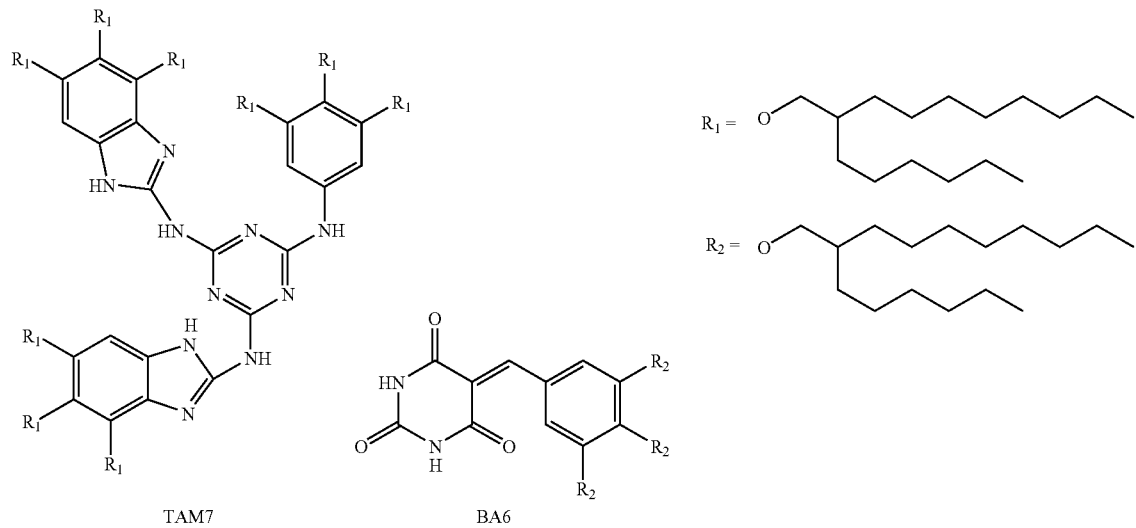
a-87
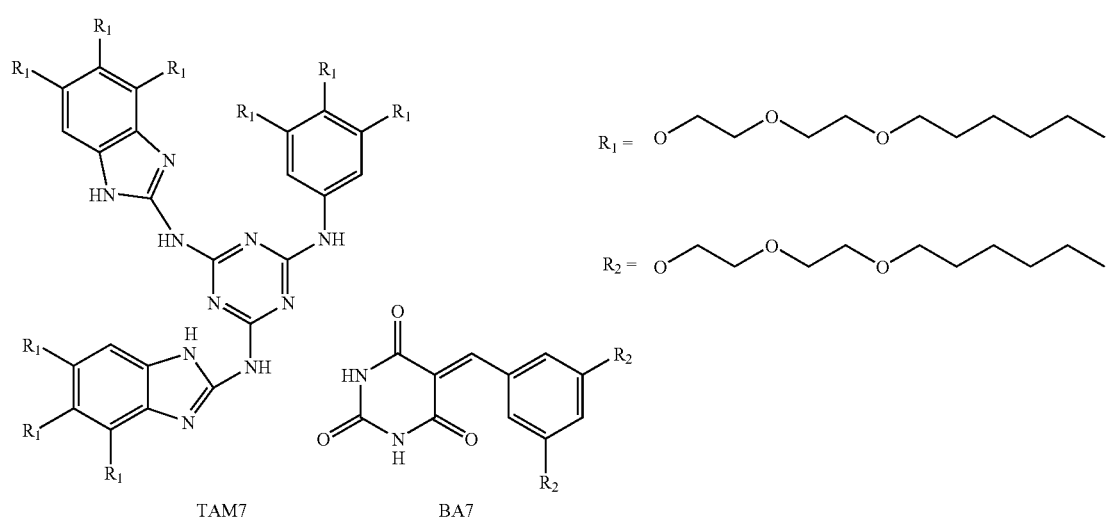
a-88
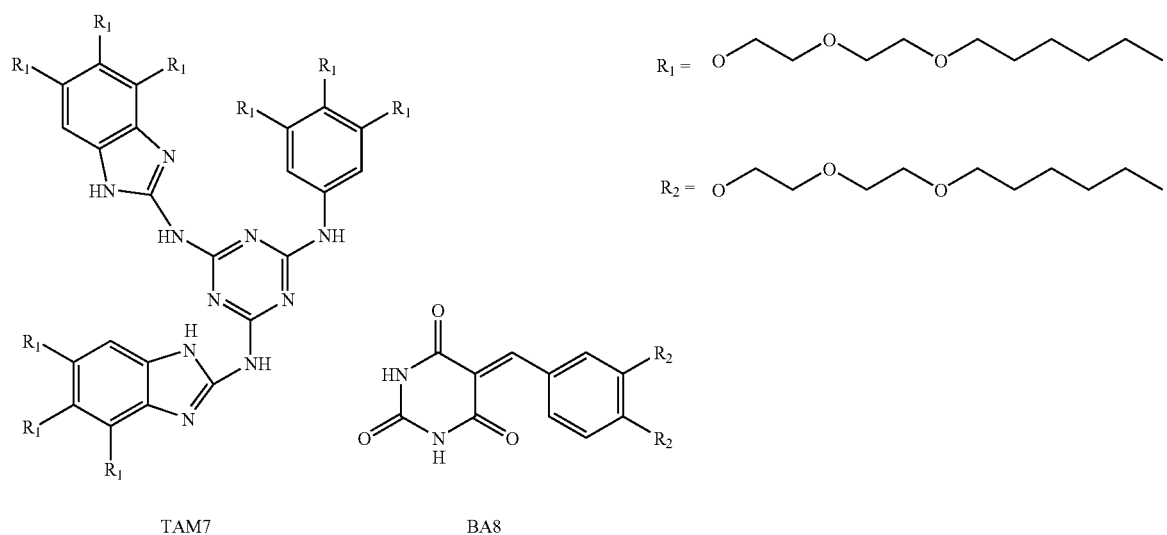
a-89

-continued
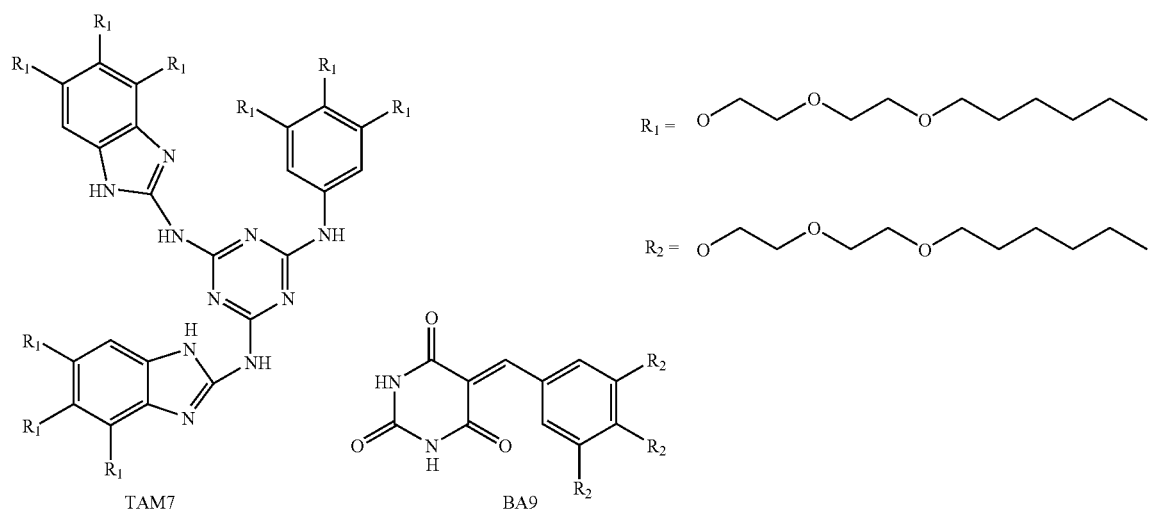
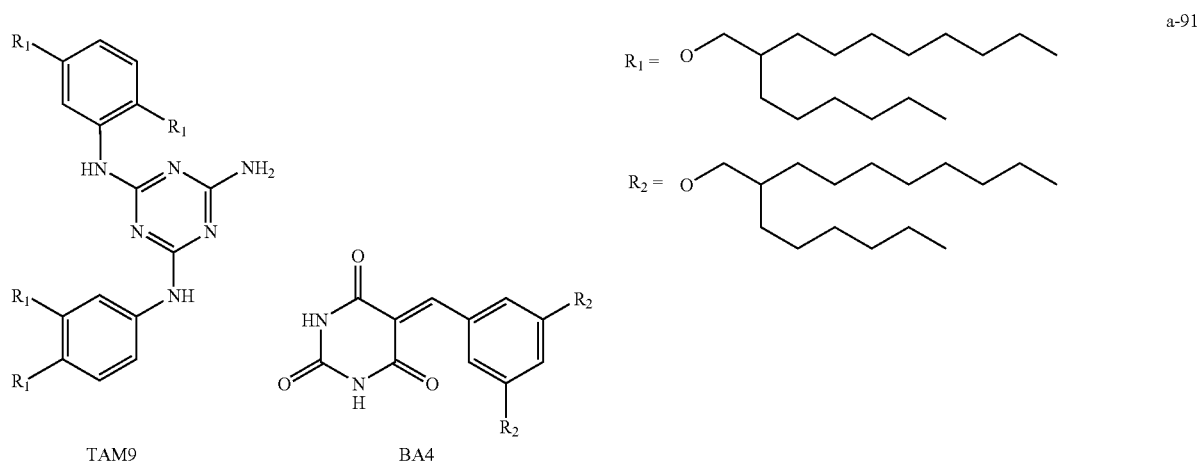
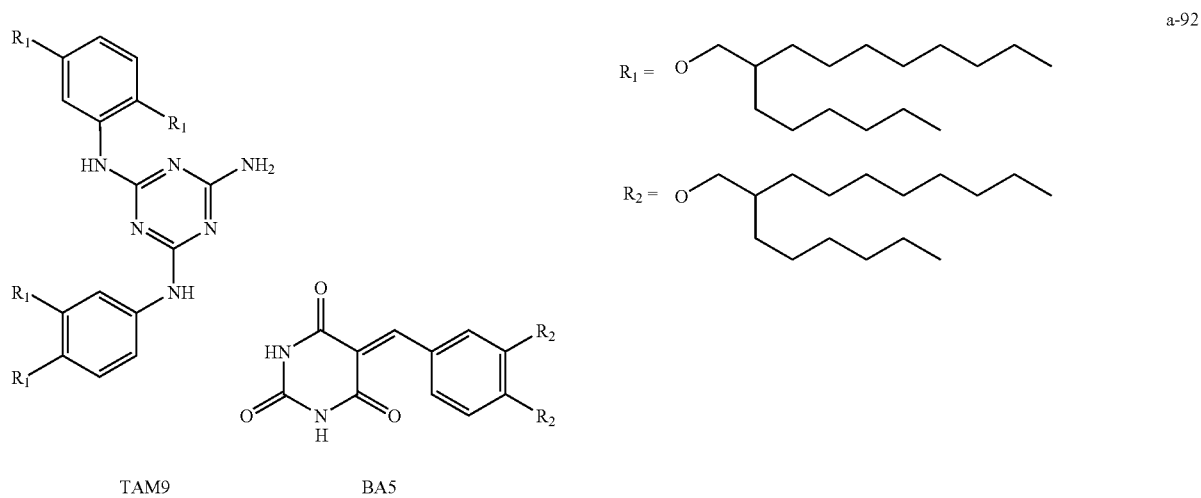

-continued
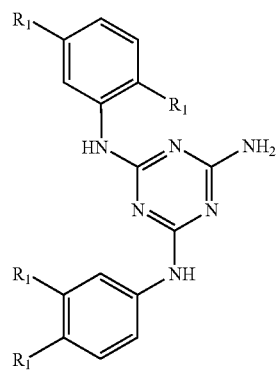
TAM9
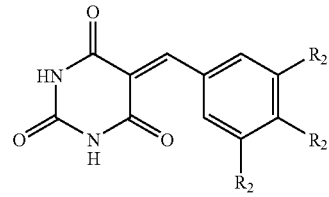
BA6
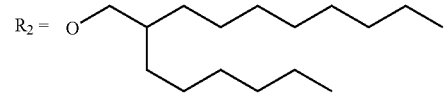
a-93
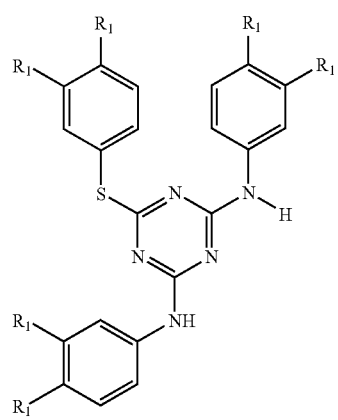
TAM2
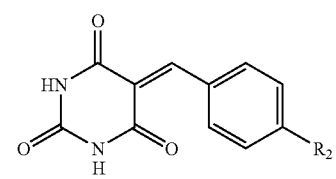
BA13
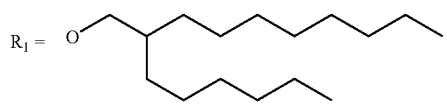
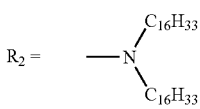
a-94
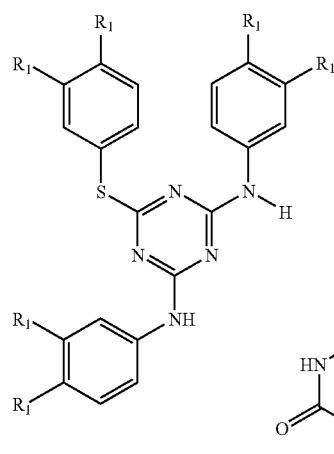
TAM2
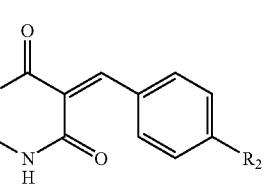
BA14
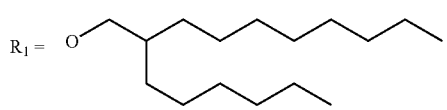
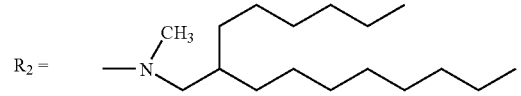
a-95

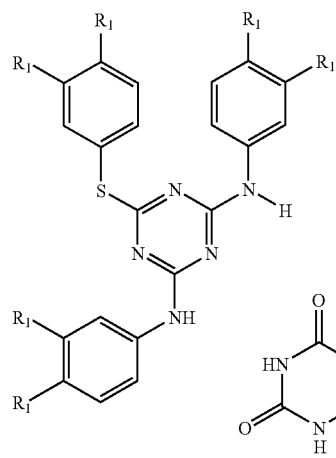# TAM2 BA15
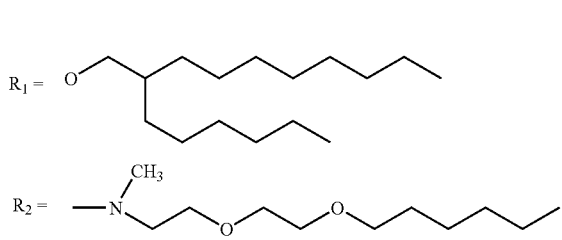
a-96
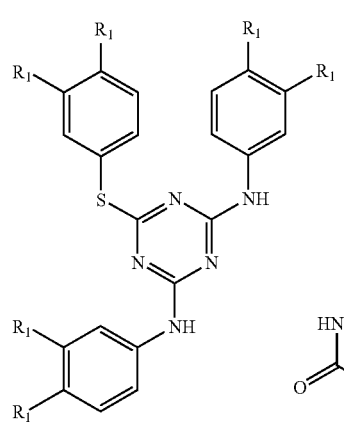# TAM2 BA16
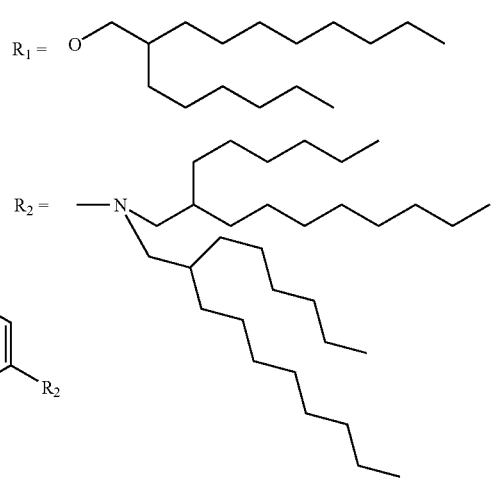
a-97
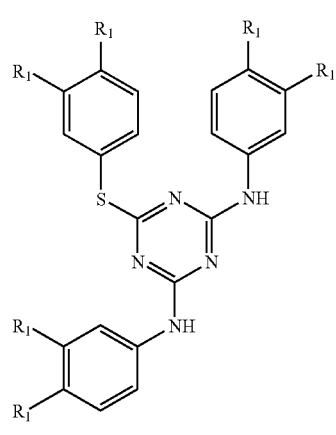# TAM2 BA17
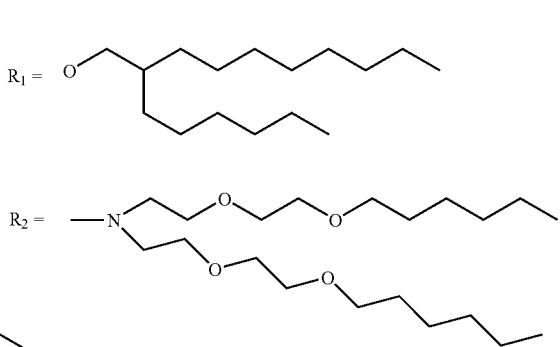
a-98

-continued
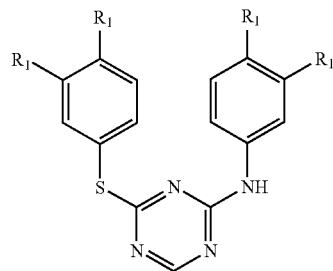
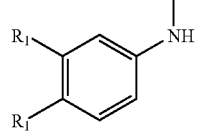
TAM2
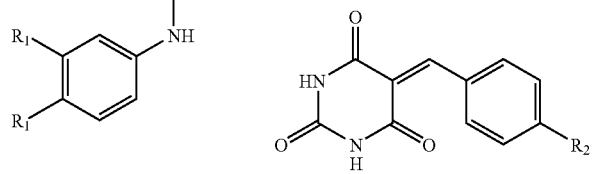
BA18
a-99
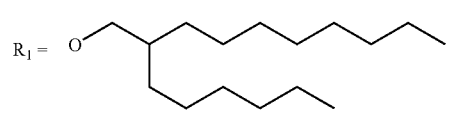
$R_2 =$ SC$_{18}$H$_{37}$
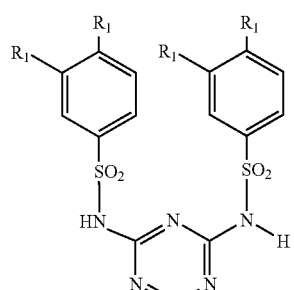
TAM2
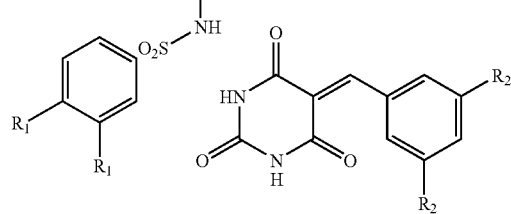
BA19
a-100
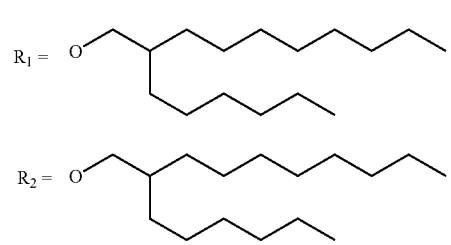
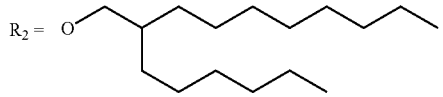
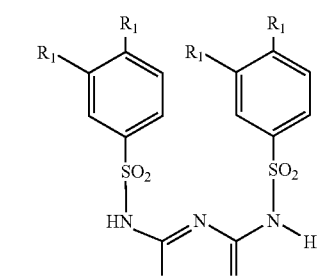
TAM2
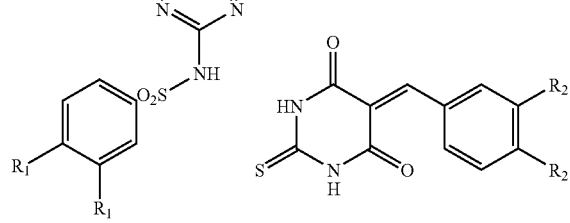
BA20
a-101
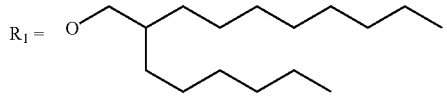

-continued
a-102
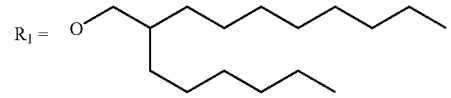
R₁ =
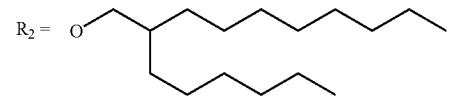
R₂ =
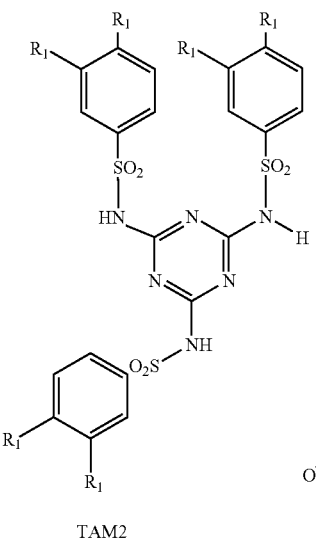
TAM2
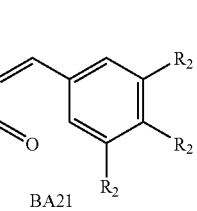
BA21
a-103
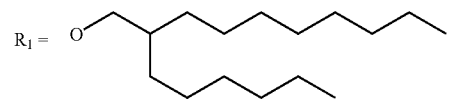
R₁ =
R₂ = —OC₁₂H₂₅
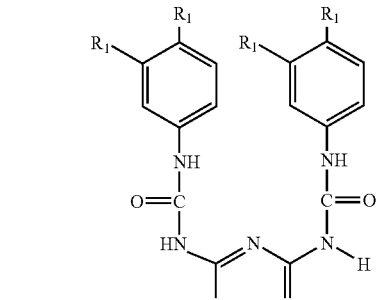 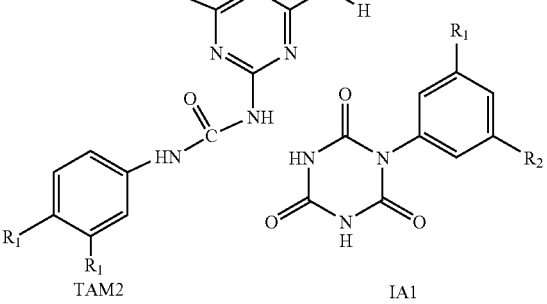
TAM2          IA1
a-104
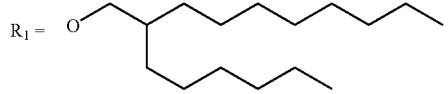
R₁ =
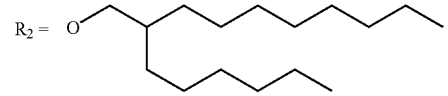
R₂ =
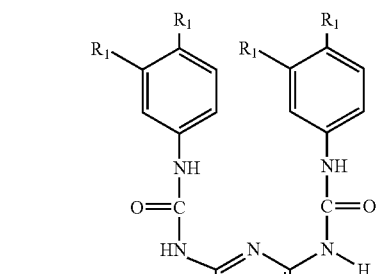 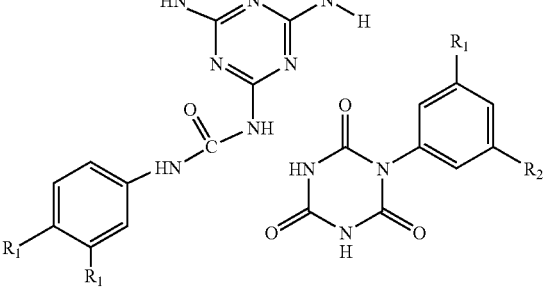
TAM2          IA2

-continued
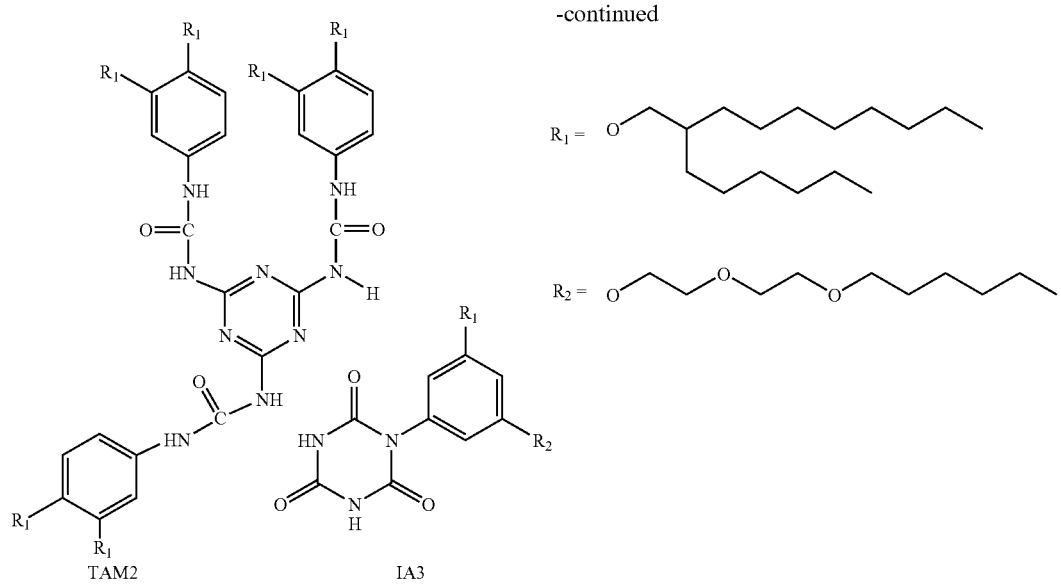
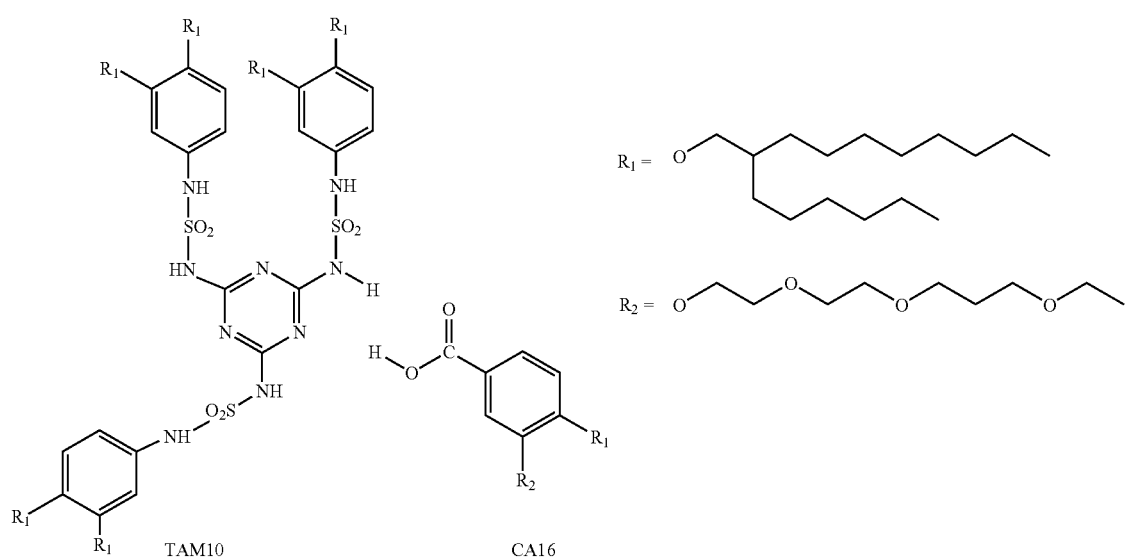
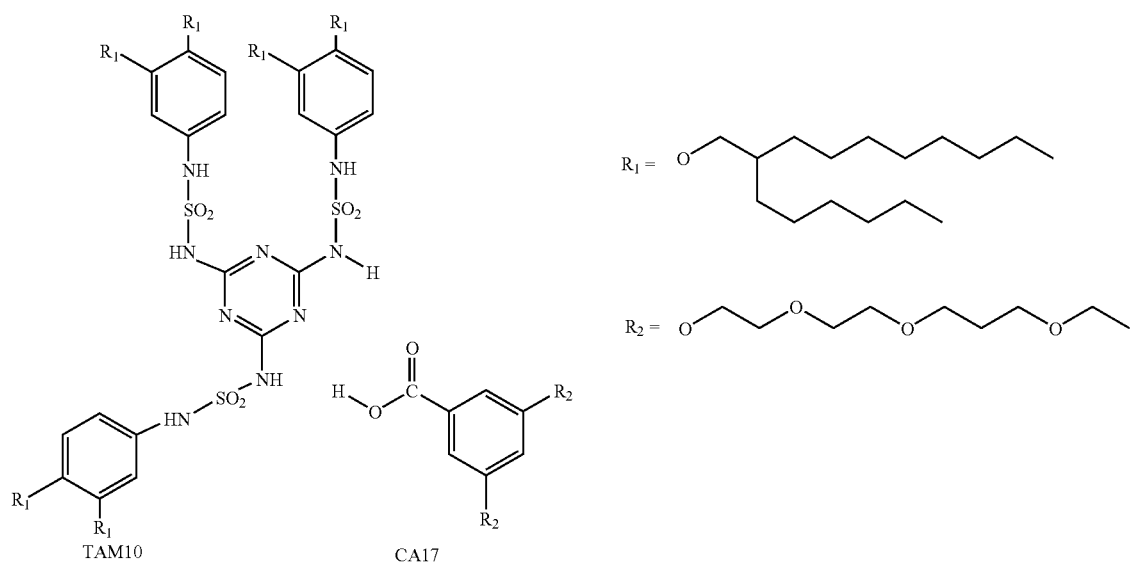

-continued
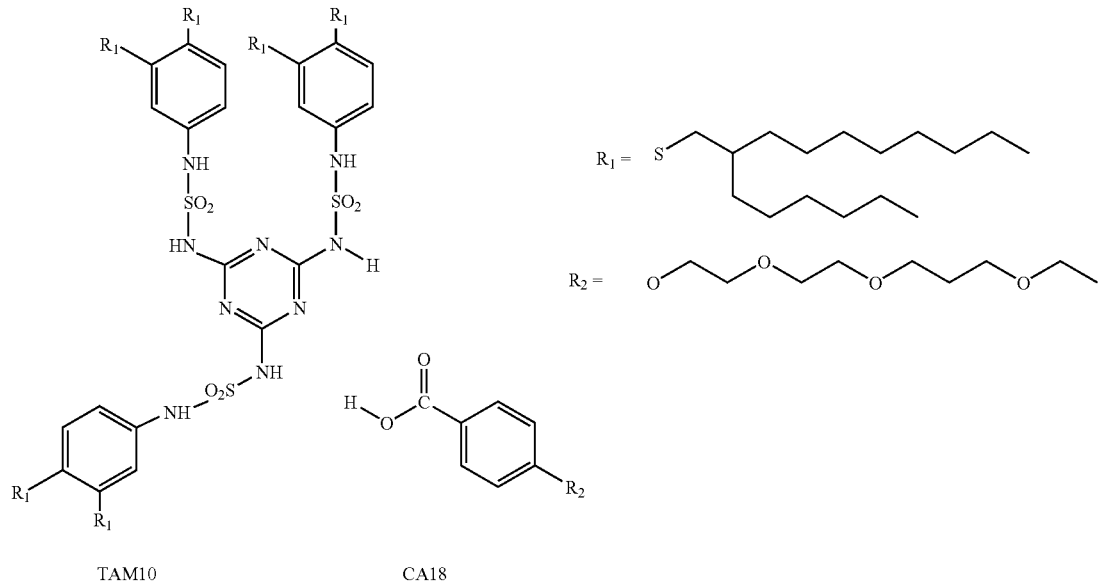
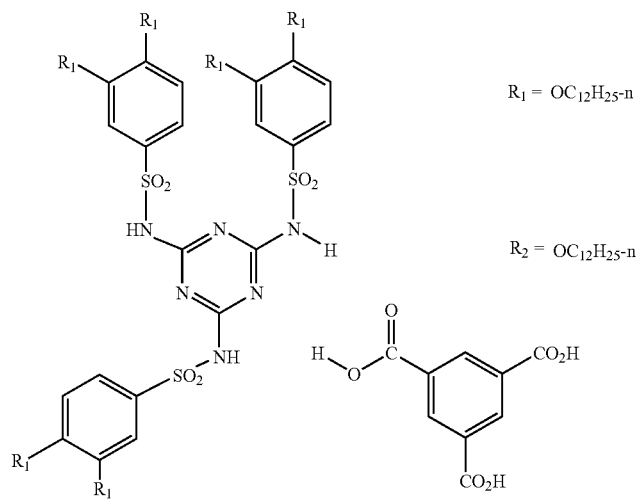
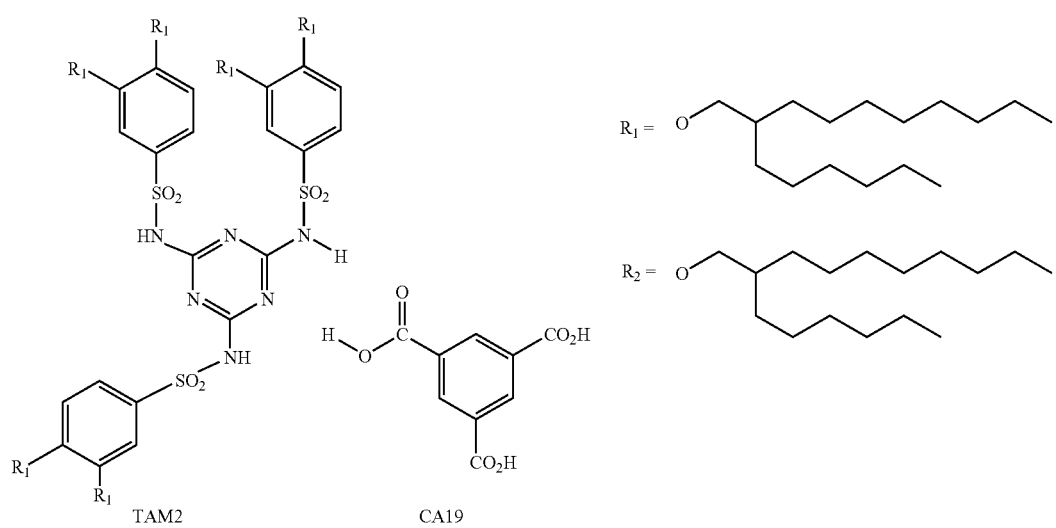

-continued
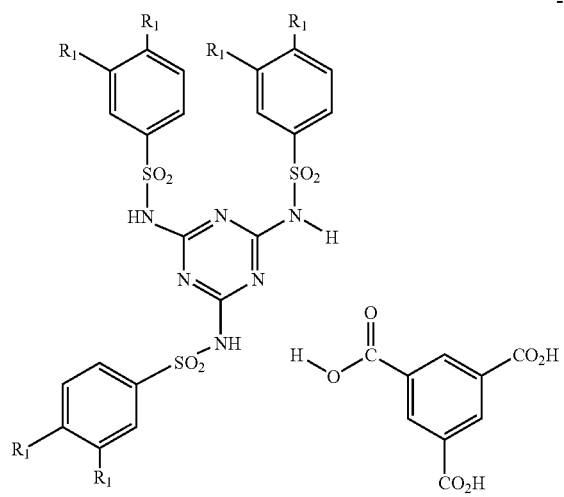
TAM3    CA19
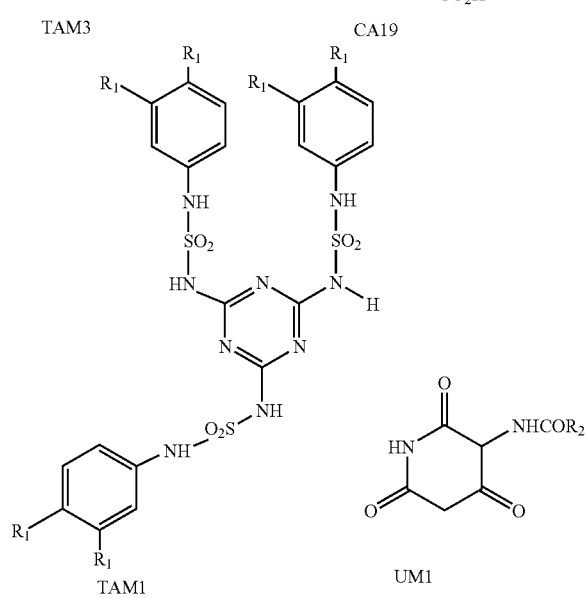
TAM1    UM1
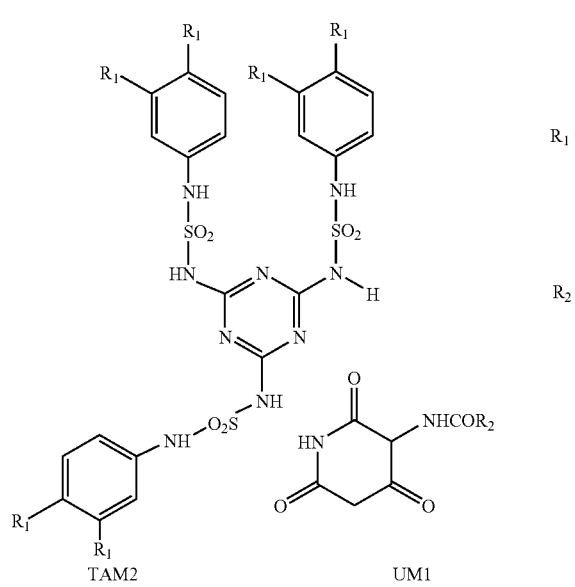
TAM2    UM1
a-111
$R_1 =$ 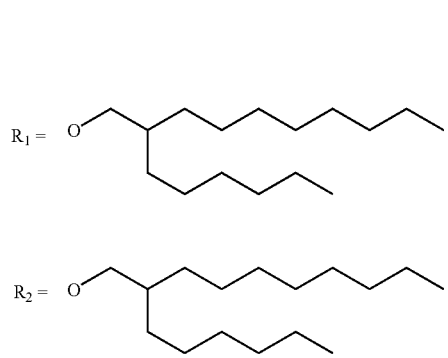
$R_2 =$
a-112
$R_1 = OC_{12}H_{25}\text{-}n$
$R_2 =$
a-113
$R_1 =$
$R_2 =$

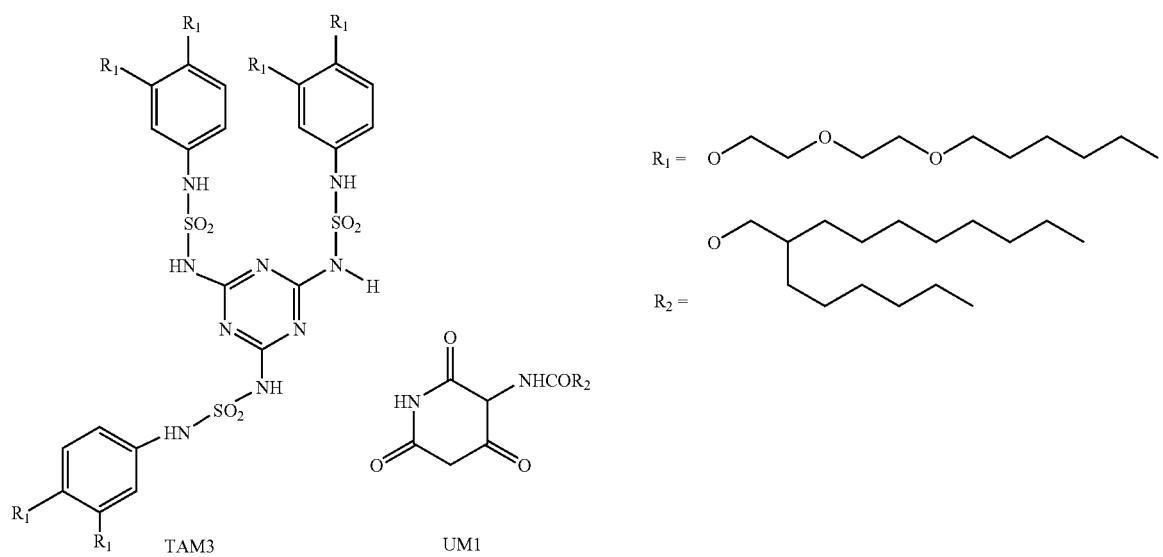
a-114
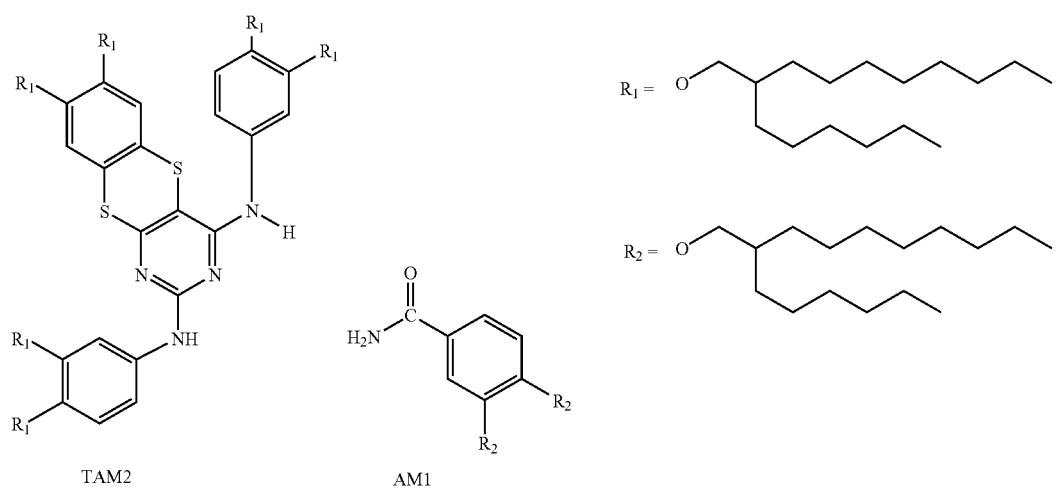
a-115
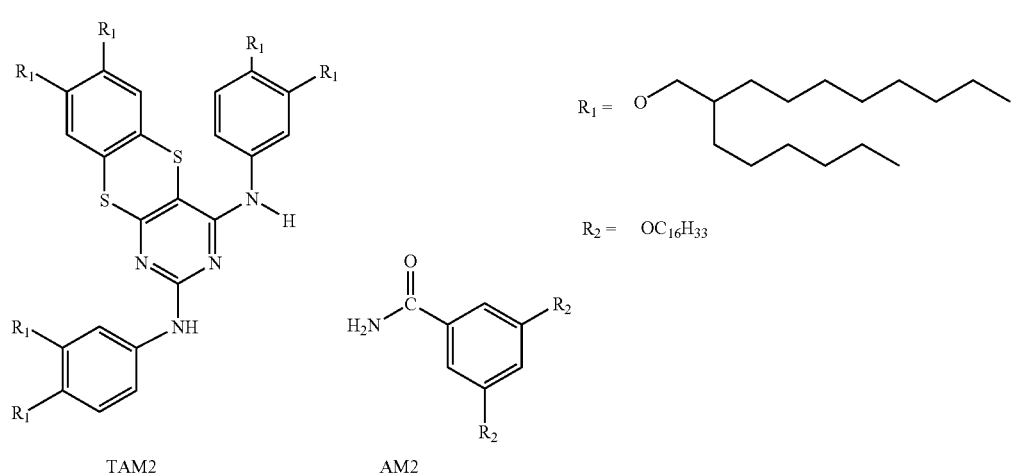
a-116

-continued
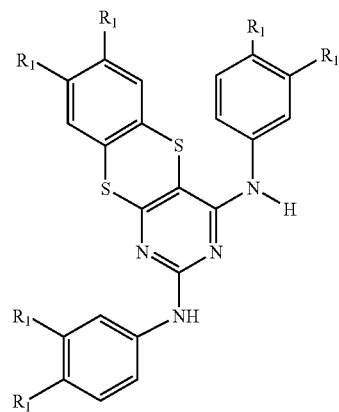
TAM2
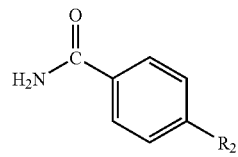
AM3
a-117
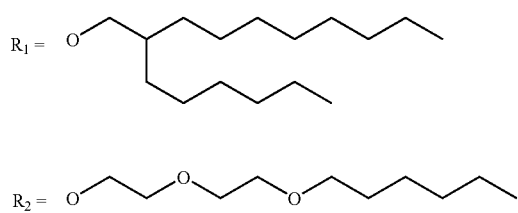
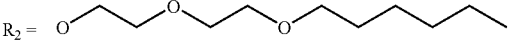
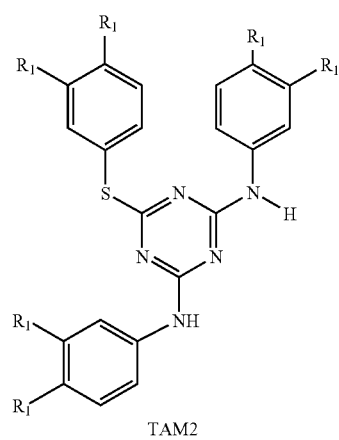
TAM2
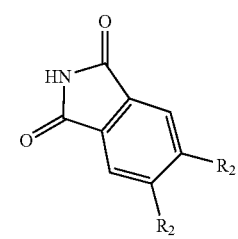
PI1
a-118
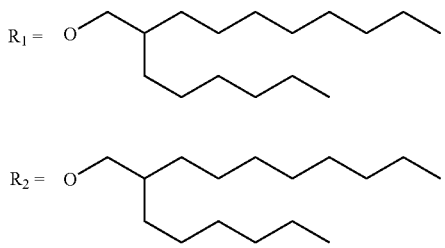
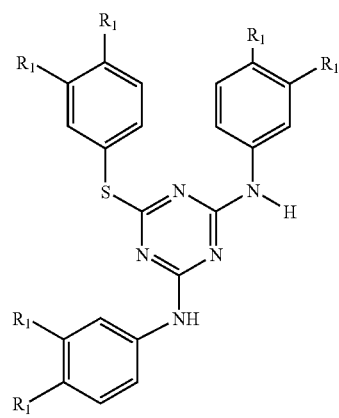
TAM2
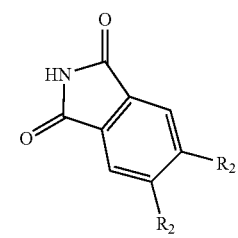
PI2
a-119
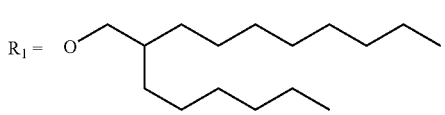
R₂ = OC₁₆H₃₃

-continued
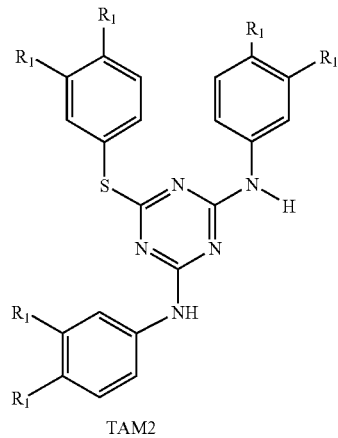
TAM2
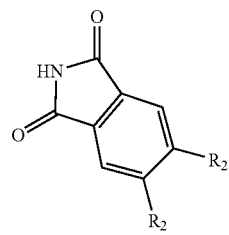
PI3
a-120
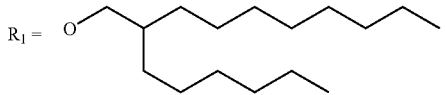
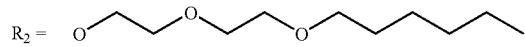
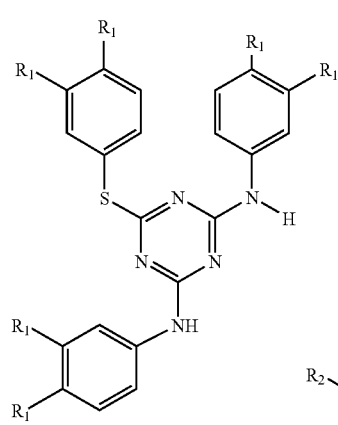
TAM2
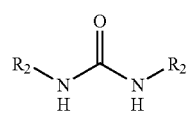
UR1
a-121
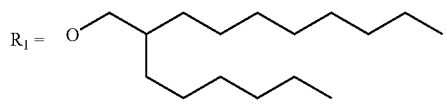
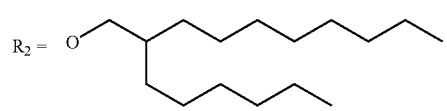
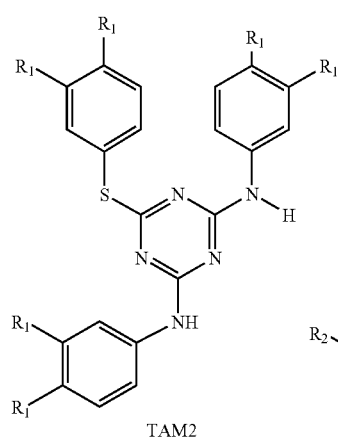
TAM2
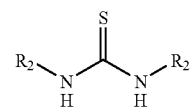
UR2
a-122
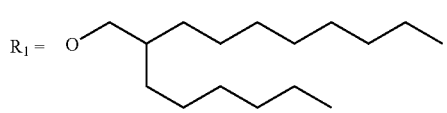

-continued
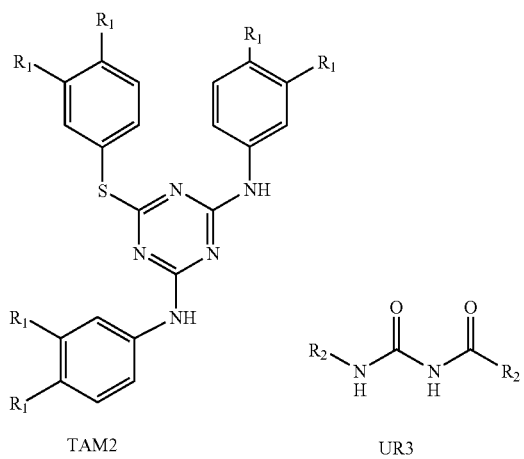
TAM2
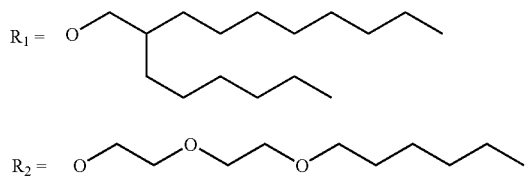
a-123
UR3
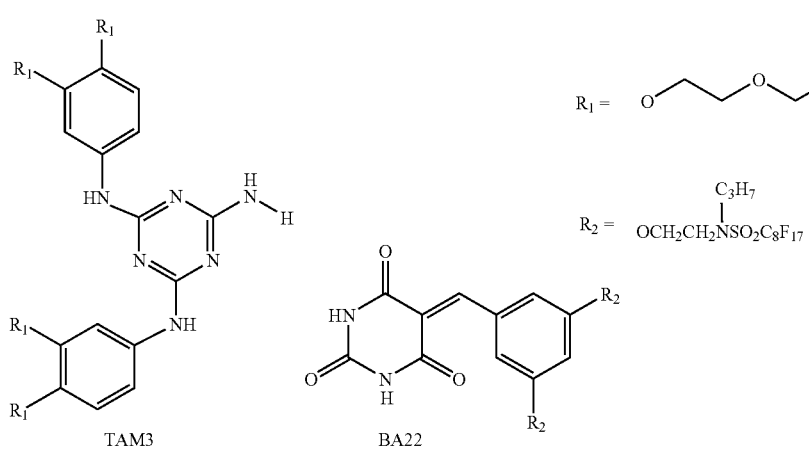
TAM3          BA22
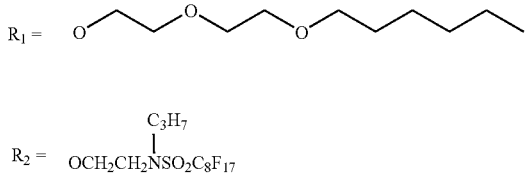
a-124
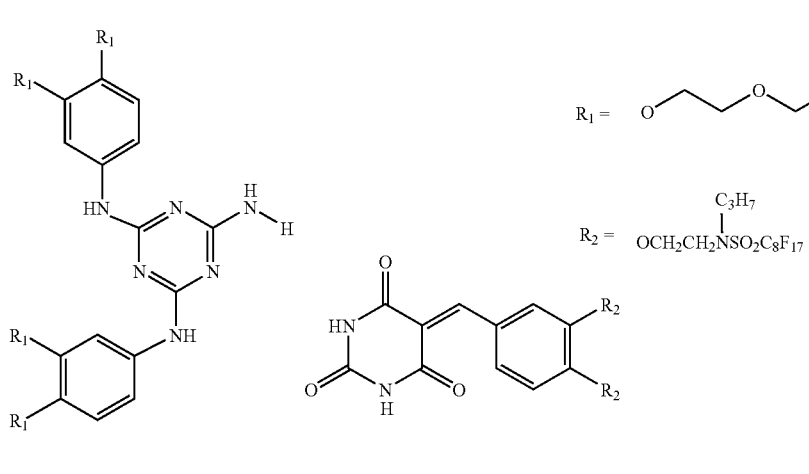
TAM3          BA23
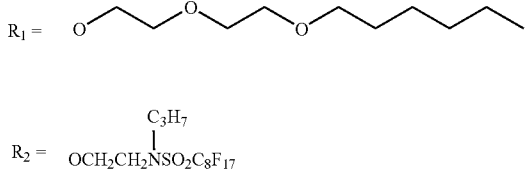
a-125

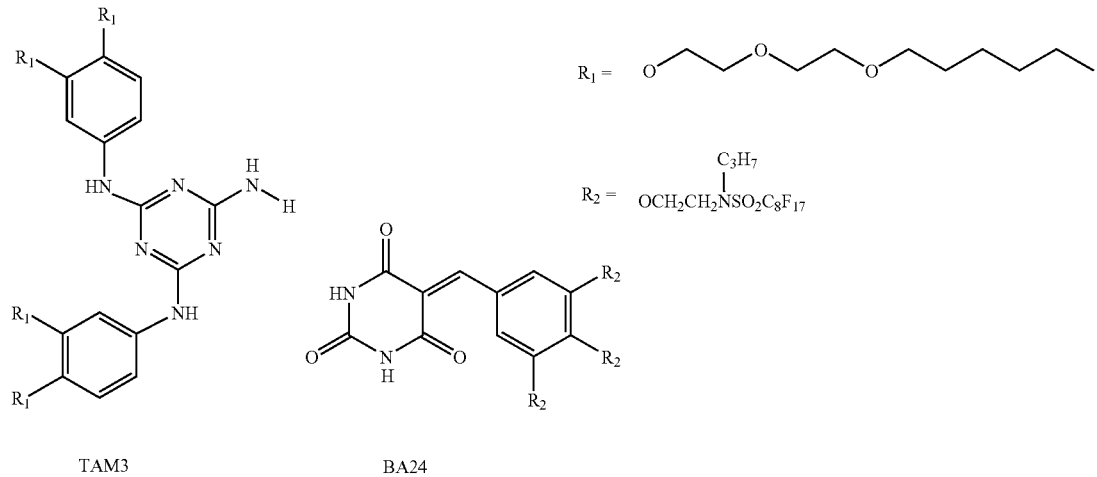
a-126
$R_1 =$ O-CH₂CH₂-O-CH₂CH₂-O-C₆H₁₃ (triethylene glycol hexyl ether chain)
$R_2 =$ OCH₂CH₂N(C₃H₇)SO₂C₈F₁₇
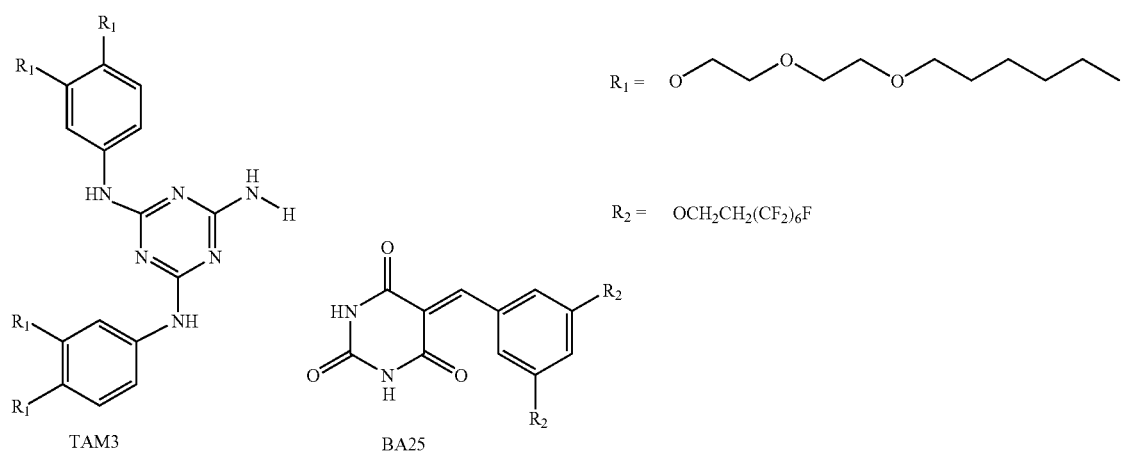
a-127
$R_1 =$ O-CH₂CH₂-O-CH₂CH₂-O-C₆H₁₃
$R_2 =$ OCH₂CH₂(CF₂)₆F
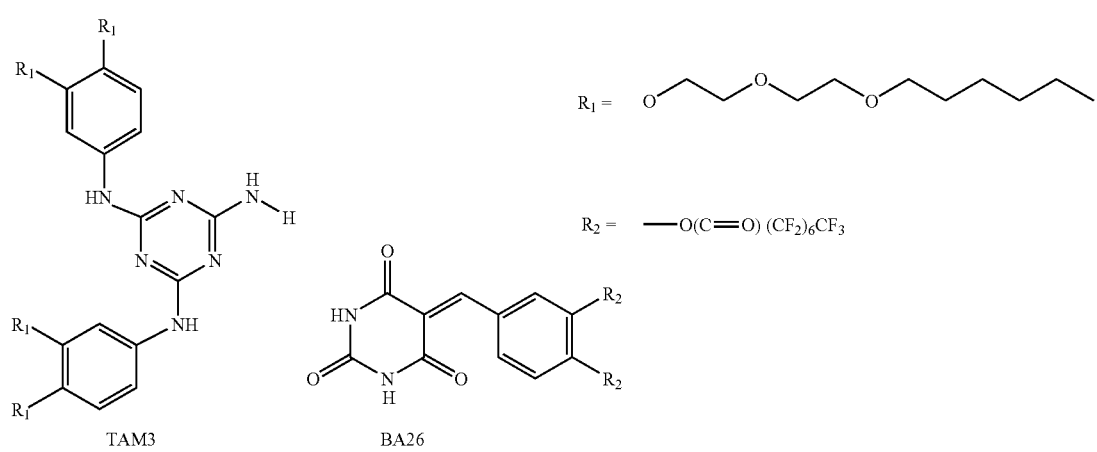
a-128
$R_1 =$ O-CH₂CH₂-O-CH₂CH₂-O-C₆H₁₃
$R_2 =$ —O(C=O)(CF₂)₆CF₃

-continued
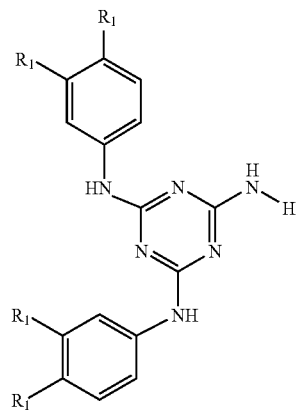 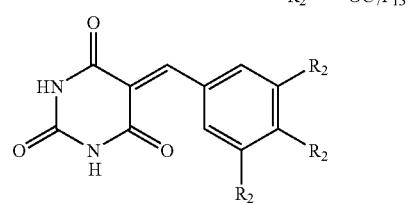
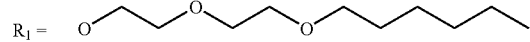
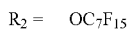
TAM3  BA27
a-129
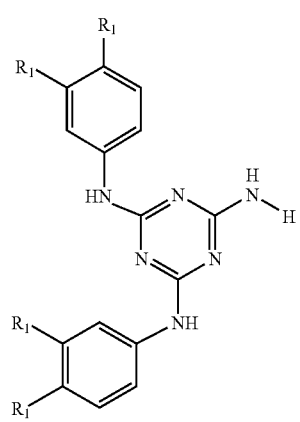 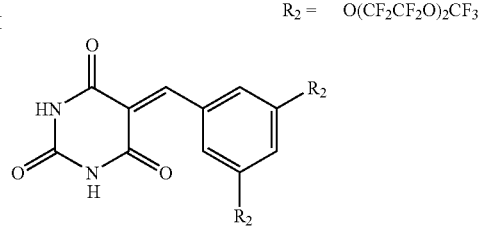
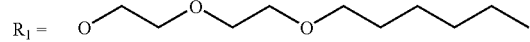
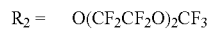
TAM3  BA28
a-130
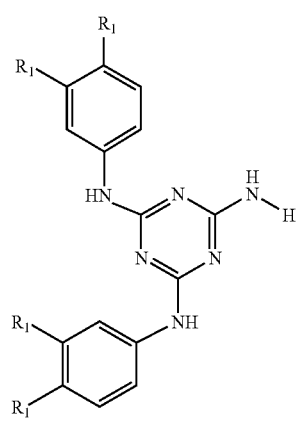 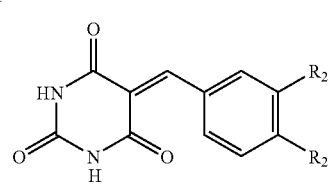
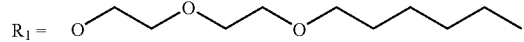
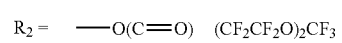
TAM3  BA29
a-131

-continued
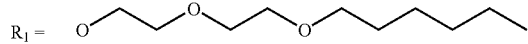
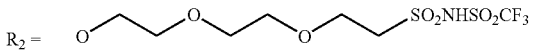
a-132
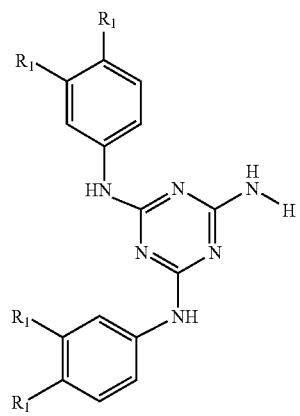
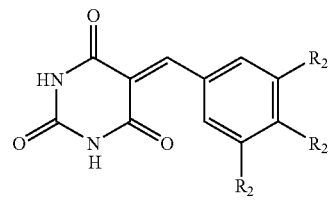
TAM3    BA30
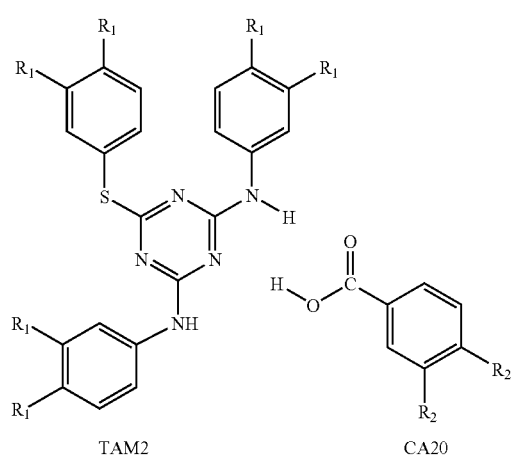
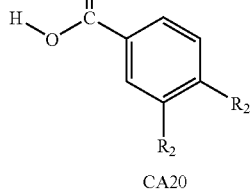
a-133
TAM2    CA20
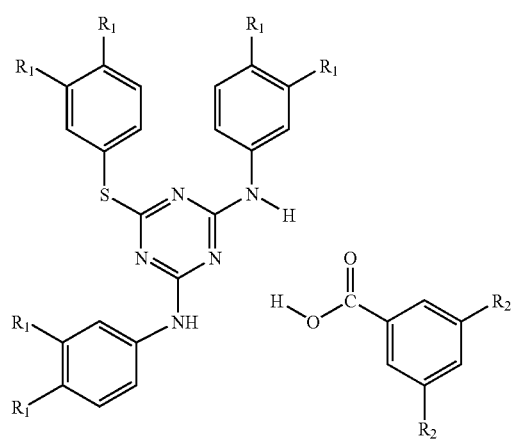
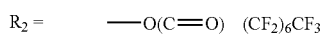
a-134
TAM2    CA21

-continued
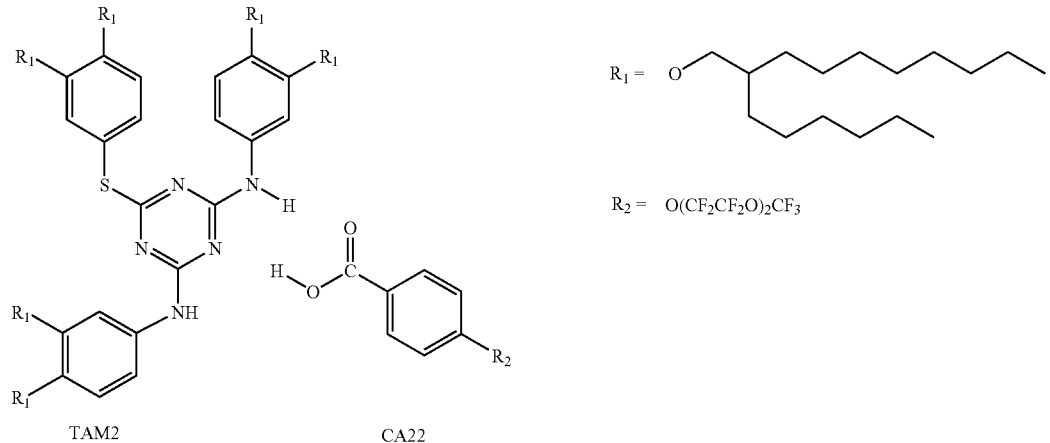
a-135
$R_1 = $ —O—CH$_2$—CH(C$_6$H$_{13}$)—C$_8$H$_{17}$
$R_2 = $ O(CF$_2$CF$_2$O)$_2$CF$_3$
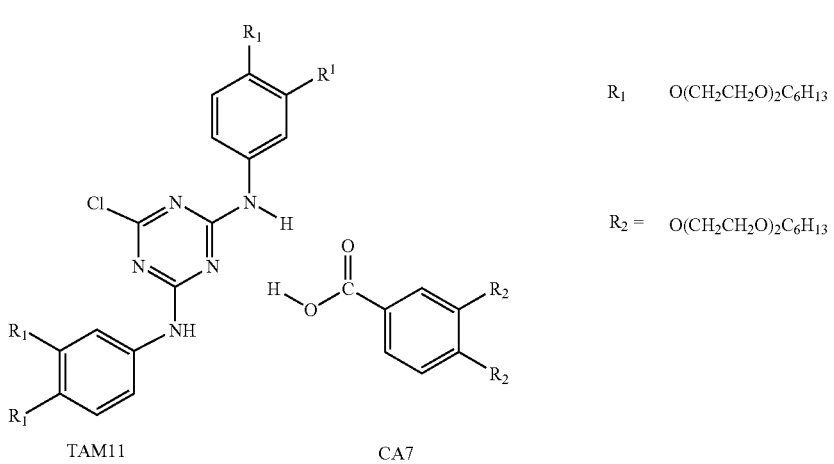
a-139
$R_1$  O(CH$_2$CH$_2$O)$_2$C$_6$H$_{13}$
$R_2 = $  O(CH$_2$CH$_2$O)$_2$C$_6$H$_{13}$
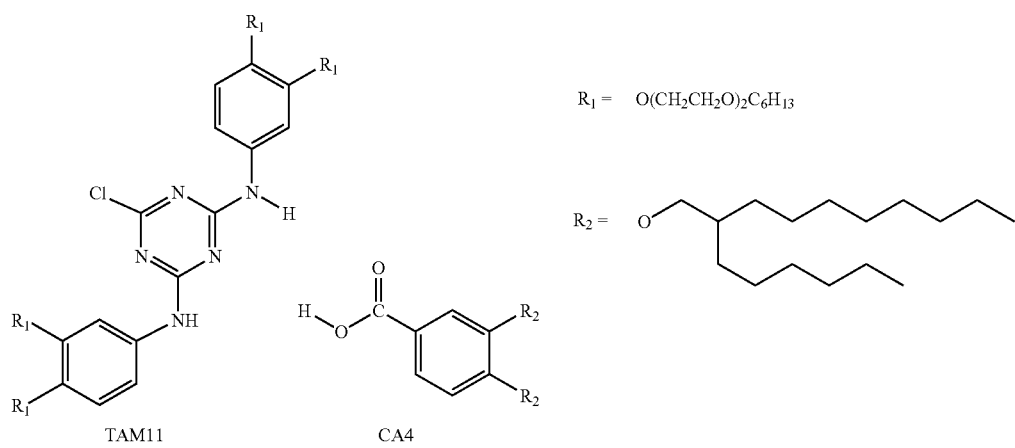
a-140
$R_1 = $ O(CH$_2$CH$_2$O)$_2$C$_6$H$_{13}$
$R_2 = $ —O—CH$_2$—CH(C$_6$H$_{13}$)—C$_8$H$_{17}$ -continued
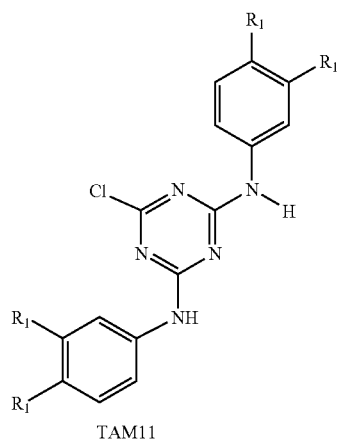 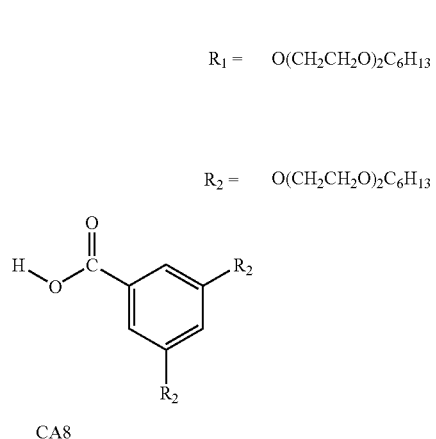
TAM11   CA8
a-141
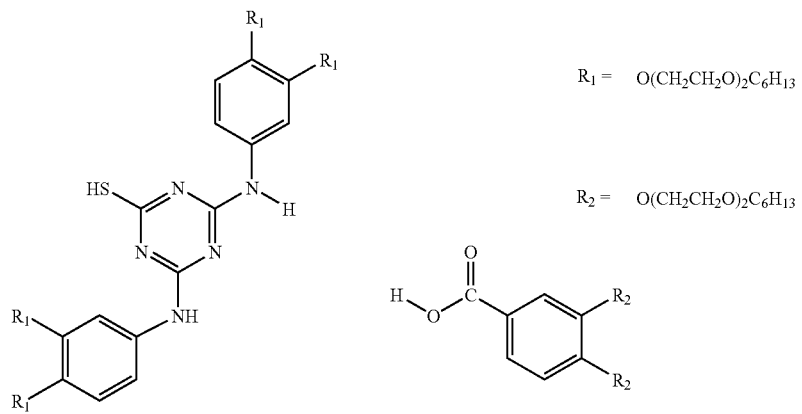
TAM12   CA7
a-142
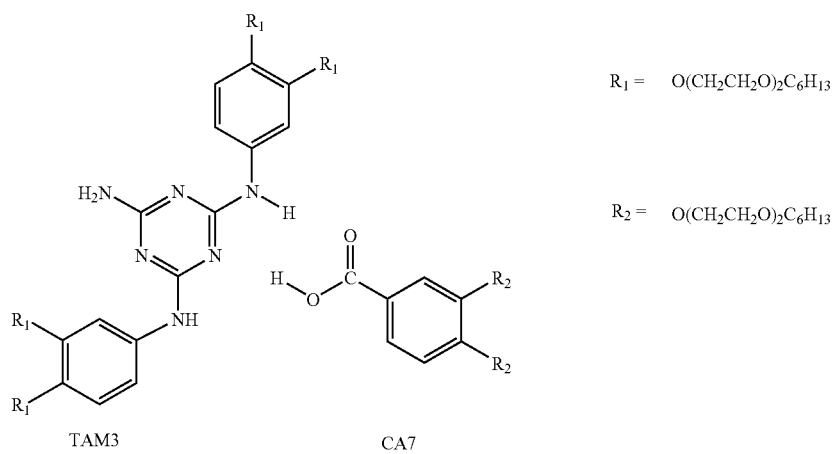
TAM3   CA7
a-143

-continued
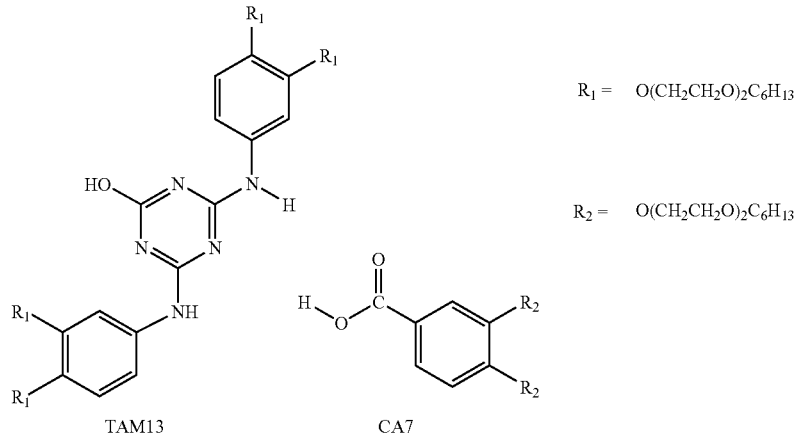
a-144
R₁ = $O(CH_2CH_2O)_2C_6H_{13}$
R₂ = $O(CH_2CH_2O)_2C_6H_{13}$
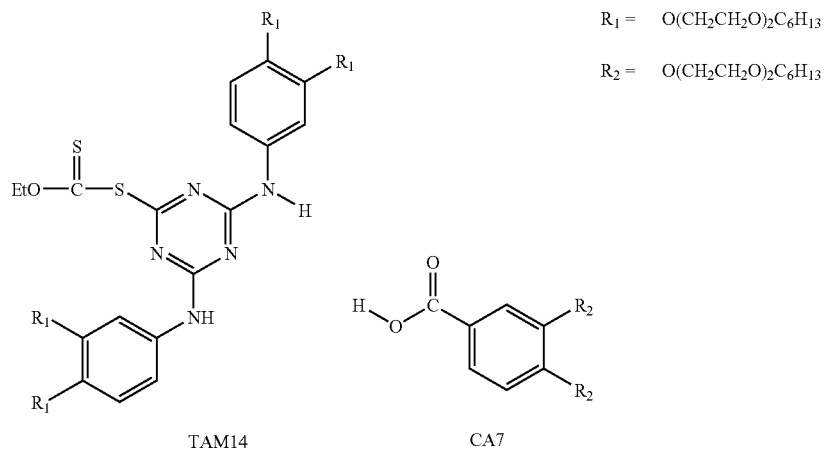
a-145
R₁ = $O(CH_2CH_2O)_2C_6H_{13}$
R₂ = $O(CH_2CH_2O)_2C_6H_{13}$
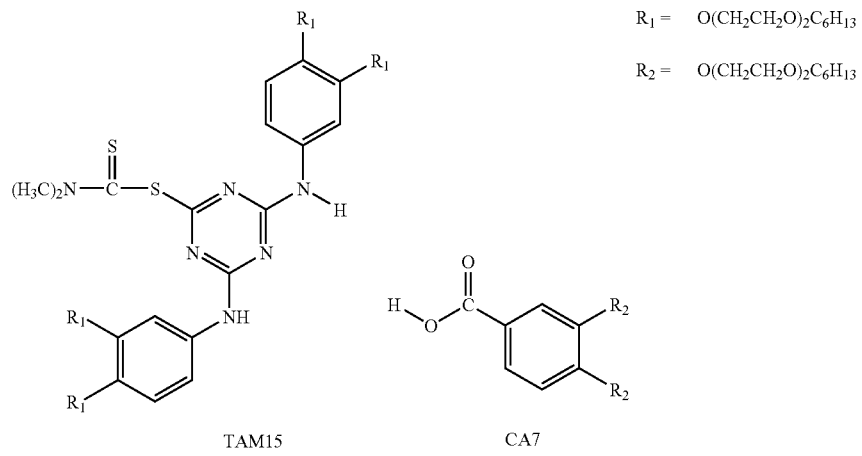
a-146
R₁ = $O(CH_2CH_2O)_2C_6H_{13}$
R₂ = $O(CH_2CH_2O)_2C_6H_{13}$ -continued
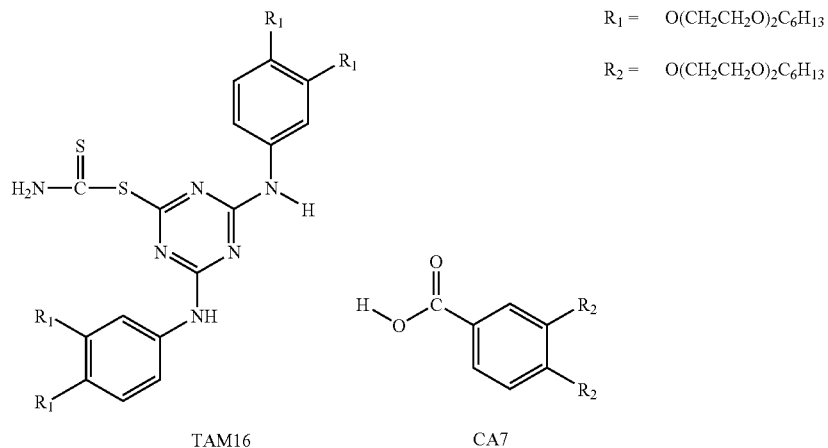
a-147
R₁ = $O(CH_2CH_2O)_2C_6H_{13}$
R₂ = $O(CH_2CH_2O)_2C_6H_{13}$
TAM16    CA7
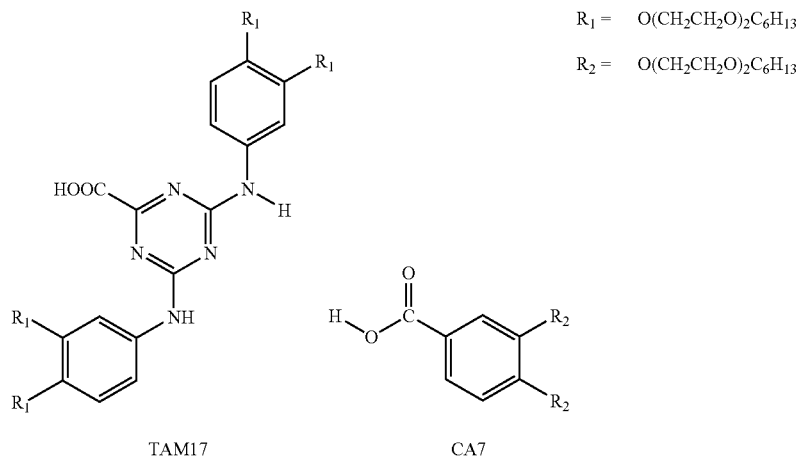
a-148
R₁ = $O(CH_2CH_2O)_2C_6H_{13}$
R₂ = $O(CH_2CH_2O)_2C_6H_{13}$
TAM17    CA7
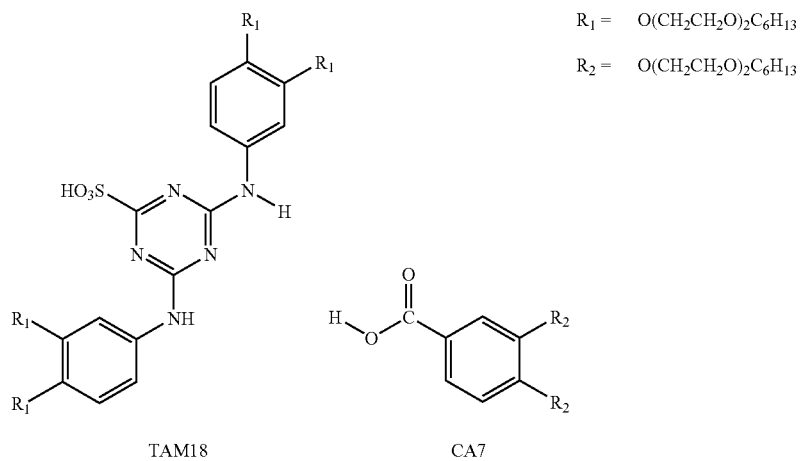
a-149
R₁ = $O(CH_2CH_2O)_2C_6H_{13}$
R₂ = $O(CH_2CH_2O)_2C_6H_{13}$
TAM18    CA7

-continued
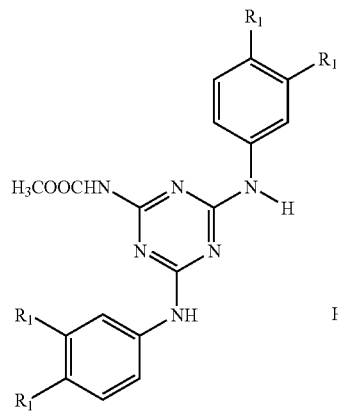
TAM19
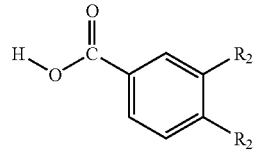
CA7
R₁ = O(CH$_2$CH$_2$O)$_2$C$_6$H$_{13}$
R₂ = O(CH$_2$CH$_2$O)$_2$C$_6$H$_{13}$
a-150
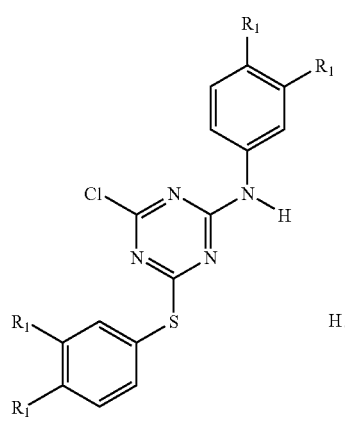
TAM20
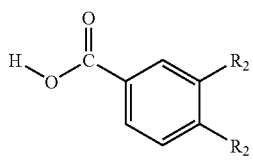
CA7
R₁ = O(CH$_2$CH$_2$O)$_2$C$_6$H$_{13}$
R₂ = O(CH$_2$CH$_2$O)$_2$C$_6$H$_{13}$
a-151
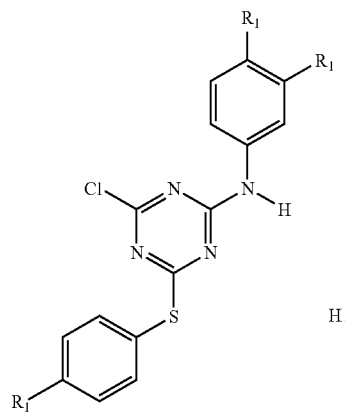
TAM21
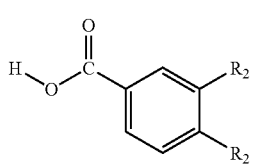
CA7
R₁ = O(CH$_2$CH$_2$O)$_2$C$_6$H$_{13}$
R₂ = O(CH$_2$CH$_2$O)$_2$C$_6$H$_{13}$
a-152

-continued
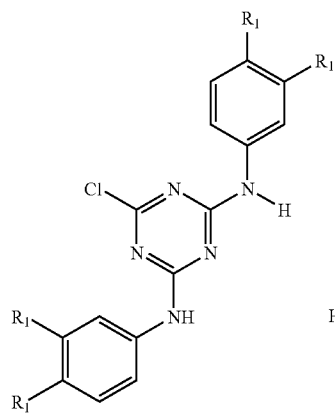
TAM22
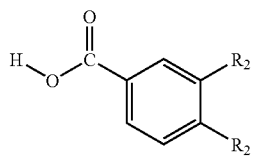
CA7
a-153
R₁ = O—(CH$_2$)$_{10}$CO$_2$(CH$_2$CH$_2$O)$_2$C$_6$H$_{13}$
R$_2$ = O(CH$_2$CH$_2$O)$_2$C$_6$H$_{13}$
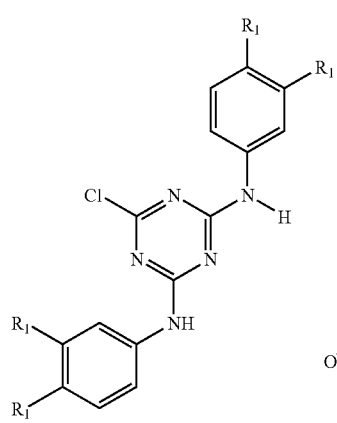
TAM11
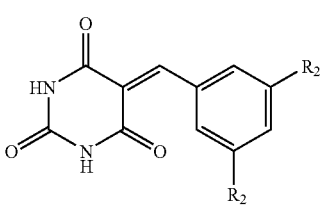
BA7
a-154
R$_1$ = O(CH$_2$CH$_2$O)$_2$C$_6$H$_{13}$
R$_2$ = O(CH$_2$CH$_2$O)$_2$C$_6$H$_{13}$
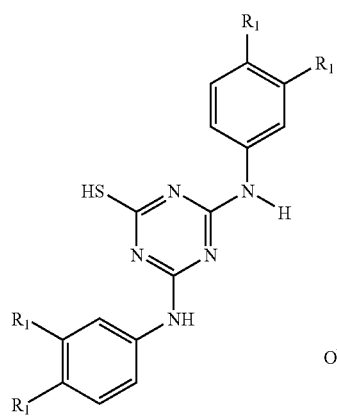
TAM12
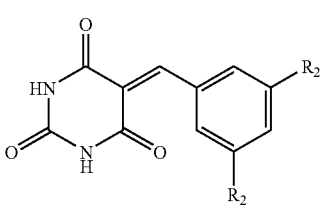
BA4
a-155
R$_1$ = O(CH$_2$CH$_2$O)$_2$C$_6$H$_{13}$
R$_2$ = 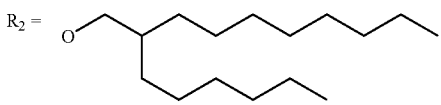

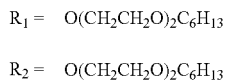

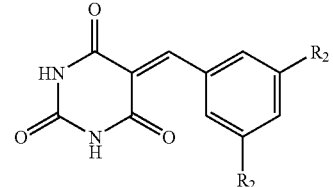

a-156

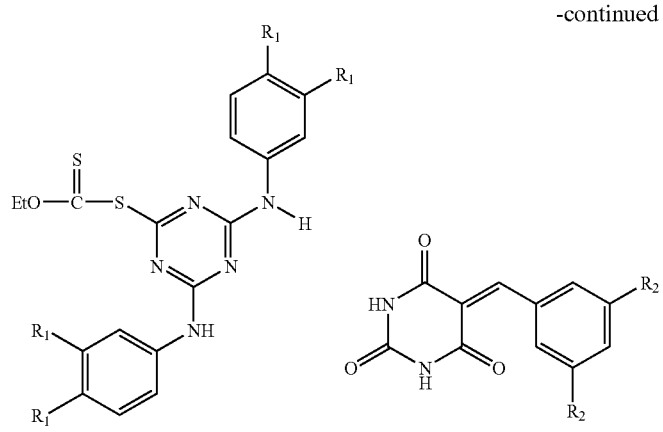

TAM14  BA7

The compound represented by the formula (I) and the other compound capable of forming a complex compound therewith can be synthesized by properly combining known methods for manufacturing.

The molecular complex compound preferably has an apparent viscosity of 1000 mpa·s or less at 40° C. and 20 mpa·s or more at 120° C. respectively, more preferably 1000 to 50 mPa·s at 40° C. and to 25 mPa·s or more at 120° C. respectively, especially preferably 800 to 1000 mPa·s at 40° C. and 25 mPa·s or more at 120° C. respectively.

The molecular complex compound used for the lubricant composition of the present invention can independently be used as a lubricant, and also used in a mixed form with a lubricant base oil as a lubricant aids, extreme pressure agents, friction coefficient modifiers and anti-wear additives.

The lubricant base oil is not specifically be limited, and any of those generally used as a lubricant base oil will be available, which is exemplified by mineral oil, synthetic oil and any mixed oils thereof. Possible examples of such lubricant base oil include solvent-refined raffinate obtained by extracting a source oil, which is derived from a paraffin-base, intermediate-base or naphthene-base crude oil by distillation under atmospheric or reduced pressure, using an aromatic solvent such as phenol, furfural or N-methylpyrrolidone; hydrogenated oil obtained by treating the source oil with hydrogen under hydrogenation conditions in the presence of hydrogenation catalyst such as cobalt or molybdenum immobilized on silica-alumina support; isomerized oil obtained by treating the source oil with hydrogen under severe decomposition reaction conditions in the presence of hydrogenation decomposition catalyst; and fraction of lubricating oil obtained by a combined process of solvent refining and hydrogenation of the source oil, or by a combined process of hydrogenation and isomerization or the like. In particular, those obtained by a combined process of hydrogenation and isomerization or the like, having high viscosity index, are preferable. Any of such manufacturing methods can arbitrarily be added with the individual processes for dewaxing, hydrogenation finishing and clay treatment. The mineral oil can also be classified into soft neutral oil, medium neutral oil, heavy neutral oil and bright stock, which can properly be mixed depending on target performances.

The synthetic oil can be exemplified by poly(a-olefin), a-olefin oligomer, polybutene, alkylbenzene, polyol ester, dibasic acid ester, polyoxyalkylene glycol, polyoxyalkylene glycol ether and silicone oil. These mineral oils and synthetic oils may be used independently or in any combinations of two or more thereof. It is also allowable to use mineral oil and synthetic oil in combination. Such lubricant base oil generally has a kinematic viscosity of 2 to 20 mm$^2$/s at 100° C., and preferably 3 to 15 mm$^2$/s. It is allowable to properly select a mixed base oil having an optimum kinematic viscosity so as to well suit to lubricating conditions for mechanical friction sliding member to which the lubricant composition of the present invention is applied.

For the case the lubricant composition of the present invention is a mixture of the foregoing molecular complex compound and a lubricant base oil, preferable amount of blending of such molecular complex composition is 0.01 wt % or above of the total weight of the lubricant base oil, more preferably 0.01 to 10 wt %, and still more preferably 0.05 to 2 wt %. Content of the lubricant base oil is preferably 50 wt % or above. For the embodiment using no lubricant base oil, the molecular complex composition is preferably contained in an amount of 50 wt % or above.

While the lubricant composition of the present invention contains the foregoing molecular complex composition as a major component, it is also allowable, as occasion demands, to add any known additives having been used for conventional lubricant such as bearing oil, gear oil and power transmission oil, in order to attain practical performances adopted for the individual applications within a range not adversely affecting the effects of the present invention, where such additives include wear preventive agent, extreme pressure agent, antioxidant, viscosity index raising agent, clean dispersion aid, metal passivation agent, corrosion preventive agent, rust preventive agent, and defoaming agent.

The lubricant composition of the present invention can be prepared by adding "n" (n is an integer of 1 or above) kinds of keto-enol tautomeric compounds represented by the formula (I) (but excluding any compound represented by the foregoing formula (TAM)) to thereby produce a molecular complex compound composed of such "n" kinds of keto-enol tautomeric compounds. For example, a lubricant composition having a form of mixture with a lubricant base oil can be prepared by adding "n" (n is an integer of 1 or above) kinds of keto-enol tautomeric compounds represented by the formula (I) to a lubricant base oil to thereby form the molecular complex compound within such base oil. It is also allowable to preliminarily form the molecular complex compound and to add thus produced complex compound to the base oil. On the other hand, for the case without using the base oil, the lubricant composition can be prepared by mixing two or more keto-enol tautomeric compounds represented by the formula (I) to thereby form the molecular complex compound.

For the case of the lubricant composition containing a molecular complex compound which comprises (thio)carboxylic acid and a keto-enol tautomeric compound represented by the formula (I) (but excluding any compound represented by the foregoing formula (TAM)) can be prepared by adding at least one of keto-enol tautomeric compounds represented by the formula (I) (but excluding any compound represented by the foregoing formula (TAM)) and at least one of keto-enol tautomeric compounds represented by the formula (XII) to thereby form the molecular complex compound having both compounds as the constituents. For a lubricant composition having a form of a mixture with a base oil, (thio)carboxylic acid and the compound represented by the foregoing compound represented by the formula (I) may preliminarily be mixed to thereby produce the molecular complex compound containing both compounds and is then added to a base oil, or may independently be added to the base oil and the both are then mixed to thereby form the molecular complex compound containing both compounds within such lubricant base oil.

When supplied on the sliding surfaces which relatively move under contact with each other, the lubricant composition of the present invention can beneficially lower the friction coefficient of such sliding surfaces and improve the wear resistance of such sliding surfaces. What is better, such effects are maintained for a long period. The lubricant composition of the present invention can successfully reduce burn-in, improve wear resistance and keep the friction coefficient low even when it is supplied onto the surface moving under a friction condition which is severe enough for the conventional lubricating oil or lubricant such as grease to cause breakage of the oil film. For example, the lubricant composition of the present invention can preferably be used as a energy-saving lubricant for bearings or gears which move under severe friction conditions, and can further contribute to improvement in the reliability and downsizing of sliding members. The lubricant composition of the present invention has specific features of low friction coefficient, high wear resistance and extreme pressure properties under severe lubricating conditions. The lubricant composition of the present invention can successfully maintain a sufficient level of viscosity even under temperature as low as −40° C., if the various keto-enol tautomeric compounds are properly selected and mixed, which allows use of such composition under low temperatures and adds practical value thereof.

The lubricant composition of the present invention can exhibit an excellent lubricating effect even when used without a lubricant base oil, so that it is successfully adoptable typically to micro-machines to which a large amount of lubricant cannot be supplied. Since the metal complex compound can readily form a film on the surface of metal or metal oxide to thereby exhibit such lubricating effect, so that it is also preferably used as a lubricant for reducing friction between the surface of magnetic recording medium and magnetic recording head.

EXAMPLES

The present invention will more specifically be explained referring to preferred examples. It is to be noted that materials, reagents, ratio of use thereof, and operation can properly be modified without departing from the spirit of the present invention. Therefore the scope of the present invention is by no means limited to the preferred examples described below.

Examples 1 to 8

As shown in Table 1, the complex compounds (1), (2), (3) and (4) were independently used or used as being respectively dissolved in a lubricant base oil to thereby obtain lubricant for Examples 1 to 8 as listed in Table 1. The fact that the complex compounds (1), (2), (3) and (4) really form the complex compounds was confirmed by DSC (differential scanning colorimetry) which shows complete disappearance of a phase transfer peak attributable to a single carboxylic acid or barbituric acid, and appearance of a new phase transfer peak attributable to the complex compound. It was also found that the keto-enol tautomeric compounds composing the complex compounds (1), (2), (3) and (4) showed pKa of 2 to 12 in their enol forms.

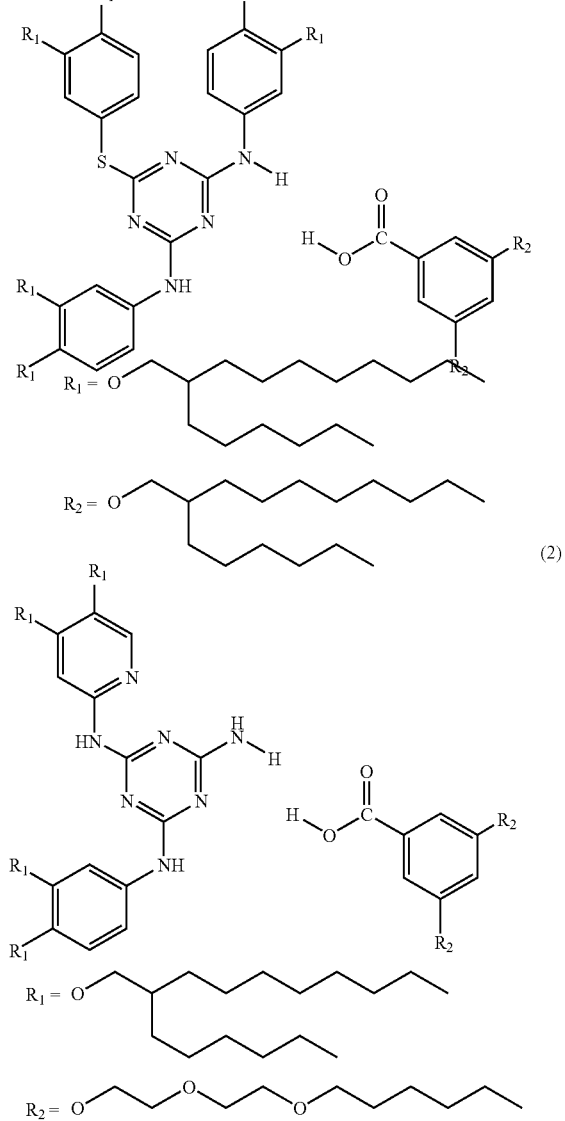

-continued (3)

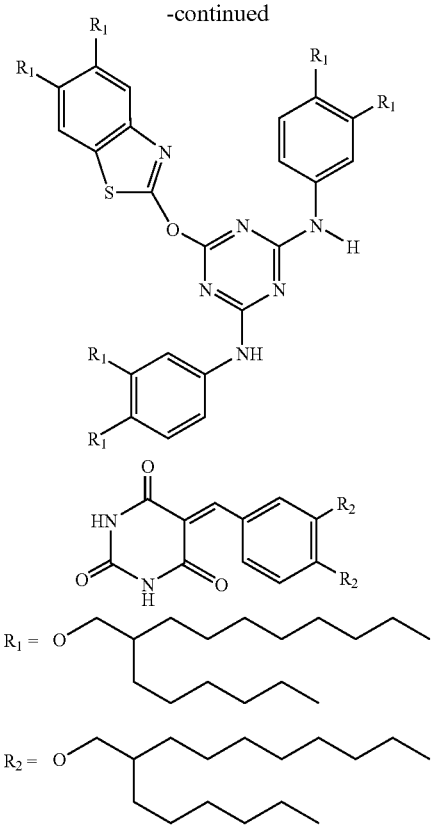

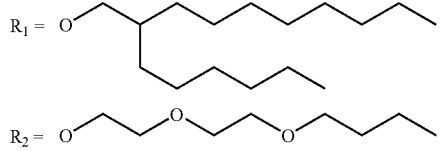

Comparative Examples 1 to 4

Lubricants were prepared by using only conventional lubricant base oil as listed in Table 2.

The lubricants obtained in Examples 1 to 8 and Comparative Examples 1 to 4 were subjected to reciprocating type (SRV) friction wear test in order to evaluate friction coefficient and wear resistance under the test conditions listed below.

[Test Conditions and Procedures of Reciprocating Type (SRV) Friction Wear Test]

Test Conditions

| | |
|---|---|
| Specimen (friction material): | SUJ-2 |
| Plate: | 24 mm in diameter, 7.9 mm thick |
| Cylinder: | 11 mm in diameter, 15 mm long |
| Temperature: | 150° C. |
| Load: | 50 N or 400 N |
| Amplitude: | 1.0 mm |
| Frequency: | 50 Hz |
| Testing period: | for 5 min. after the start of testing |

The friction coefficients were measured under the test conditions listed in the above under 50 N and 400 N, respectively. The wear resistance was assessed by measuring depth of wear-caused scars using a surface roughness gauge. Results for Examples 1 to 8 were shown in Table 1, and those for Comparative Examples 1 to 4 in Table 2.

TABLE 1

| | | Example 1 | Example 2 | Example 3 | Example 4 | Example 5 | Example 6 | Example 7 | Example 8 |
|---|---|---|---|---|---|---|---|---|---|
| Molecular complex compound | Species | (1) | (2) | (3) | (4) | (1) | (2) | (3) | (4) |
| | wt % | 100 | 100 | 100 | 100 | 10 | 10 | 10 | 10 |
| Lubricant base oil wt % | Pentaerythritol ester*1 | — | — | — | — | 90 | — | — | — |
| | Alkylbenzene*2 | — | — | — | — | — | 90 | — | — |
| | Naphthene-base mineral oil | — | — | — | — | — | — | 90 | — |
| | Parrafin-base mineral oil | — | — | — | — | — | — | — | 90 |

TABLE 1-continued

|  |  | Example 1 | Example 2 | Example 3 | Example 4 | Example 5 | Example 6 | Example 7 | Example 8 |
|---|---|---|---|---|---|---|---|---|---|
| SRV friction wear test at 50 N, 150° C. | Friction coefficient | 0.05 | 0.05 | 0.04 | 0.03 | 0.09 | 0.09 | 0.07 | 0.09 |
|  | Depth of abrasion scar (μm) | 0.0 | 0.0 | 0.0 | 0.0 | 0.0 | 0.0 | 0.0 | 0.0 |
| SRV friction wear test at 400 N, 150° C. | Friction coefficient | 0.06 | 0.05 | 0.04 | 0.05 | 0.10 | 0.09 | 0.09 | 0.07 |
|  | Depth of abrasion scar (μm) | 0.0 | 0.0 | 0.0 | 0.0 | 0.0 | 0.0 | 0.0 | 0.0 |

[1]Hexanoic acid ester of pentaerythritol
[2]Alkylbenzene having $C_{10}$ alkyl group

TABLE 2

|  |  | Comparative Example 1 | Comparative Example 2 | Comparative Example 3 | Comparative Example 4 |
|---|---|---|---|---|---|
| Lubricant base oil wt % | Pentaerythritol ester[1] | 100 | — | — | — |
|  | Alkylbenzene[2] | — | 100 | — | — |
|  | Naphthene-base mineral oil | — | — | 100 | — |
|  | Paraffin-base mineral oil | — | — | — | 100 |
| SRV friction wear test at 50 N, 150° C. | Friction coefficient | 0.21 | 0.22 | 0.25 | 0.22 |
|  | Depth of abrasion scar (μm) | 0.7 | 0.6 | 0.8 | 0.7 |
| SRV friction wear test at 400 N, 150° C. | Friction coefficient | 0.22 | 0.23 | 0.25 | 0.22 |
|  | Depth of abrasion scar (μm) | 0.7 | 0.6 | 0.8 | 0.7 |

[1]Hexanoic acid ester of pentaerythritol
[2]Alkylbenzene having $C_{10}$ alkyl group Examples 9 to 14

The complex compounds (5) to (10) were subjected to reciprocating type (SRV) friction wear test under conditions listed below at 40° C. and 120° C. in order to evaluate friction coefficient and apparent viscosity at each temperature.

Test Conditions

Tests were subjected under Cylinder on Plate Test.
Specimen (friction material): SUJ-2
Plate: 24 mm in diameter, 7.9 mm thick
Cylinder: 11 mm in diameter, 15 mm long
Temperature: 40° C. or 120° C.
Load: 400 N
Amplitude: 1.0 mm
Frequency: 50 Hz
Testing period: for 5 min. after the start of testing The result obtained by measuring under above test condition are shown in Table 3.

TABLE 3

|  |  | Example 9 | Example 10 | Example 11 | Example 12 | Example 13 | Example 14 |
|---|---|---|---|---|---|---|---|
| Molecular complex compound | Species | (5) | (6) | (7) | (8) | (9) | (10) |
|  | wt % | 100 | 100 | 100 | 100 | 100 | 100 |
| SRV friction wear test at 400 N, 40° C. | Friction coefficient | 0.05 | 0.04 | 0.04 | 0.04 | 0.07 | 0.09 |
|  | Apparent viscosity at 40° C. (mPa · s) | 650 | 320 | 300 | 450 | 40 | 2000 |
| SRV friction wear test at 400 N, 120° C. | Friction coefficient | 0.03 | 0.03 | 0.03 | 0.04 | 0.06 | 0.08 |
|  | Apparent viscosity at 120° C. (mPa · s) | 35 | 25 | 25 | 30 | 10 | 100 |

TABLE 3-continued
(5)
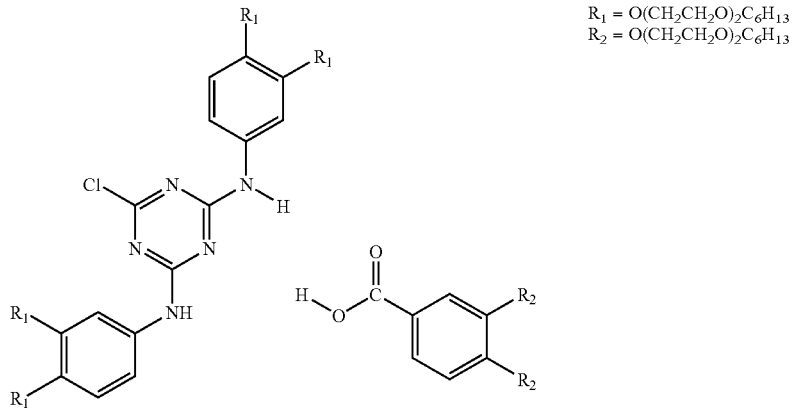
$R_1 = O(CH_2CH_2O)_2C_6H_{13}$
$R_2 = O(CH_2CH_2O)_2C_6H_{13}$
(6)
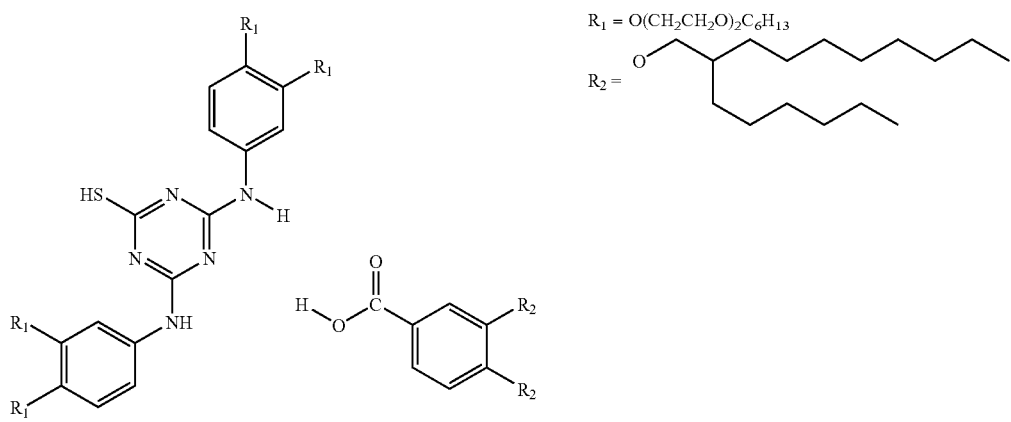
$R_1 = O(CH_2CH_2O)_2C_6H_{13}$
$R_2 = $
(7)
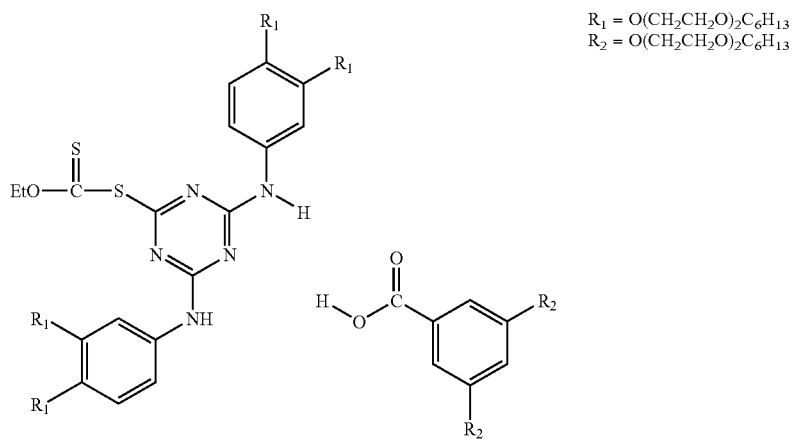
$R_1 = O(CH_2CH_2O)_2C_6H_{13}$
$R_2 = O(CH_2CH_2O)_2C_6H_{13}$ TABLE 3-continued (8) 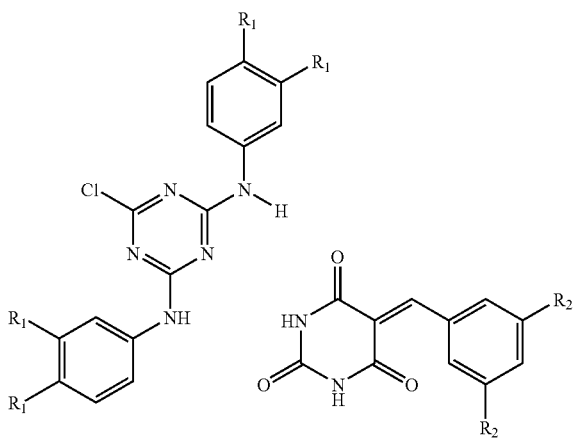

$R_1 = O(CH_2CH_2O)_2C_6H_{13}$
$R_2 = O(CH_2CH_2O)_2C_6H_{13}$ (9) 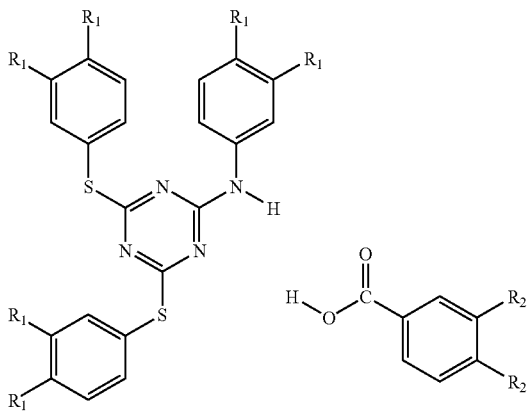

$R_1 = (CH_2CH_2O)_2C_6H_{13}$
$R_2 = (CH_2CH_2O)_2C_6H_{13}$

(10) 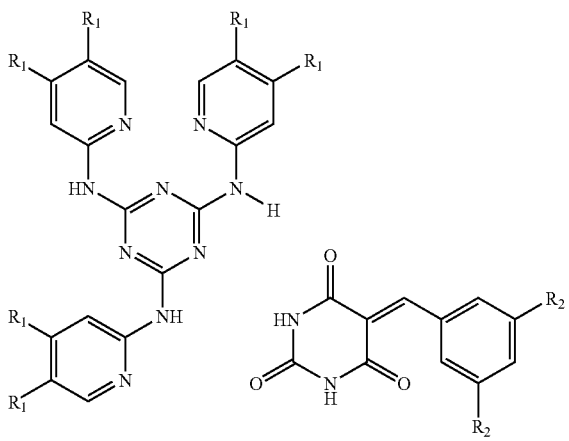

$R_1 = OC_{12}H_{25}$
$R_2 = OC_{12}H_{25}$

From the evaluation results of Examples and Comparative Examples, it was made clear that use of the complex compound independently or use as a major component while being mixed with a lubricant base oil can successfully provide a practical lubricating composition having an excellent wear resistance and low friction coefficient even under a high load condition.

As has been described in the above, the present invention is successful in providing a lubricant composition capable of exhibiting excellent properties not only in a state of mixture with conventional lubricant base oil, but also in a state not mixed with such lubricant base oil, and a method for preparing thereof. The present invention is also successful in providing a lubricant composition capable of retaining low friction property and high wear resistance on the sliding surface for a long period, and a method for preparing thereof. The present invention is further successful in providing a lubricant composition capable of readily forming a uniform thin film, and being applicable to the surface of magnetic recording media or micro-machines, and a method for preparing thereof. The present invention is still further successful in providing a lubricant composition excluding environmentally-less-compatible heavy metals, phosphate group and sulfides to thereby concomitantly achieve both of longer service life and environmental compatibility, and a method for preparing thereof.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A lubricant composition comprising a molecular complex formed between a substrate molecule (s) and a receptor molecule (p) having mutual steric complimentarity, the complex being formed by hydrogen bonding between multiple interaction sites of the substrate and receptor in the form of complementary tautomeric functional groups such that the resulting molecular complex has a planar structure; with the proviso that the complex is not formed from a compound of formula (TAM):

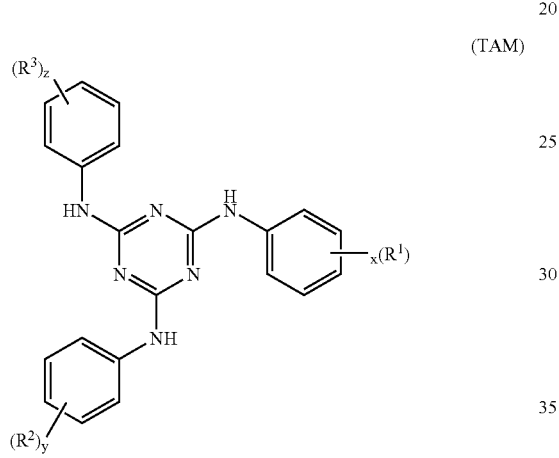
(TAM)

wherein the substituents $R^1$, $R^2$ and $R^3$ independently represent a substituent and the indices x, y and z independently represent an integer of 1 to 5; and wherein each of the substrate molecule and the receptor molecule is a compound selected from the group consisting of compounds represented by the formulae (III) to (XI);

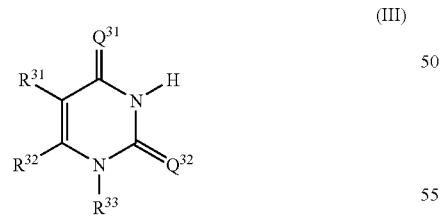
(III)

wherein $R^{31}$ to $R^{33}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{31}$ and $Q^{32}$ independently represent an oxygen atom or a sulfur atom; and $R^{31}$ and $R^{32}$, or $R^{32}$ and $R^{33}$ may optionally bind with each other to form a cyclic structure;

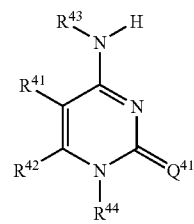
(IV)

wherein $R^{41}$ to $R^{44}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{41}$ represents an oxygen atom or a sulfur atom; and $R^{41}$ and $R^{42}$, $R^{41}$ and $R^{43}$, or $R^{42}$ and $R^{44}$ may optionally bind with each other to form a cyclic structure;

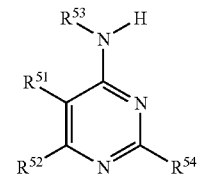
(V)

wherein $R^{51}$ to $R^{54}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and $R^{51}$ and $R^{52}$, or $R^{51}$ and $R^{53}$ may optionally bind with each other to form a cyclic structure;

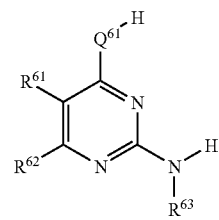
(VI)

wherein $R^{61}$ to $R^{63}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{61}$ represents an oxygen atom or sulfur atom; and $R^{61}$ and $R^{62}$ may optionally bind with each other to form a cyclic structure;

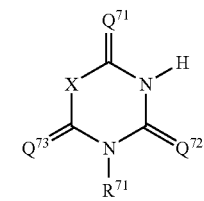
(VII)

wherein $Q^{71}$ to $Q^{73}$ independently represents an oxygen atom or a sulfur atom; X represents —C(=R$^{71}$)— or —C(R$^{72}$)(R$^{73}$)—; R$^{71}$ represents a substitutive group; R$^{72}$ and R$^{73}$ independently represents a hydrogen atom or a substitutive group; at least one of R$^{71}$ to R$^{73}$ represents a substitutive group containing a $C_4$ or longer alkyl chain or oligoalkyleneoxy chain, a $C_2$ or longer perfluoroalkyl chain, perfluoroalkyl ether chain or organic polysilyl chain; and R$^{72}$ and R$^{73}$ may optionally bind with each other to form a cyclic structure;

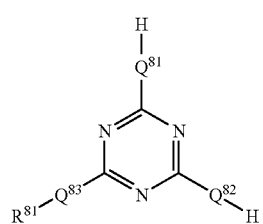

(VIII)

wherein $Q^{81}$ to $Q^{83}$ independently represents an oxygen atom, a N(R$^{82}$); R$^{81}$ and R$^{82}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and R$^{81}$ and R$^{82}$ may optionally bind with each other to form a cyclic structure when $Q^{83}$ represents N(R$^{82}$);

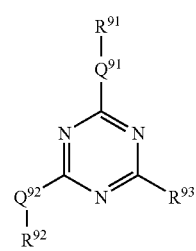

(IX)

wherein $Q^{91}$ and $Q^{92}$ independently represents a single bond, N(R$^{94}$) wherein R$^{94}$ represents a hydrogen or $C_{1-30}$ alkyl group, oxygen atom, sulfur atom, carbonyl, sulfonyl, or any combination thereof; R$^{91}$ and R$^{92}$ independently represents a hydrogen atom, substituted or unsubstituted alkyl group, alkenyl group, alkynyl group, aryl group or heterocyclic group; and R$^{93}$ represents a halogen atom, hydroxyl, amino, mercapto, cyano, sulfide, carboxyl or a salt thereof, sulfo or a salt thereof, hydroxyamino, ureido, or urethane;

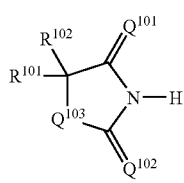

(X)

wherein $Q^{101}$ to $Q^{103}$ independently represents an oxygen atom, sulfur atom or N(R$^{103}$); and R$^{101}$ to R$^{103}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and

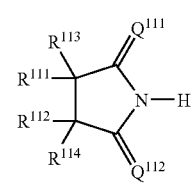

(XI)

wherein $Q^{111}$ and $Q^{112}$ independently represents an oxygen atom, sulfur atom or N(R$^{115}$); R$^{111}$ to R$^{115}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and R$^{111}$ and R$^{113}$, R$^{113}$ and R$^{114}$, R$^{113}$ and R$^{115}$, R$^{112}$ and R$^{114}$, or R$^{114}$ and R$^{115}$ may optionally bind with each other to form a cyclic structure.

2. A lubricant composition according to claim 1, wherein the substrate molecule or the receptor molecule is a compound having a pKa value of 2 to 12 in its enol form.

3. A lubricant composition according to claim 1, wherein the molecular complex shows a thermal phase transfer temperature pattern measured by differential scanning calorimetry (DSC) which differs from those shown by the component compounds thereof.

4. A lubricant composition according to claim 1, further comprising a lubricant base oil in an amount of 50 wt % or more.

5. A lubricant composition according to claim 1, having an apparent viscosity of 1000 mPa·s or more at 40° C. and 20 mPa·s or less at 120° C.

6. A method for reducing friction between two surfaces, comprising applying the lubricant composition according to claim 1 to a surface.

7. A method of preparing a lubricant composition as defined in claim 1 comprising the step of adding substrate molecules (s) to receptor molecules (ρ) to form a molecular complex having a planar structure.

8. A lubricant composition comprising a molecular complex formed between a substrate molecule (s) and a receptor molecule (ρ) having mutual steric complimentarity, the complex being formed by hydrogen bonding between multiple interaction sites of the substrate and receptor in the form of complementary tautomeric functional groups such that the resulting molecular complex has a planar structure; with the proviso that the complex is not formed from a compound of formula (TAM):

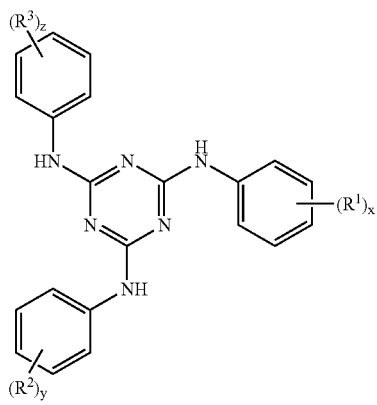

(TAM)

wherein the substituents $R^1$, $R^2$ and $R^3$ independently represent a substituent and the indices x, y and z independently represent an integer of 1 to 5; and wherein one of the substrate molecule and the receptor molecule is a compound selected from the group consisting of compounds represented by the formulae (III) to (XI), and the substrate molecule or the receptor molecule that is not represented by a compound selected from the group consisting of compounds represented by the formula (III) to (XI), is a compound represented by the formula (XII):

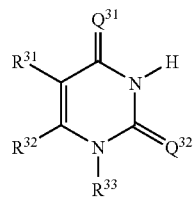

(III)

wherein $R^{31}$ to $R^{33}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{31}$ and $Q^{32}$ independently represent an oxygen atom or a sulfur atom; and $R^{31}$ and $R^{32}$, or $R^{32}$ and $R^{33}$ may optionally bind with each other to form a cyclic structure;

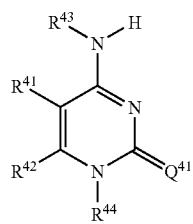

(IV)

wherein $R^{41}$ to $R^{44}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{41}$ represents an oxygen atom or a sulfur atom; and $R^{41}$ and $R^{42}$, $R^{41}$ and $R^{43}$, or $R^{42}$ and $R^{44}$ may optionally bind with each other to form a cyclic structure;

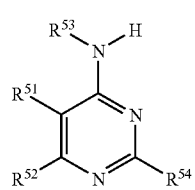

(V)

wherein $R^{51}$ to $R^{54}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and $R^{51}$ and $R^{52}$, or $R^{51}$ and $R^{53}$ may optionally bind with each other to form a cyclic structure;

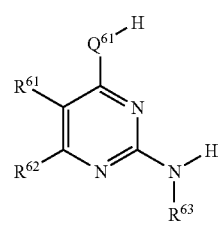

(VI)

wherein $R^{61}$ to $R^{63}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; $Q^{61}$ represents an oxygen atom or sulfur atom; and $R^{61}$ and $R^{62}$ may optionally bind with each other to form a cyclic structure;

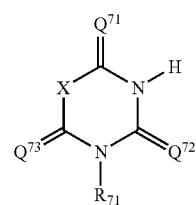

(VIII)

wherein $Q^{71}$ to $Q^{73}$ independently represents an oxygen atom or a sulfur atom; X represents —C(=$R^{71}$)— or —C($R^{72}$)($R^{73}$)—; $R^{71}$ represents a substitutive group; $R^{72}$ and $R^{73}$ independently represents a hydrogen atom or a substitutive group; at least one of $R^{71}$ to $R^{73}$ represents a substitutive group containing a $C_4$ or longer alkyl chain or oligoalkyleneoxy chain, a $C_2$ or longer perfluoroalkyl chain, perfluoroalkyl ether chain or organic polysilyl chain; and $R^{72}$ and $R^{73}$ may optionally bind with each other to form a cyclic structure;

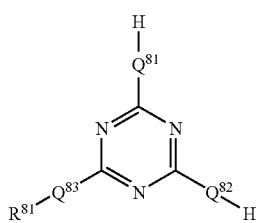

(VIII)

wherein $Q^{81}$ to $Q^{83}$ independently represents an oxygen atom, a sulfur atom or $N(R^{82})$; $R^{81}$ and $R^{82}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and $R^{81}$ and $R^{82}$ may optionally bind with each other to form a cyclic structure when $Q^{83}$ represents $N(R^{82})$

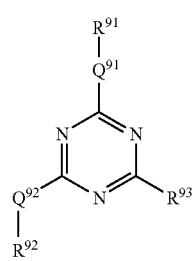

(IX)

wherein $Q^{91}$ and $Q^{92}$ independently represents a single bond, $N(R^{94})$ wherein $R^{94}$ represents a hydrogen or $C_{1-30}$ alkyl group, oxygen atom, sulfur atom, carbonyl, sulfonyl, or any combination thereof; $R^{91}$ and $R^{92}$ independently represents a hydrogen atom, substituted or unsubstituted alkyl group, alkenyl group, alkynyl group, aryl group or heterocyclic group; and $R^{93}$ represents a halogen atom, hydroxyl, amino, mercapto, cyano, sulfide, carboxyl or a salt thereof, sulfo or a salt thereof, hydroxyamino, ureido, or urethane;

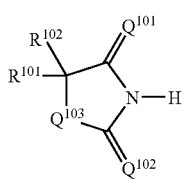

(X)

wherein $Q^{101}$ to $Q^{103}$ independently represents an oxygen atom, sulfur atom or $N(R^{103})$; and $R^{101}$ to $R^{103}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and

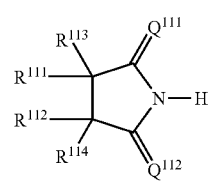

(XI)

wherein $Q^{111}$ and $Q^{112}$ independently represents an oxygen atom, sulfur atom or $N(R^{115})$; $R^{111}$ to $R^{115}$ independently represents a hydrogen atom or a substitutive group, at least one of which being a substitutive group containing a $C_4$ or longer alkyl chain or oligoalkyleneoxy chain, a $C_2$ or longer perfluoroalkyl chain, perfluoroalkyl ether chain or organic polysilyl chain; and $R^{111}$ and $R^{113}$, $R^{113}$ and $R^{114}$, $R^{113}$ and $R^{115}$, $R^{112}$ and $R^{114}$, or $R^{114}$ and $R^{115}$ may optionally bind with each other to form a cyclic structure;

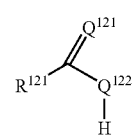

(XII)

wherein $R^{121}$ represents a substitutive group; and $Q^{121}$ and $Q^{122}$ independently represents an oxygen atom or a sulfur atom.

9. A lubricant composition according to claim 8, wherein the molecular complex shows a thermal phase transfer temperature pattern measured by differential scanning calorimetry (DSC) which differs from those shown by the component compounds thereof.

10. A lubricant composition according to claim 8, further comprising a lubricant base oil in an amount of 50 wt % or more.

11. A lubricant composition according to claim 8, having an apparent viscosity of 1000 mPa·s or more at 40° C. and 20 mPa·s or less at 120° C.

12. A method for reducing friction between two surfaces, comprising applying the lubricant composition according to claim 8 to a surface.

13. A method of preparing a lubricant composition as defined in claim 8 comprising the step of adding substrate molecules (s) to receptor molecules (ρ) to form a molecular complex having a planar structure.

* * * * *